(12) United States Patent
Curry et al.

(10) Patent No.: US 11,319,589 B2
(45) Date of Patent: *May 3, 2022

(54) METHODS OF DETERMINING THE PRESENCE OR ABSENCE OF A PLURALITY OF TARGET POLYNUCLEOTIDES IN A SAMPLE

(71) Applicants: AFFYMETRIX, INC., Carlsbad, CA (US); The United States of America, as Represented by the Secretary of Agriculture, Washington, DC (US)

(72) Inventors: John D. Curry, Concord, CA (US); Heather Koshinsky, El Cerrito, CA (US); Amanda K. Lindholm-Perry, Clay Center, NE (US); Richard M. Thallman, Blue Hill, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/802,449

(22) Filed: Feb. 26, 2020

(65) Prior Publication Data

US 2020/0263247 A1 Aug. 20, 2020

Related U.S. Application Data

(62) Division of application No. 13/824,348, filed as application No. PCT/US2013/021379 on Jan. 14, 2013, now Pat. No. 10,648,030.

(60) Provisional application No. 61/586,635, filed on Jan. 13, 2012.

(51) Int. Cl.
| | |
|---|---|
| *C12P 19/34* | (2006.01) |
| *C12Q 1/6874* | (2018.01) |
| *C12Q 1/6827* | (2018.01) |
| *C12Q 1/6862* | (2018.01) |
| *C12Q 1/6869* | (2018.01) |
| *G01N 33/53* | (2006.01) |
| *C12Q 1/6806* | (2018.01) |

(52) U.S. Cl.
CPC ......... *C12Q 1/6874* (2013.01); *C12Q 1/6806* (2013.01); *C12Q 1/6827* (2013.01); *C12Q 1/6862* (2013.01); *C12Q 1/6869* (2013.01); *G01N 33/5308* (2013.01)

(58) Field of Classification Search
CPC .................................................. C12Q 1/6862
See application file for complete search history.

(56) References Cited

U.S. PATENT DOCUMENTS

| | | | |
|---|---|---|---|
| 5,912,124 A | 6/1999 | Kumar et al. | |
| 6,027,889 A | 2/2000 | Barany et al. | |
| 6,124,092 A | 9/2000 | O'Neill et al. | |
| 6,511,810 B2 | 1/2003 | Bi et al. | |
| 6,518,025 B1 | 2/2003 | Steinborn et al. | |
| 6,534,293 B1 | 3/2003 | Barany et al. | |
| 7,504,218 B2 | 3/2009 | Harpe et al. | |
| 7,846,657 B2 | 12/2010 | Van Eijk et al. | |
| 7,935,488 B2 | 5/2011 | Zabeau et al. | |
| 8,460,866 B2 | 6/2013 | Van et al. | |
| 2003/0119004 A1 | 6/2003 | Wenz et al. | |
| 2004/0224311 A1 | 11/2004 | Telles et al. | |
| 2004/0229222 A1 | 11/2004 | Chui et al. | |
| 2005/0272071 A1 | 12/2005 | Lao et al. | |
| 2009/0029478 A1 | 1/2009 | Puskas | |
| 2009/0053687 A1 | 2/2009 | Colau et al. | |
| 2009/0136938 A1 | 5/2009 | Tao et al. | |
| 2010/0267585 A1 | 10/2010 | Terbrueggen et al. | |
| 2011/0003290 A1 | 1/2011 | Gale et al. | |
| 2011/0045462 A1 | 2/2011 | Fu et al. | |
| 2011/0136116 A1 | 6/2011 | Barany et al. | |
| 2011/0159499 A1 | 6/2011 | Hindson et al. | |
| 2012/0003633 A1 | 1/2012 | Kuijpers et al. | |
| 2015/0167077 A1 | 6/2015 | Fehr et al. | |
| 2016/0222447 A1 | 8/2016 | Stevens et al. | |

FOREIGN PATENT DOCUMENTS

| | | |
|---|---|---|
| CN | 101395280 A | 3/2009 |
| CN | 104830993 A | 8/2015 |
| EP | 1130113 A1 | 9/2001 |
| EP | 1319718 A1 | 6/2003 |
| EP | 1602733 A1 | 12/2005 |
| WO | WO-2004076692 A1 | 9/2004 |
| WO | WO-2005001113 A2 | 1/2005 |
| WO | WO-2005021794 A2 | 3/2005 |
| WO | WO-2005026389 A2 | 3/2005 |
| WO | WO-2007100243 A1 | 9/2007 |
| WO | WO-2013106807 A1 | 7/2013 |

OTHER PUBLICATIONS

Hu Fuquan: "Modern Gene Manipulation Technology", People's Military Medical Publishing House, Oct. 31, 2000, ISBN 7-80157-111-8, pp. 263-266.

Yanli Ji, et al., "Application of high through-put MLPA gene typing technique in the identification of 1 Del phenotypic family gene", Chinese Journal of Blood Transfusion, Jun. 25, 2012, vol. 25, No. 06, pp. 542-546.

Zhang Li, et al., "Combined application of MLPA and sequencing technique in the detection of Thalassemia gene defects", Practical Preventive Medicine, Jul. 25, 2014, No. 7, pp. 779-781.

Baird et al., "Rapid SNP Discovery and Genetic Mapping Using Sequenced RAD Markers," PLoS ONE, Oct. 2008, vol. 3, Issue 10, e3376, pp. 1-7.

Extended European Search Report for Application No. 16845310.8, dated Jan. 4, 2019, 7 pages.

(Continued)

*Primary Examiner* — Kenneth R Horlick

(74) *Attorney, Agent, or Firm* — Jinhee Chang

(57) ABSTRACT

A method for detecting the presence or absence of a target polynucleotide in a sample is described.

17 Claims, 52 Drawing Sheets

Specification includes a Sequence Listing.

(56) References Cited

OTHER PUBLICATIONS

Fujimoto et al., "Reversible photoligation of DNA via 5-vinyldeoxyuridine," Nucleic Acids Symposium Series No. 42, 1999, pp. 39-40.
International Search Report and Written Opinion for Application No. PCT/US2013/21379, dated Apr. 26, 2013, 8 pages.
Kumar et al., "Template-Directed Oligonucleotide Strand Ligation, Covalent Intramolecular DNA Circularization and Catenation Using Click Chemistry," Journal of the American Chemical Society, 2007, vol. 129, pp. 6859-6864.
Kvastad L., et al., "Single Cell Analysis of Cancer Cells Using An Improved RT-MLPA Method has Potential for Cancer Diagnosis and Monitoring," Scientific Reports, vol. 5, No. 1, Nov. 12, 2015 (Nov. 12, 2015), XP055535938, pp. 1-12, DOI: 10.1038/srep16519.
Lewis et al., "High-Density Detection of Restriction-Site-Associated DNA Markers for Rapid Mapping of Mutated Loci in Neurospora," Genetics, Oct. 2007, vol. 177, pp. 1163-1171.
Margulies et al., "Genome Sequencing in Microfabricated High-Density Picolitre Reactors", Nature, vol. 437, No. 15, 2005, pp. 376-380.
Miller et al., "RAD marker microarrays enable rapid mapping of zebrafish mutations," Genome Biology, 2007, vol. 8, Issue 6, Article R105, 10 pages.
Miller et al., "Rapid and cost-effective polymorphism identification and genotyping using restriction site associated DNA (RAD) markers," Genome Research, 2007, vol. 17, pp. 240-248.
PCT/US2016/060991, International Search Report and Written Opinion dated Mar. 16, 2017, 10 pages.
Sando et al., "Nonenzymatic DNA ligation in *Escherichia coli* cells," Nucleic Acids Research Supplement No. 2, 2002, pp. 121-122.
Shabarova et al., "Chemical ligation of DNA: the first non-enzymatic assembly of a biologically active gene," Nucleic Acids Research, 1991, vol. 19, No. 15, pp. 4247-4251.
Thallman et al., "Efficient computation of genotype probabilities for loci with many alleles: II. Iterative method for large, complex pedigrees," Journal of Animal Science, 2001, vol. 79, pp. 34-44.
Xu, Y et al., "High sequence fidelity in a non-enzymatic DNA autoligation reation", Nucl. Acids Res. Vol 27(3), 1999, pp. 875-881.
CN Office Action cited in 201680052075.1 dated Apr. 28, 2021.
Li, Xhang Yang, et al., "High-throughput genotyping MLPA assay in RHD genotyping for a Chinese pedigree with Del phenotype", Chin J. Blood Transfusion Jun. 2012, vol. 25, No. 06.
Zhang Li, et al., "Genetic diagnosis of thalassemias by multiplex ligation-dependent probe amplification combined with direct sequencing", Pract Prev Med, Jul. 2014, vol. 21, No. 7.

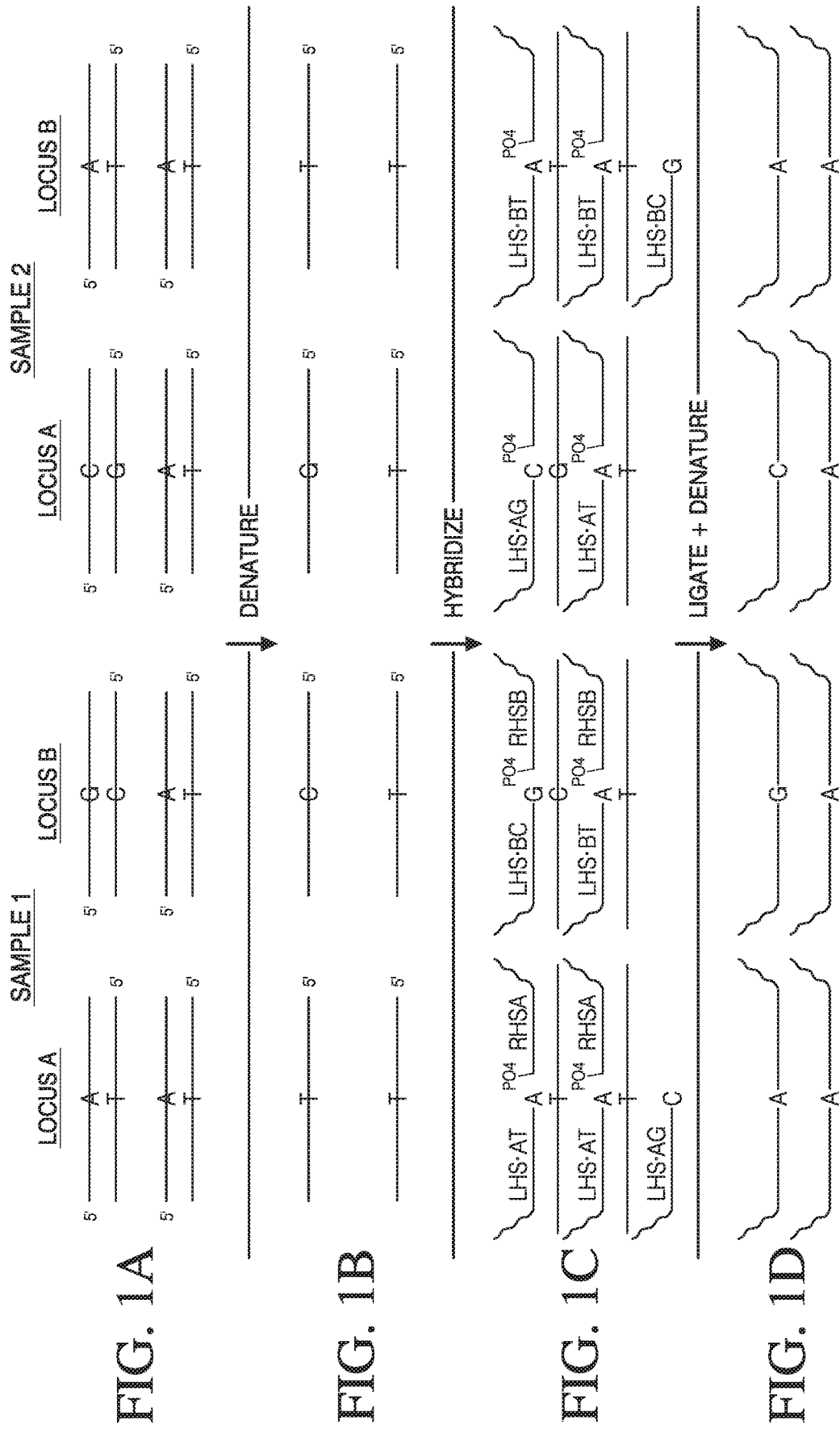

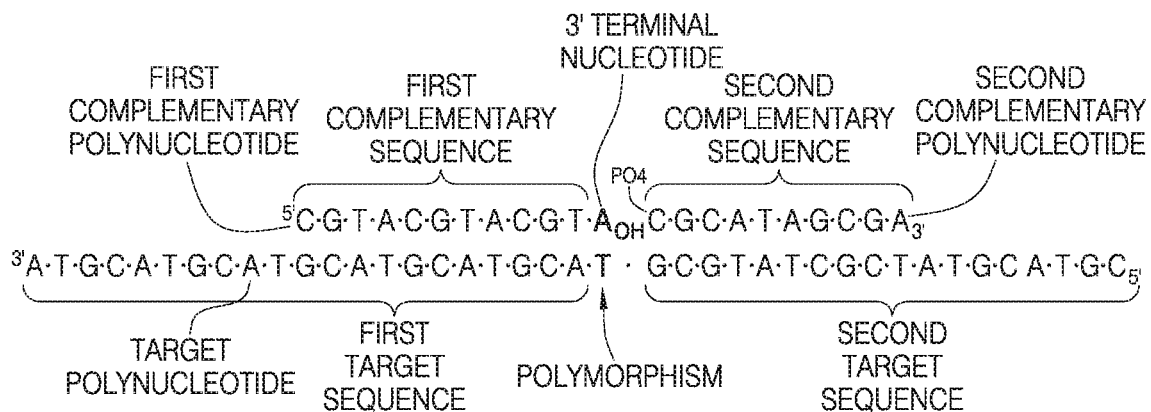
FIG. 2A
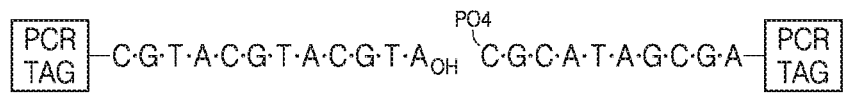
FIG. 2B
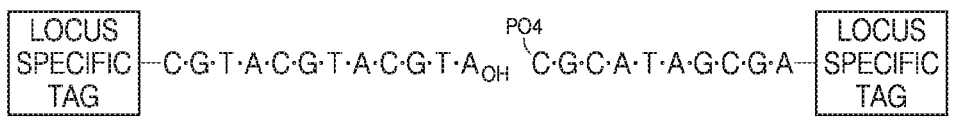
FIG. 2C
FIG. 2D
FIG. 2E

Diagram of the LHS and RHS MGST Probes

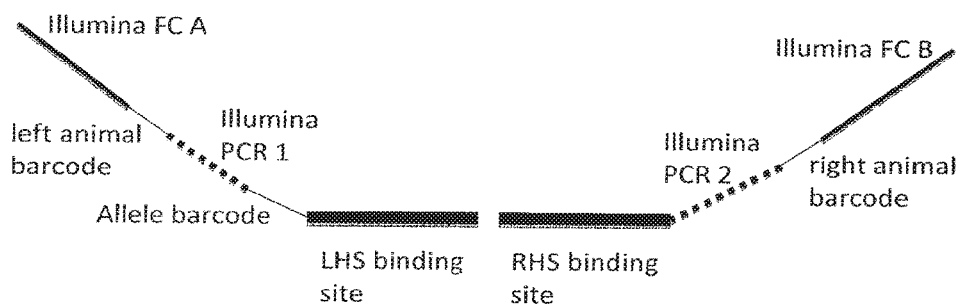

Figure Legend: Illumina FC A and B are fixed sequences and are required in order to anneal to the flow cell. Left and right barcode are the bases that identify the sample. The Illumina PCR 1 and 2 are Illumina fixed sequenced are required for bridge amplification of the amplicons. Allele barcode is unfixed and can be any barcode to spell out any of the four allele possibilities. LHS and RHS vary according to the locus to be interrogated.

FIG.3

| TT | AA | AG | CT | AA | AA | GG | TC |
|---|---|---|---|---|---|---|---|
| 192 | 193 | 194 | 195 | 196 | 197 | 198 | 249 |
| A>T | A>G | A>G | C>T | A>G | A>G | A>G | T>C |

FIG.7

Summary

Locus :195
Total :96
Total Callable :95
Correct :92
Wrong :3
Concordance :96.84 %
Min. Std. Deviation :9
Num. Clusters :3

FIG. 21 (cont.)

133_153_3_411.jpg

METHODS OF DETERMINING THE PRESENCE OR ABSENCE OF A PLURALITY OF TARGET POLYNUCLEOTIDES IN A SAMPLE

This application is a divisional application of U.S. application Ser. No. 13/824,348 (filed Apr. 2, 2014), now U.S. Pat. No. 10,648,030. U.S. application Ser. No. 13/824,348 is the national stage application of PCT Application No. PCT/US2013/021379 (filed Jan. 14, 2013). PCT Application No. PCT/US2013/021379 claims priority to and/or benefit under 35 U.S.C. § 119(e) to U.S. Provisional Application No. 61/586,635 (filed Jan. 13, 2012), all of which are hereby incorporated by reference, in their entirety.

GOVERNMENT RIGHTS

This invention was made with government funding under CRADA Number 58-3K95-1-1519-M provided by the United States Department of Agriculture, Agricultural Research Service (USDA/ARS). The government has certain rights in the invention.

FIELD

The present disclosure is directed to the scalable characterization of nucleic acids from multiple samples using parallel sequencing.

BACKGROUND

Current large scale, commercial genotyping methods are generally array based and are prohibitively expensive. This makes them unusable for routine or en mass genotyping of a moderate number of loci. Because genotyping for specific traits requires testing of a moderate number of loci from large numbers of subjects, commercial genotyping is rarely used.

Large scale genotyping can be performed using chip or bead array technology. However, genotyping using array technology is expensive on a per sample basis. While array technology can be scaleable (i.e. allowing the gathering of genotype information from tens of thousands of loci, or more, from a single sample), the per sample cost prevents wide-spread adoption of this method for genotyping large numbers of samples.

Described herein are methods and compositions for use in determining the presence or absence of a target polynucleotide in a sample.

SUMMARY

Disclosed herein is a method of detecting the presence or absence of a target polynucleotide in a sample, the method comprising the steps of: combining (i) a sample comprising a target polynucleotide, the target polynucleotide comprising a first target sequence and a second target sequence, (ii) a first complementary polynucleotide comprising a first complementary sequence, wherein the first complementary sequence is complementary to the first target sequence of the target polynucleotide, and (iii) a second complementary polynucleotide comprising a second complementary sequence, wherein the second complementary sequence is complementary to the second target sequence of the target polynucleotide; incubating the first and second complementary polynucleotides with the sample under conditions that allow hybridization of the first and second complementary sequences of the first and second polynucleotides with the first and second target sequences of the target polynucleotide; if the first complementary polynucleotide and the second complementary polynucleotide are hybridized to the same target polynucleotide, then joining the first complementary polynucleotide to the second complementary polynucleotide, to form a first product polynucleotide; and detecting the presence of the product polynucleotide in the sample, or detecting the absence of the product polynucleotide or nucleotide sequence in the sample. In some aspects, the 3' end of the first complementary polynucleotide is adjacent to the 5' end of the second complementary polynucleotide. The 3' end is joined to the 5' end.

In some cases the presently disclosed method may further include a polymerization step, digestion step, or repair step at any point before the joining step. In some cases the polymerization step can include elongation of the first and/or second complementary polynucleotides. In some cases, the digestion step can include digestion of the first and/or second complementary polynucleotides. In some cases, the repair step may include repair of the first and/or second complementary polynucleotides. In some cases the polymerization and/or repair step can be performed where the first and second complementary polynucleotides are hybridized to the same target polynucleotide, and the 5' end of one complementary polynucleotide is separated from the 3' end of the other polynucleotide by one or more nucleotides.

In various embodiments, the joining step may comprise covalent bonding or non-covalent bonding of the first and second complementary polynucleotides as described herein.

In various embodiments, a third complementary polynucleotide can hybridize to the target polynucleotide between the first and second complementary polynucleotides. The third polynucleotide is then joined to the first and second complementary polynucleotides to make a product polynucleotide including the first, second, and third complementary polynucleotide.

In some cases, the presently disclosed method may further include an enriching step at any point before the detecting step. The enriching step may increase the ratio of product polynucleotides to non-product polynucleotides. In some cases, the enriching step may comprise selecting the product polynucleotides by size, affinity, charge, single strand vs. double strand, or sequence. In some cases the enriching step may comprise amplification of the product polynucleotide. In other cases the enriching step may comprise removal of some or all of the non-product polynucleotides, for example by selection, segregation, or digestion. The enriching step can also be accomplished by increasing the concentration of the target polynucleotide.

In some cases, the first and/or second complementary polynucleotides can comprise one or more tag sequences. In various cases, the one or more tag sequences may aid in identifying the sample and/or target sequences. In various embodiments, the one or more tag sequences may allow the sample and/or target sequences to be detected without generating sequence data from the product polynucleotide.

In some variations, the present method may be for identifying the presence or absence of a plurality of different target polynucleotides. In these embodiments, there may be a plurality of sets of first and second complementary polynucleotides for hybridizing to the plurality of different target polynucleotides. For example, in variations of the method for identifying the presence or absence of a first target polynucleotide and a second target polynucleotide, there may be a first set of first and second complementary polynucleotides and a second set of first and second complementary polynucleotides. In these cases the first set of first and second polynucleotides may have complementary sequences that can hybridize to the first and second target sequences of the first target polynucleotide, and the second set of first and second complementary polynucleotides may have a first and a second complementary sequence that can hybridize to the first and second target sequence of the second target polynucleotide.

In some variations, the method may further comprise a pooling step at any point after the joining step, wherein product polynucleotides from various samples are pooled to create a library of product polynucleotides from different samples. In some cases, the sequence of various product polynucleotides from various samples may be determined at the same time. In some cases, such as when product polynucleotides are sequenced, the various product polynucleotides are sequenced in a single lane of a single flow cell. In some cases, such as when product polynucleotides are sequenced, the various product polynucleotides are sequenced in a single physical substrate. In some cases, such as when product polynucleotides are sequenced, the various product polynucleotides are sequenced in a single masked portion of a single slide. In some cases, such as when product polynucleotides are sequenced, the various product polynucleotides are sequenced in a single sequence data generation reaction. In some cases, such as when product polynucleotides are sequenced, the various product polynucleotides are sequenced in a single physical space of a single sequence data generation reaction. In some cases, the various product polynucleotides produced by pooling multiple samples may be sequenced as a single sample. In these cases, the first and/or second complementary sequences can comprise a sample-specific tag. In some cases, the sample-specific tag may be added to a product polynucleotide, for example by ligation of the sample specific tag to the product polynucleotide, or during an enrichment step, such as during amplification by PCR, wherein a PCR primer may have a sample-specific tag sequence.

In some cases, for example where a sample may or may not comprise a plurality of different target polynucleotides, such as embodiments wherein the target polynucleotides comprise different gene sequences and/or different genetic loci, the first and second complementary polynucleotides may comprise locus-specific tags.

In some cases, for example where a sample contains two target polynucleotides that may or may not be identical but for a polymorphism, the first and second complementary polynucleotides may comprise polymorphism-specific tags.

In some cases the method may be used to detect the presence or absence of one or more nucleotides or nucleotide sequences, a polymorphism, a translocation, deletion, insertion, modified nucleotide, or a combination thereof. In various embodiments, a polymorphism, translocation, deletion, insertion, modified nucleotide, or combination thereof can include one or more bases.

In one variation, the method can be used to detect the presence or absence of a nucleotide polymorphism in a target polynucleotide from a sample, the second complementary sequence can further comprise a phosphorylated 5' nucleotide; the joining step can further comprise ligating the 3' end of the first complementary polynucleotide to the 5' end of the second complementary polynucleotide. This method can further comprise an enriching step comprising amplifying the product polypeptide by polymerase chain reaction. In some of these cases amplification can further comprise using a first PCR primer comprising a sequence that is complementary to a portion of the second complementary polynucleotide, and a second PCR primer comprising a sequence that is identical to a portion of the first product polynucleotide to create a first amplified product polynucleotide. In some cases, the first and or second PCR primer may further comprise a sample-specific tag sequence.

In some variations of the disclosed method, for use in detecting a polymorphism on a target sequence, the polymorphism on the target polynucleotide may comprise a single nucleotide or multiple nucleotide substitutions. In some examples, the polymorphism can be one, two, three, four, five, or six or more nucleotides in length.

Some variations of the disclosed method for detecting a polymorphism can include a plurality of first complementary polynucleotides that differ in the identity of the 3' nucleotide or 3'-polynucleotide sequences. Some variations of the disclosed method for detecting a polymorphism can include a plurality of second complementary polynucleotides that differ in the identity of the 5'-nucleotide or 5'-polynucleotide sequences. In some variations of the method, wherein the each base of the polymorphism can be one of four possible nucleotides, and thus four sets of first and second complementary polynucleotides can be used. In these methods, some sets of first and second complementary polynucleotides may have the same second complementary polynucleotides.

In some variations of the presently disclosed method, a specific tag sequence can correspond to the identity of a polynucleotide and can aid in identifying the 3'-nucleotide or 3'-nucleotide sequences of the first polynucleotide. In some variations of the presently disclosed method, a specific tag sequence can correspond to the identity of a polynucleotide and can aid in identifying the 5'-nucleotide or 5'-nucleotide sequences of the second polynucleotide.

In some variations, the method further includes a first and/or second PCR primer comprising a sample-specific tag, wherein the tag or tag combination correspond to and are unique for the sample identity.

In some variations, the first complementary polynucleotide of the disclosed method further comprises a universal base such as inosine, positioned 2, 3, 4, 5, 6, 7, 8, 9, 10, or more bases from the 3' nucleotide. Other universal bases include 3-nitropyrrole and 5-nitroindole. Any universal base (one that does not favor particular base-pairing) can be used in these positions.

The presently disclosed method, in some variations, is used to detect the presence or absence of a given polymorphism positioned between the first and second target sequences. In some cases, for example wherein the sample may comprise more than one target polynucleotide having the same first and second target sequence, and different polymorphic nucleotides positioned between the target sequences, the method can be used to genotype a first locus in the sample with the use of multiple first complementary polynucleotides differing in their 3' nucleotide identities.

In some variations, the number of product polynucleotides may correspond to the number of independent sequence reading events. In some variations wherein target polynucleotides are obtained from a diploid organism, the organism may be determined to be homozygous or heterozygous based on the number of sequencing reads for a given locus and the number of sequencing reads for one or more polymorphisms. In some cases, a given locus can be heterozygous wherein the number of sequencing reads for one target sequence having one polymorphism comprises about 45-55% of the number of sequencing reads for all target sequences at that locus. In many cases, a given locus can be homozygous wherein the number of sequencing reads for one target sequence having a polymorphism comprises more than about 50%, 60%, 70%, 80%, 90%, 95%, or 99% and/or less than about 50%, 40%, 30%, 20%, 10%, 5%, or 1% of the number of sequencing reads for all target sequences at that locus. It will be appreciated that different percentages of sequence reads can show homozygous or heterozygous sequences for different loci.

In some variations of the disclosed method, the amplifying step may further comprise the nucleotide deoxyuridine triphosphate (dUTP) and uracil DNA glycosylase (UNG), and may begin with a step at or about 37° C. to destroy (UNG destroys any dUTP containing DNA) any contaminating amplification products (those that contain dUTP), followed by a high temperature step to denature or deactivate the uracil DNA glycosylase before synthesis of the target. This can avoid potential amplification of the contaminating amplification products.

In some disclosed variations, the method product polynucleotides are sequenced by Illumina sequencing. In these cases, the PCR primers and/or the first and second complementary polynucleotides may include Illumina sequences to aid in capture on an Illumina flow cell and bridge amplification on the flow cell.

In some variations of the disclosed method, the polymorphism may be a methylated or non-methylated nucleotide sequences. In other variations, the polymorphism may be a deletion, insertion, or translocation. In other variations, methylation-sensitive restriction endonucleases may be used to aid in creating target polynucleotides. In some variations, copy number of a given locus may be determined.

BRIEF DESCRIPTION OF THE DRAWINGS

FIG. 1A-1D depicts method of analyzing the genotype of two samples at two different polymorphic loci.

FIG. 2A-2E depicts a first target polynucleotide and a first and second complementary polynucleotide used in one variation of the presently described method.

FIG. 3 depicts a set of first and second complementary polynucleotides for use in the method wherein sequencing is performed on the Illumina sequencing devices.

FIG. 7 depicts a single ligation-dependent assay for eight loci on a single target DNA sample, and resolved by gel electrophoresis.

DETAILED DESCRIPTION

Figure 4:
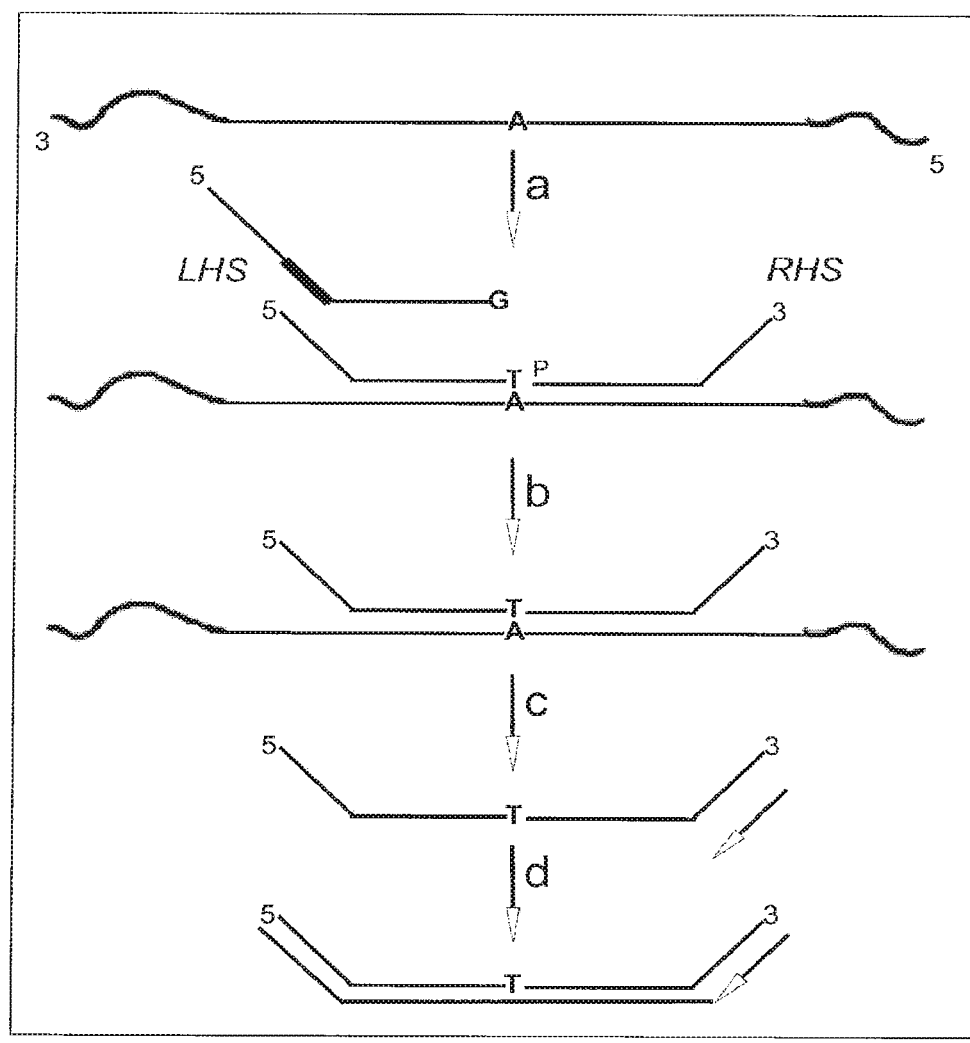
FIG. 4 depicts the use of ligation dependent genotyping. Step (a) shows a three polynucleotide set consisting of two first complementary polynucleotides (one with a 3' G nucleotide and its counterpart with a 3' T nucleotide) and one second complementary polynucleotide that is 5' phosphorylated (P) added to denatured target DNA. Step (b) shows the correctly hybridized first complementary polynucleotide successfully joined via enzymatic ligation to the second complementary polynucleotide. Step (c) shows the first PCR step where an oligo nucleotide hybridizes to the newly formed (LHS ligated to RHS) product polynucleotide and a full length (step d) complementary strand arises.

A method is described for detecting the presence or absence of a target polynucleotide in a sample, the method comprising the steps of: combining (i) a sample comprising a target polynucleotide, the target polynucleotide comprising a first target sequence and a second target sequence, (ii) a first complementary polynucleotide comprising a first complementary sequence, wherein the first complementary sequence is complementary to the first target sequence of the target polynucleotide, and (iii) a second complementary polynucleotide comprising a second complementary sequence, wherein the second complementary sequence is complementary to the second target sequence of the target polynucleotide; incubating the first and second complementary polynucleotides with the sample under conditions that allow hybridization of the first and second complementary sequences of the first and second complementary polynucleotides with the first and second target sequences of the target polynucleotide (if present); if the first complementary polynucleotide and the second complementary polynucleotide are hybridized to the same target polynucleotide, then joining the first complementary polynucleotide to the second complementary polynucleotide, to form a first product polynucleotide; and detecting the presence of the target polynucleotide by generating sequence data that directly or indirectly determines the sequence of the first product polynucleotide, or detecting the absence of the target polynucleotide in the sample by not determining the sequence of the first product polynucleotide.

In various embodiments, the term LHS refers to an example of a first complementary polynucleotide, and the term RHS refers to an example of a second complementary polynucleotide. It will be recognized that the first or second complementary polynucleotides can be either LHS or RHS sequences, in that they can be interchanged, and or hybridize to the opposing target DNA strand.

In some cases the presently disclosed method may further include a polymerization step, digestion step, or repair step before or within the joining step. In some cases the polymerization step can comprise elongating the first and/or second complementary polynucleotides. In some cases, the digestion step can include digestion of the first and/or second complementary polynucleotides. In some cases, the repair step may include repair of the first and/or second complementary polynucleotides. In some cases a polymerization and/or repair step can be performed where the first and second complementary polynucleotides are hybridized to the same target polynucleotide, and the 5' end of one complementary polynucleotide is separated from the 3' end of the other polynucleotide by one or more nucleotides. In another embodiment, the first and second complementary polynucleotides can be linked via a third molecule. The third molecule can be DNA, RNA or a nucleic acid analog such as PNA or LNA. The third molecule can hybridize to the target polynucleotide sequence-specifically, or in between the first and second complementary polynucleotides. The third molecule can be joined to each of the first and second complementary polynucleotides by any of the methods described for joining the first and second complementary polynucleotides to form a product polynucleotide.

Polynucleotides, including but not limited to complementary polynucleotides or target polynucleotides, are polymeric form of nucleotides or nucleotide analogs of any length, including deoxyribonucleotides or ribonucleotides, or analogs thereof, or mixtures thereof. Polynucleotides may contain modified bases, including those that include, without limitation, a methylation, deaniination, deamination, thiolation, and/or acetylation. A polynucleotide may be further modified before or after polymerization, such as by conjugation with a labeling component. The polynucleotide may be an amplified region of a longer sequence of nucleotides. A polynucleotide may be a peptide nucleic acid (PNA), locked nucleic acid (LNA), Armored RNA, nucleic acids with phosphoric background modifications (e.g. bridging chiral phosphorothioates, non-bridging chiral phosphorothioates, phosphorodithioate, chiral methyl phosphonate, chiral phosphoramidate, chiral phosphate trimester, chiral boranophosphate, and chiral phosphoroselenoate. Exemplary linkage modifications include methylenemethylimino (MMI), 3'-amide, 3' achiral phosphoramidate, 3' archiral methylene phosphonate, thioformacetal, and thioethyl ether modifications. Exemplary sugar modifications include 2'-fluoro, 2'-O-methyl, 2'-O-(3-amino)propyl, 2'-O-(2-methoxy)ethyl, 2'-O-2-(N,N-dimethylaminooxy)ethyl (DMAOE), 2'-O-2-[2-(N,N-dimethylamino)ethyloxy]ethyl (DMAEOE)3 and 2'-O—N,N-dimnethylacetarnidyl. Classes of analog nucleotides having sugar modifications include N-morpholinophosphordiamidate (Morpholinos); hexose nucleic acid (HNA); threose nucleic acid (TNA), such as those disclosed in Chaput et al., AMER. CHEM. SOC, 125:856-857 (2003); cyclohexene nucleic acid (CeNA); locked nucleic acid (LNA), having methylene bridges between the 2'-O and 4'-C on the ribofuranose ring of some or all individual nucleotides of a polynucleotide (which methylene bridges function to restrict the flexibility of the polynucleotide and are associated with enhanced stability and hybridization characteristics), such as those disclosed in TRENDS IN BIOTECHNOLOGY 21:74-81 (2003); and tricycle-deoxyribose nucleic acid (tcDNA) modifications. Base modifications include 5-propynyluracil-1-yl, 5-methylcytosin-1-yl, 2-aminoadenin-9-yl, 7-deaza-7-iodoadnin-9-yl, 7-deaza-7-propynyl-2-aminoadenin-9-yl, phenoxazinyl, phenoxazinyl-G-clamp, 2,6-diamino purine, and 2,6-diamino thiouracil. A preferred connection modification is an α-deoxyribofuranosyl.

It will be understood that the polynucleotide Includes polynucleotides that are covalently or non-covalently linked to another molecule. For example, polynucleotides can be bonded to a protein, biotin, or avidin functionality.

A complementary polynucleotide is one in which a single-stranded polynucleotide has the ability to bind a polynucleotide in a base-specific manner. A polynucleotide that is "complementary" may have one or more single base-pair mismatches, additions, and/or deletions, but is still capable of hybridizing to the target polynucleotide under the selected hybridization or association conditions. An exactly complementary polynucleotide has the ability to hybridize to a target nucleic acid sequence without base mismatches. A polynucleotide is not exactly complementary to a target polynucleotide if there is a single base-pair mismatch between the polynucleotide and the target polynucleotide.

Hybridization of polynucleotides can be performed under various conditions known in the art. For example, hybridization can occur under various stringency conditions. Stringency refers to the binding of two single stranded polynucleotide sequences via complementary base pairing. Extensive guides to the hybridization of nucleic acids can be found in: Tijssen, Laboratory Techniques in Biochemistry and Molecular Biology-Hybridization with Nucleic Acid Probes Part I, Ch. 2, "Overview of principles of hybridization and the strategy of nucleic acid probe assays" (1993), Elsevier, N.Y.; and Sambrook et al., Molecular Cloning: A Laboratory Manual (3rd ed.) Vol. 1-3 (2001), Cold Spring Harbor Laboratory, Cold Spring Harbor Press, N.Y.

Stringent conditions are hybridization conditions under which a polynucleotide will hybridize preferentially to its target subsequence, and optionally, to a lesser extent, or not at all, to other sequences in a mixed population (e.g., a DNA preparation from a tissue biopsy).

Generally, highly stringent hybridization and wash conditions are selected to be about 5° C. lower than the thermal melting point (Tm) for a specific sequence at a defined ionic strength and pH. The Tm is the temperature at which 50% of the target sequence hybridizes to a perfectly matched probe. Very stringent conditions are selected to be equal to the Tm for a particular probe. Often, a high stringency wash is preceded by a low stringency wash to remove background probe signal. An example of stringent hybridization conditions for hybridization of complementary nucleic acids which have more than 100 complementary residues on an array is 42° C. using standard hybridization solutions, with the hybridization being carried out overnight. An example of highly stringent wash conditions is a 0.15 M NaCl wash at 72° C. for 15 minutes. An example of stringent wash conditions is a wash in 0.2× Standard Saline Citrate (SSC) buffer at 65° C. for 15 minutes. An example of a medium stringency wash for a duplex of, for example, more than 100 nucleotides, is 1×SSC at 45° C. for 15 minutes. An example of a low stringency wash for a duplex of, for example, more than 100 nucleotides, is 4× to 6×SSC at 40° C. for 15 minutes.

In some cases the joining step may comprise covalent bonding or non-covalent bonding of the first and second complementary polynucleotides.

Joining of the complementary polynucleotides covalently can result in a covalently-bonded product polynucleotide. An example of one way of covalent joining is ligating the first and second complementary polynucleotides to form a product polynucleotide. Without each terminal base hybridized to the target polynucleotide, the complementary polynucleotides do not ligate to form a product polynucleotide.

In one embodiment, a covalent product polynucleotide can be created by template-directed chemical ligation of natural 5' phosphorylated and 3' hydroxyl DNA polynucleotides catalyzed by cyanogen bromide (BrCN). First and second complementary polynucleotides can be hybridized onto the target polynucleotide. The first and second complementary polynucleotides are joined by the 5'-3' phosphate link. The product polynucleotide has full biological functionality. An example of such a non-enzymatic joining is described, for example, in Shabarova et al., Nucleic Acids Res. 1991 Aug. 11; 19(15):4247-51.PMID:1870979.

In another embodiment, joining can be performed by template-directed ligation. For example, a first complementary polynucleotide is modified by a 5'-iodo group and a second complementary polynucleotide is modified by a 3' phosphorothioate group. The first and second complementary polynucleotides are joined to form a product polynucleotide. In various embodiments, the reaction requires no reagents other than the modified polynucleotides and the target polynucleotide. The reaction can show some mismatch discrimination at the ligation site, and even higher mismatch discrimination if the mismatch is positioned 3-4 bases away from the ligation site. This joining by non-enzymatic ligation results in a phosphorothioate-containing DNA, which is resistant to nucleases but is a good template for DNA and RNA polymerases. An example of such a reaction is disclosed by Xu Y, Kool E T. Nucleic Acids Res. 1999 Feb. 1; 27(3):875-81.PMID:9889286.

In one variation, the first complementary polynucleotide is modified with a 5' dabsyl leaving group, and the second complementary polynucleotide is modified with a 3' phosphorothloate. The first and second complementary polynucleotides are joined by non-enzymatic ligation that requires no other reagents besides the modified first and second complementary polynucleotide and the target polynucleotide. Ligation is target polynucleotide-dependent, and can be performed in *E. coli* cells or outside of cells. The product polynucleotide is fluorescently de-quenched by the removal of the dabsyl such that the product polynucleotide can be detected by a fluorescence increase in vivo or in vitro. The product polynucleotide is natural DNA and can be used by polymerases and DNases. An example reaction is described in Sando S, Kool E T. Nucleic Acids Res Suppl. 2002; (2):121-2.PMID:12903135.

In another embodiment, first and second complementary polynucleotides are joined by template-directed ligation. The first complementary polynucleotide has a modified 5' 5-vinyldeoxyuridine and the second complementary polynucleotide has a 3'-terminal pyrimidine (a T or C base). The first and second complementary polynucleotides are photo-ligated by a [2+2] cyclobutane dimer formation between the vinyl group on the 5' complementary polynucleotide and the 5-6 C—C double bond on the pyrimidine on the 3' complementary polynucleotide. The bond can resemble a UV-induced DNA damage product. The product polynucleotide is nuclease resistant. The reaction can be reversed upon irradiation with 302 nm light. An example reaction described in Fujimoto K, Matsuda S, Saito I. Nucleic Acids Symp Ser. 1999; (42):39-40.PMID:10780368.

In another embodiment, the complementary polynucleotides are joined by non-enzymatic click-chemistry-based ligation. The first complementary polynucleotide is modified with a 5' alkyne group. The second complementary polynucleotide is modified with a 3' azide group. The joining step requires a Cu(I) catalyst or another suitable catalyst. An example of such a reaction is described by Kumar R, El-Sagheer A, Tumpane J, Lincoln P, Wilhelmsson L M, Brown T. J Am Chem Soc. 2007 May 30; 129(21):6859-64. Epub 2007 May 9.PMID:17488075.

In certain embodiments, a non-covalent method of joining to produce a product polynucleotide is envisioned. In one non-limiting example, first and second complementary polynucleotides can be non-covalently joined by making a 3' biotin-labeled first complementary polynucleotide, in which the biotin end is sterically blocked by the formation of a 3' end hairpin, and a second complementary polynucleotide that is modified with streptavidin at the 5' end. The 3' biotin-labeled first complementary polynucleotide is non-covalently joined to the 5' labeled streptavidin second complementary target polynucleotide in the presence of a target polynucleotide. The target polynucleotide can serve to (i) unravel the biotin-blocking hairpin and/or (II) bring the biotin-labeled and streptavidin-labeled complementary polynucleotides in close proximity such that they can be non-covalently joined.

In various other embodiments, the biotin is on the second complementary polynucleotide and the streptavidin is on the first complementary polynucleotide. In further embodiments, the first and second complementary polynucleotides have non-biotin and non-streptavidin portions that are involved in the non-covalent joining.

In another embodiment, the first and second complementary polynucleotides can be joined non-covalently by the use of a specific antibody-antigen pair, where one of the complementary polynucleotides is labeled at its 5' end with an antigen and the other complementary polynucleotide is labeled at the 3' end with a specific antibody for the antigen. Either the antibody binding site or the antigen is blocked by a photo-cleavable moiety which prevents the binding between antigen and antibody. Upon hybridizing the two complementary polynucleotides to the target polynucleotide, the un-bound complementary polynucleotides are removed (for example by gel purification or other methods). The blocking moiety is released by irradiation with the correct wavelength and the first and second complementary polynucleotides are joined non-covalently by the specific antigen-antibody interaction.

It will be appreciated that for purposes of detecting polymorphism, the polymorphism need not occur at the terminal base of the first complementary polynucleotide or second complementary polynucleotide (at its first base) depending on the method of joining. It will be appreciated by those of skill in the art that the first and second complementary polynucleotides descriptions herein can be in reverse order.

In some cases, the presently disclosed method may further include an enriching step before the determining step. The enriching step may increase the ratio of product polynucleotides to non-product polynucleotides. In some cases, the enriching step may comprise selecting the product polynucleotides by size, affinity, charge, sequence, or a combination thereof. In some cases the enriching step may comprise amplification of the product polynucleotide. In other cases the enriching step may comprise removal of some or all of the non-product polynucleotides, for example by size, sequence, selection, segregation, or digestion or a combination thereof. In various cases, the enriching step may combine selection of the product polynucleotide and removal of non-product polynucleotides. In some variations, the joining and enrichment steps can occur in a single reaction mixture. In other variations, the joining and enrichment steps can occur in different reaction mixtures.

In this variation, the first products are enriched by labeling either or both the first and second complementary polynucleotides with a 5' Biotin or 3' Biotin label, respectively. After joining the first and second complementary polynucleotides, streptavidin coated paramagnetic beads are added to bind the biotin. The biotin containing polynucleotides/streptavidin beads are washed to remove non-biotin containing elements. This enriches the for the first product polynucleotide. A silica column based purification may be included to size fractionate the non-joined first and second complementary polynucleotides from those that did join. In other variations, single stranded DNases could be added and the first and second complementary polynucleotides removed by digestion. Only those that are joined due to the hybridization with the target polynucleotide are in a double stranded form and protected. In other variations, the first and second complementary polynucleotides each have a single end protected from exonuclease digestion. When they are joined, both ends are protected. In this manner the addition of an exonuclease removes the non-joined first and second complementary polynucleotides.

In some cases, the first and/or second complementary polynucleotides may comprise tag sequences. In various cases, the tag sequences may aid in identifying the sample and/or target sequences and/or variations (polymorphisms) in the target sequence. In various embodiments, the tag sequences may allow the sample and/or target sequences and/or variations (polymorphisms) to be determined without generating sequence data on the target sequences. The tag sequences can be positioned 5' of a LHS or 3' of the RHS. In some variations various tag sequences can occur on or be added to the first and/or second complementary polynucleotide. In some variations portions of a tag sequence may occur on one, or both, of the first and second complementary polynucleotide.

In some cases, a tag sequence may be more than about 1 nt, 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, or 21 nt, or the tag sequence may be less than about 30 nt, 29 nt, 28 nt, 27 nt, 26 nt, 25 nt, 24 nt, 23 nt, 21 nt, 20 nt, 19 nt, 18 nt, 17 nt, 16 nt, 15 nt, 14 nt, 13 nt, 12 nt, 11 nt, 10 nt, or 9 nt.

In some variations of the present method, the method can be used for identifying the presence or absence of a plurality of different target polynucleotides. In these embodiments, there may be a plurality of first and second complementary polynucleotides for hybridizing to the plurality of different target polynucleotides, wherein the plurality of first and second complementary polynucleotides comprise sets of first and second complementary polynucleotides. For example, in variations of the method for identifying the presence or absence of a first target polynucleotide and a second target polynucleotide, there may be a first set of first and second complementary polynucleotides and a second set of first and second polynucleotides. In these cases the first set of first and second polynucleotides may have complementary sequences that can hybridize to the first and second target sequences of the first target polynucleotide, and the second set of first and second polynucleotides may have a first and a second complementary sequence that can hybridize to the first and second target sequence of the second target polynucleotide. In some variations, a sample may or may not comprise more than two target polynucleotides. In these cases, the method may further comprise more than one set of complementary polynucleotides.

In some variations, the method may further comprise a pooling step after the joining step. In these cases, product polynucleotides from various samples are combined to create a pool or library of product polynucleotides, which can then be submitted for sequencing. This can allow the determination of various product polypeptide sequences from multiple samples at the same time. For example, where sequence determination is performed by Illumina sequencing, the various product polynucleotides are sequenced in a single lane of a flow cell. In these cases, the first and/or second complementary sequences can comprise a sample-specific tag. In some cases, the sample-specific tag may be added to a product polynucleotide, for example by ligation, or during an enrichment step, such as during amplification.

In some cases, for example where a sample may or may not comprise a plurality of different target polynucleotides, such as embodiments wherein the target polynucleotides comprise different gene sequences or different genetic loci, the first and second complementary polynucleotides may comprise locus-specific tags. In some cases, the method can be used to determine the presence or absence of a signature polynucleotide sequence and as such determine the presence or absence of a pathogen in a sample.

In some variations, the presently described method can be used to identify polymorphisms such as, but not limited to, single and multi-nucleotide polymorphisms, deletions, insertions, translocations, covalent nucleotide modifications, etc. In various cases, the target polynucleotide can be derived from samples of animal, plant, microbial, viral, or synthetic DNA or RNA. In some cases, the method can be used to genotype or fingerprint a sample.

In variations for identifying target polynucleotides with polymorphic nucleotides and nucleotide sequences, the method can involve hybridizing two first complementary polynucleotides to a target polynucleotide, wherein the target polynucleotide includes a polymorphic nucleotide. In some of these cases, one of the two complementary polynucleotides can comprise a nucleotide that is complementary to one form of the polymorphic nucleotide on the target polynucleotide. If the polymorphic nucleotide on the complementary polynucleotide hybridizes to the polymorphic nucleotide on the target polynucleotide, the two complementary polynucleotides can be joined together to create a product polynucleotide. If the polymorphic nucleotide on the complementary polynucleotide does not hybridize to the polymorphic nucleotide on the target polynucleotide, the two complementary polynucleotides, in most cases, cannot be joined and cannot form a single product polynucleotide. In most cases, the product polynucleotides are sequenced to determine the presence or absence of the polymorphism, and the identity of the target polynucleotide. In some variations, the identity of the sample from which the target polynucleotide was derived is also determined by sequencing.

In some variations of the presently described method, more than one set of a first and a second complementary polynucleotide may be used. In these cases, the method can be used to distinguish or identify multiple polymorphisms at a given target sequence, for example where a target represents a gene locus or allele. In some variations multiple loci can be characterized from a single sample to provide the identity of polymorphic nucleotides in various target polynucleotides. In some variations of the present method, multiple samples can be genotyped or fingerprinted.

Variations of the present method can be used to identify alleles of a single nucleotide polymorphism (SNP) in a target polynucleotide sequence. As shown in FIG. 1, a SNP is a single nucleotide in a given sequence that may have several identities. For example, a SNP at a given position may be a thymine in one sample, while in another sample that same nucleotide position is a cytosine. In some cases, for example where samples are derived from genomic DNA, for example from a diploid mammal with two copies of a given SNP, the SNP could be homozygous or heterozygous.

In variations of the present method for analysis of diploid genomic DNA samples, multiple different complementary polynucleotides, which differ in the identity of their polymorphic nucleotide, may be used to interrogate a target polymorphism.

Exemplary FIG. 1 depicts a variation of the present method to analyze target polynucleotides from two samples, Sample 1 and Sample 2. The samples depicted in FIG. 1 are derived from a diploid organism, and thus comprise two copies (or alleles) of each target polynucleotide. Further, each sample includes two different target polynucleotide sequences at each target polynucleotide. That is there are two loci (Locus A and Locus B) and each locus has two alleles, Allele A and Allele B. In this illustration, Locus A can have either a thymine, "T," or guanine, "G," on one strand at the polymorphic nucleotide. Locus B can have a cytosine, "C," at the polymorphic nucleotide or a thymine, "T."

As depicted in FIG. 1A, Locus A of Sample 1 is homozygous for the T allele, $A_T/A_T$, while Locus A of Sample 2 is heterozygous, $A_G/A_T$. Locus B of Sample 1 is heterozygous, $B_C/B_T$, while Locus B of Sample 2 is homozygous for the T allele, $B_T/B_T$.

While either strand of a polymorphic locus can be analyzed for a given polymorphism, for ease of illustration, the bottom strand in FIG. 1A is analyzed. The analyzed target polynucleotide is shown in FIG. 1B without the top strand. The target polynucleotide is shown 3'->5' (reading left to right).

FIG. 1B shows target polynucleotides after denaturation of the duplex DNA of FIG. 1A. The target polynucleotides are comprised of two target sequences: a first target sequence 3' of the polymorphic nucleotide, and a second target sequence 5' of the polymorphic nucleotide. After denaturation, the target polynucleotides are mixed with a plurality of complementary polynucleotides, and the target polynucleotide and complementary polynucleotides allowed to hybridize.

Complementary polynucleotides are depicted in FIG. 1C hybridized to target polynucleotides. For each target polynucleotide there are at least two complementary polynucleotides, which hybridize to the first target sequence and the second target sequence. The first complementary polynucleotide is complementary to and can hybridize with the first target sequence on the target polynucleotide. In some variations, the first target sequence is on the left side of the polymorphic nucleotide, and the first complementary polynucleotide can be referred to as a left hybridization sequence ("LHS"). Likewise, the second complementary polynucleotide, which can hybridize to the second target sequence, can be referred to as a right hand sequence ("RHS").

Referring now to FIG. 2, the first complementary polynucleotide comprises a first complementary sequence, or hybridization sequence, which is complementary to the first target sequence on the left (3') side of the polymorphic nucleotide (polymorphism) of the target polynucleotide. The first complementary polynucleotide further comprises a 3' terminal nucleotide that can be complementary to the polymorphic nucleotide on the target polynucleotide. The second complementary polynucleotide comprises a second complementary sequence, or hybridization sequence, which is complementary to the second target sequence on the right (5' side) of the polymorphic nucleotide (polymorphism) of the target polynucleotide. Alternatively, it will be appreciated that the second complementary polynucleotide may comprise a 5' terminal nucleotide that can be complementary to the polymorphic nucleotide on the target polynucleotide. The first complementary polynucleotide comprises a first complementary sequence, or hybridization sequence, which is complementary to the first target sequence on the left (3' side) of the polymorphic nucleotide (polymorphism) of the target polynucleotide.

FIG. 2A depicts a single stranded target sequence (bottom) and two polynucleotides, a first complementary polynucleotide and a second complementary polynucleotide (top), hybridized to the target sequence. The target sequence includes a polymorphic nucleotide depicted in bold. The target sequence, as in FIG. 1, is shown in a 3' to 5' orientation. The first complementary polynucleotide and second complementary polynucleotide are shown above the target sequence. Both the first complementary polynucleotide and the second complementary polynucleotide comprise a target complementary sequence, which are complementary to target sequence on the left and right of a polymorphism in the target sequence. The first complementary polynucleotide further comprises a 3' terminal nucleotide (also bold) that is complementary to the target polymorphism.

FIG. 2B depicts other possible first complementary polynucleotides for use with other alleles of the target sequence depicted in FIG. 2A. These first complementary polynucleotides are labeled (I)-(Iv).

Because FIG. 1 depicts a method for investigating two loci, two different second complementary polynucleotides, designated RHS A and RHS B, specific for the two loci, Locus A and Locus B, are shown.

Because Locus A and Locus B each have two alleles, there are two first complementary polynucleotides for Locus A, LHS-T (this is equivalent to LHS.$A_T$) and LHS-G (this is equivalent to LHS.$A_G$), and two first complementary polynucleotides for Locus B, LHS-C (this is equivalent to LHS.$B_C$) and LHS-T (this is equivalent to LHS.$B_T$).

FIG. 1C shows that only the LHS-T first complementary polynucleotide hybridizes to the target polynucleotide of Sample 1. The LHS-G first complementary polynucleotide cannot be joined to the second complementary polynucleotide, because the terminal base of the LHS-G does not hybridize to the corresponding base of the target polynucleotide in Sample 1. However both Locus B first complementary polynucleotides, LHS-C and LHS-T, have terminal bases that hybridize to the corresponding base in target polynucleotides of Sample 1. Regarding Sample 2, both Locus A first complementary LHS polynucleotides, LHS-T, and LHS-G, hybridize to the corresponding base of the Sample 2 target polynucleotide, but only the LHS-T terminal base of the first complementary polynucleotide hybridizes to the corresponding base of the Sample 2 target polynucleotides. In the embodiment of the ligase mediated joining, this differential hybridization of the terminal base of the first complementary polynucleotide allows the ligase to preferentially join one of the first complementary polynucleotides.

In many variations of the presently described method, the number of first complementary polynucleotides can correspond to the number of possible polymorphisms, polymorphic nucleotides, or alleles at a given locus. As described above, because the loci depicted in FIG. 1 have two alleles each, there are two corresponding first complementary polynucleotides for each locus in this example (Locus A with LHS-T, and LHS-G, plus Locus B with LHS-T, and LHS-G). In other variations there can be more than two first complementary polynucleotides for a given locus. In variations wherein a single base SNP is interrogated, there can be as many as four first complementary polynucleotides for a given locus, as depicted in FIG. 2B. Multi-nucleotide polymorphisms can have more than four first complementary polynucleotides for a given locus.

In many variations there is a single second complementary polynucleotide for a given locus. Thus, FIG. 1C shows two complementary polynucleotides, one for locus A called RHS-A and another for locus B called RHS-B. In some variations there can be more than one second complementary polynucleotide for a given locus. In many variations, the second complementary polynucleotide Includes a 5' phosphorylated nucleotide. This phosphate moiety can aid in allowing ligation of the first and second complementary polynucleotides.

FIG. 1C depicts a locus LHS-G polynucleotide unhybridized to Sample 1 target DNA, and a locus LHS-C polynucleotide unhybridized in Sample 2. In some cases first complementary polynucleotides with 3' nucleotide sequences that are not complementary to a polymorphic sequence on a target polynucleotide can hybridize to the target polynucleotide, but as discussed below, in most cases these non-complementary first complementary polynucleotides will not be joined to the second complementary polynucleotide and/or result in a small portion of the product polynucleotides produced. Non-complementary first complementary polynucleotides that are joined to a second complementary polynucleotide represent false positives.

As depicted in FIGS. 1C and 2A, a first complementary polynucleotide with a 3' nucleotide that is complementary to the polymorphic nucleotide can hybridize to the target DNA sequence, while first complementary polynucleotides with 3' nucleotides that are not complementary to a polymorphic nucleotide sequence on a target polynucleotide will usually not be joined.

In many variants of the presently disclosed method, the length of the first and second complementary sequence of the first and second complementary polynucleotide can be varied relative to various criteria, for example the melting temperature of the duplex, ionic strength of hybridization solution, complexity of the target sequence (as discussed more below, mammalian genomic target sequence can require longer target complementary sequences than viral target DNA or synthetic target DNA, RNA, PNAs, LNAs), etc.

After hybridization of the first complementary polynucleotide and second complementary polynucleotide to the target DNA sequences, the first and second complementary polynucleotides are joined.

Where enzymatic ligation is used to join the first and the second complementary polynucleotides, the first complementary polynucleotide and second complementary polynucleotide for a given locus can be ligated by connecting the 3' terminal hydroxyl (OH) of the first complementary polynucleotide to the 5' phosphate ($PO_4$) of the second complementary polynucleotide. Successful ligation creates a single product polynucleotide, depicted at FIG. 1D. Again, in some cases, a first complementary polynucleotide with a 3' terminal nucleotide that is not complementary to a polymorphism on the target polynucleotide can be ligated to a given second complementary polynucleotide. This can represent a false positive. In other methods of joining, such as non-enzymatic chemical joining of iodo compounds, the polymorphic nucleotide or nucleotides do not need to be at the terminal base or bases.

In some variations of the presently described method, the product polynucleotides may be enriched. In these cases, enrichment may be done by amplification. The product polynucleotide can be amplified, for example, by PCR (polymerase chain reaction). The product polynucleotides can also be sequenced, after, or in some cases, before being amplified. In some variations, other amplifications methods may be used, including but not limited to loop-mediated isothermal amplification, transcription mediated amplification, branched DNA and ligase chain reaction. It will be understood that the product polynucleotide can be an enriched polynucleotide, such as an amplification product.

In some variations wherein the method comprises an enrichment step, and enrichment comprises amplification by PCR, PCR primers can be used to amplify the product polynucleotides. The PCR primers may comprise one or more and tag sequences, and a sequence that is complementary, or identical, to a sequence on the product polynucleotide. In many variations a first PCR primer may anneal to the product polynucleotide at or near the 3' end of the product polynucleotide. A polymerase can be used to elongate the first PCR primer, resulting in a first amplification polynucleotide comprising a first sequence of the first PCR primer and a second sequence that is complementary to the product polynucleotide. A second PCR primer may then anneal to the first amplification polynucleotide at or near its 3' end. Elongation of the second PCR primer results in a second amplification product comprising a first sequence of the second PCR primer and a second sequence that is complementary to the first amplification polynucleotide. Annealing the first PCR primer to the second amplification polynucleotide at or near its 3' end, and elongating the first PCR primer can result in a third amplification polynucleotide that is complementary to the second amplification polynucleotide.

In some variations, the first and/or second PCR primers can include tag sequences. The tag sequences can aid in identifying the sample from which the amplification products were obtained, and can add sequences necessary for subsequent sequencing. Tag sequences for use in identifying the sample's origin may be referred to as a sample-specific tag. For example, in one variation, the PCR primers may add Illumina sequences for aid in capturing amplified polynucleotides onto the Illumina flowcell for bridge amplification. In other variations, the PCR primers may add sequences for compatibility with other sequence data generation methods.

In some variations the first complementary polynucleotide and/or second complementary polynucleotide can further comprise tag sequences. For example, identification of a locus, and/or identification of the polymorphic nucleotide. In other variations, the identity of the locus and/or polymorphic nucleotide may be determined, directly, by sequencing through the product polynucleotide. In various embodiments, linker or adaptor sequences that can allow for annealing of PCR primers or processes involved in sequence generation can be added. Tags can be used to determine specific information, and linkers and adaptors can be used as a component of physical, chemical, or enzymatic processes.

Tag sequences for use in annealing of PCR primers can be referred to as amplification tag sequences, or PCR Tags (FIG. 2C). PCR tags can allow PCR primers to anneal to the polynucleotide. In other variations, PCR primers can anneal to target complementary sequences in the first and second polynucleotides, and/or to other sequences, for example a locus specific tag sequence, discussed below.

In some variations of the presently disclosed method, the complementary polynucleotides may further comprise a tag sequence for identification of the locus. The first complementary polynucleotide and/or second complementary polynucleotide can comprise a locus-specific tag sequence 5' or 3', respectively, of the target complementary sequence. FIG. 2D depicts the first complementary polynucleotide and second complementary polynucleotide of FIG. 2A with locus-specific tags. In most cases wherein the first complementary polynucleotide has a locus-specific tag, all first complementary polynucleotides that are specific for a given locus will have an identical locus-specific tag. The locus-specific tag can be any length, for example more than six, seven, eight, nine, ten, eleven, twelve, thirteen, fourteen, or fifteen nucleotides in length. As described herein, the identity of the locus may also be directly determined by sequencing through one or more of the tag sequences, product polynucleotide, complement of the product polynucleotide, and/or amplification product of the product polynucleotide.

In some variations the first complementary polynucleotide can comprise a polymorphism-specific tag sequence 5' of the complementary sequence. FIG. 2E depicts the first complementary polynucleotides of FIG. 2B with polymorphism-specific tags (i, ii, iii, iv). The polymorphism specific tags for each first complementary polynucleotide at a given locus will differ in their respective 3' nucleotides and their polymorphism-specific tags. In some variations, the polymorphism specific tag can be one, two, three, four, five, or more nucleotides. As described above, the identity of the polymorphism can also be obtained, directly, by sequencing through the complementary sequences of the first or second complementary polynucleotide to the polymorphic nucleotide. It will be appreciated that the second complementary polynucleotide can contain the polymorphic nucleotide on its 5' side, which must be 5' phosphorylated, and that such second complementary polynucleotides would then contain polymorphism specific tags on their 3' ends.

In some cases, PCR primers can be used to aid in amplification of the product polynucleotides. In some variations, one or both PCR primers for a given sample or individual can further comprise a sample-specific (or individual-specific) sequence tag. In cases where loci from multiple samples or individuals can be sequenced together, each sample can first be amplified separately, wherein a sample-specific tag sequence is included in the first and/or second PCR primer, wherein the sample-specific tag sequence and/or combination of sample-specific tag sequences is a unique identifier of the origin sample. Each product polynucleotide from a given sample can have a common sample-specific tag or tags, as wherein both PCR primers include a sample specific tag. In some cases, wherein both PCR primers comprise a sample specific tag, the tag sequences may be the same or they may differ. Sample-specific tags can be one, two, three, four, five, six, seven, eight, nine, ten, or more nucleotides.

Tagging amplified products with sample-specific tags can allow product polynucleotides from various samples to be combined, and sequenced together. In these cases, the identity of the individual or sample can be obtained by sequencing the sample-specific sequence tag or tags of each product polynucleotide.

FIG. 3 is a diagram of first complementary polynucleotide and second complementary polynucleotide for use in one variation of the present method to genotype based on SNP identification and Illumina sequencing where the sample specific tags are part of the complementary polynucleotides and no PCR enrichment is involved. The Illumina FC A and FC B are Illumina fixed sequences and are required in order to anneal to the Illumina flow cell. Sample specific tags that were present in the first and second PCR primers to aid in identifying the sample in the PCR based method are now directly Incorporated into the LHS and RHS probe sequences, and as such no PCR is required. The Illumina PCR 1 and 2 are Illumina fixed sequences were required for PCR amplification of the product polynucleotides and are the locations of (and still used for), the Illumina specific sequencing primers in the Illumina flow cell. The polymorphism-specific tag is unfixed and can be any tag to spell out any of the four nucleotide possibilities. The first complementary polynucleotide and second complementary polynucleotide vary according to the locus being interrogated.

In some variations sequencing Is performed by next generation sequencing. There are several common platforms currently in use.

In some variations, the next generation sequencer is 454 technology developed by Roche. 454 technology uses microbeads to which DNA fragments are captured and clonally amplified by emulsion PCR (emPCR). In various permutations, each bead contains a large number of identical copies of the parent DNA sequence. The beads are deposited on a chip containing multiple wells, with each well containing only one template bead. Each well is addressed by a fiber optic for signal acquisition. 454 technology uses pyrosequencing in which individual nucleotides are flown over the beads containing the clonally amplified DNA fragments, and the template-directed incorporation of a given nucleotide is detected by an enzymatic cascade. The enzymatic cascade uses the pyrophosphate (by-product of base incorporation) to generate a light signal. The light signal intensity is proportional to the number of bases incorporated, such that short homopolymers can be reliably identified. After a wash, the process is repeated with each of the remaining NTPs, and the sequence of each DNA fragment is determined from the pattern of light signals produced by each bead. 454 sequencing technology has a read length of 400-600 bases, usually of unequal length. It has around 1M reads per run, does not perform paired reads, and requires approximately 10 hours.

454 sequencers use natural NTPs, and are regarded to have long read length, short run time, high accuracy. They also have complicated sample preparation (e.g. emPCR); low number of reads, and reads of unequal length.

Another example of next generation sequencing is SOLiD (Sequencing by Oligonucleotide Ligation and Detection) (Applied Biosystems). SOLID uses microbeads to which DNA fragments are captured and clonally amplified by emPCR. The beads are then covalently bound on a glass slide and are microscopically imaged during sequencing. SOLiD technology uses sequencing-by-ligation, in which positions at increasing distance from the end of the molecule are probed with fluorescently-labeled ligation probes. Each probe has two discriminating bases at the end, and each position in the template to be sequenced is probed twice (once at the first position of a ligation probe, then again at the second position of the next ligation probe).

SOLID sequencing slides can be divided in 4 or 8 sections and separate samples can be loaded on each section, increasing the number of samples that can be run at once. Current SOLiD technology can generate up to 100 Gb of sequence data per run, with a run time of up to 16 days. SOLiD technology generates reads of equal lengths, and it can produce paired end reads. Read length is limited to 2×50 bases for paired end reads and to 60 bases for single end reads. The system can perform up to 1.4 billion reads with microbeads and up to 2.4 billion reads with nanobeads. A run time can take 16 days for 50×50 reads. The system is capable of high throughput, highest accuracy, the possibility of obtaining of paired reads, and has a modular design of the sequencing substrate (slides). The system has complicated sample prep (e.g. emPCR), limited read length, long run time, and results are provided in color space-instead of sequence-space.

Another exemplary next-generation sequencer is provided by Illumina (also known as Solexa technology). Solexa relies on capture primers covalently attached to the surface of glass flow cells, which are used to capture and clonally amplify DNA fragments for sequencing. The clonal amplification occurs on the surface by a process called 'bridge PCR' in which one parent molecule generates a cluster of identical sequences. Illumina technology uses 'sequencing by synthesis' in which fluorescently-labeled, chain-terminating nucleotides are incorporated one at a time in a template-dependent order. After each cycle, the glass surface is microscopically imaged and 4 color pictures are taken, and the base that was incorporated into each cluster is determined; the dye and chain terminator group are removed before the next cycle. The location of each cluster is kept constant for all the cycles.

The Illumina method has a read length of 100 bases (HiSeq), 150 bases (GAIIx or MiSeq), 300 bases, 400 bases or more. It can perform up to 600 Million reads/run (GAIIx) or 3 Billion reads/run (HiSeq) or 5 Million reads/run (MISeq), and is capable of paired-end reads. The approximate run time is 14 days for 2×150 reads. The Illumina method has simple sample preparation, relatively long reads, the possibility of obtaining paired-end reads, and includes a modular design of sequencing substrate (lanes on flow cell). The system also has a comparatively long run time.

Other next generation sequencing platforms include Complete Genomics, which uses DNA nanoball sequencing technology in combination with proprietary software to determine the complete genome of submitted samples. The technology is optimized for human genome sequencing projects. The company offers DNA sequencing as a service, and the sequencers are not commercially available.

Pacific Biosciences uses another NGS platform that uses single molecule real time sequencing technology for gene sequencing. The technology in its current form generates very long reads (average 750 bp, longest reads up to 6 kb), but the number of reads is limited (~20 k).

Ion Torrent is another exemplary NGS sequencing platform that uses a technology similar to the 454 technology, with the difference that the Incorporated base Is detected by a change in pH as opposed to an enzymatic cascade. Ion Torrent technology currently generates reads of about 100 bases, and up to 1 M reads per run, with a run time of ~2 h. Significant improvements of both read length and throughput are expected for this technology.

Helicos is another NGS sequencing platform that uses true single molecule sequencing (tSMS) technology, in which the template DNA strands are captured on a glass surface by covalently attached capture primers, and are sequenced by the stepwise addition of fluorescently labeled nucleotides, one at a time. The glass surface is imaged after the addition of each base, and the location of each newly incorporated base is recorded. The fluorescent group is then cleaved and the next base is added. Helicos technology can generate billions of reads per run, but the read length is currently limited to about 25 bases.

Target Polynucleotides

The presently described method can be used for detecting the presence or absence of a target polynucleotide. In some cases, the target polynucleotide may be DNA and/or RNA. In some cases, the method may be used to detect a nucleotide, or a nucleotide sequence. In some cases the method may be used to identify a gene, a locus, a polymorphism, a translocation, an insertion, a deletion, a covalent or non-covalent modification, or a combination thereof. In some cases the method may be used to identify transcribed ribonucleic acids, for example, messenger RNA, transfer RNA, interfering RNA, regulatory RNA, nuclear RNA, mitochondrial RNA, etc.

The target polynucleotides may be of various lengths. For example, the target polynucleotides may be longer than about 10 nt and shorter than about 400 nt. In some cases, the target polynucleotides may be of one length. In other cases, various target polynucleotides may have different lengths. In various cases, the target polynucleotide may be longer than about 20 nt, 30 nt, 40 nt, 50 nt, 60 nt, 70 nt, 80 nt, 90 nt, 100 nt, 110 nt, 120 nt, 130 nt, 140 nt, 150 nt, 160 nt, 170 nt, 180 nt, 190 nt, 200 nt, 210 nt, 220 nt, 230 nt, 240 nt, 250 nt, 260 nt, 270 nt, 280 nt, 290 nt, 300 nt, 310 nt, 320 nt, 330 nt, 340 nt, 350 nt, 360 nt, 370 nt, 380 nt, 390 nt, and shorter than about 400 nt, 390 nt, 380 nt, 370 nt, 360 nt, 350 nt, 340 nt, 330 nt, 320 nt, 310 nt, 300 nt, 290 nt, 280 nt, 270 nt, 260 nt, 250 nt, 240 nt, 230 nt, 220 nt, 210 nt, 200 nt, 190 nt, 180 nt, 170 nt, 160 nt, 150 nt, 140 nt, 130 nt, 120 nt, 110 nt, 100 nt, 90 nt, 80 nt, 70 nt, 60 nt, 50 nt, 40 nt, 30 nt, 20 nt.

The target sequences may be of various lengths. In some cases the target sequence length may vary depending upon the complexity and/or size of a sample. For example where the sample is a genome. In other cases, the target sequence length may depend upon the sequence of the target and the type and number of nucleotides in the sequence. In other cases the target sequence length may be varied depending on the melting temperature, Tm, of the sequence, pH, salt concentration, or temperature of the incubating step. In some cases the target sequence length will be greater than about 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, 31 nt, 32 nt, 33 nt, or 34 nt and less than about 35 nt, 34 nt, 33 nt, 32 nt, 31 nt, 30 nt, 29 nt, 28 nt, 27 nt, 26 nt, 25 nt, 24 nt, 23 nt, 22 nt, 21 nt, 20 nt, 19 nt, 18 nt, 17 nt, 16 nt, 15 nt, 14 nt, 13 nt, 12 nt, 11 nt, 10 nt, 9 nt, 8 nt, 7 nt, 6 nt, or 5 nt. In many cases where a sample may or may not have multiple target sequences and/or polynucleotides, the Tm's of the various target sequences will be within about 1° C., about 2° C., about 3° C., about 4° C., about 5° C., about 6° C., about 7° C., about 8° C., about 9° C., and about 10° C. of each other.

Detection of Nucleotide Polymorphism

In some variations the target polynucleotides can be obtained from genomic DNA. Genomic DNA can be obtained from a variety of organisms, for example animals, plants, microbes, bacteria, viruses, etc. In some variations, genomic DNA is obtained from domesticated mammals, fowl, fish, and wild or cultured plants. In other variations, the target polynucleotides can be non-genomic DNA, for example synthetic DNA or DNA fragments. In variations wherein the target polynucleotides are obtained from an individual (ie genomic DNA), loci can be associated with specific genes, and polymorphisms can be associated with alleles of those genes. The target polynucleotide can be any target polynucleotide described herein.

Genes are sequences of DNA that code for proteins or for RNA chains, and include other DNA sequences that affect how, when, and how much of that protein and/or RNA sequence is made by the cell. Many plants and animals carry two copies of each gene (diploid), one copy inherited from each parent. These two copies can be identical, similar, or they can be different. In some variations, only no copies, one copy or more than two copies may be present. In some variations the organism may be haploid, triploid, tetraploid and higher. Within a large population of a species, many alleles of a gene can exist, but a single diploid organism, in most cases, will carry one or two alleles, or can include non-coding polynucleotides (e.g. DNA or RNA).

Different alleles can be associated with distinctive characteristics or traits that are passed-on from a parent to its offspring. In some cases, genes, and their alleles can be associated with dramatic and readily observable differences. Observable differences include, for example, eye-color, hair color, etc. Some genes, and alleles thereof can result in changes in metabolism, biochemical pathways, behavior, and other traits that are less readily observable. In some cases, a specific trait or characteristic can be the result of a combination of multiple genes and/or multiple alleles.

Alleles can be identified directly or indirectly. Direct identification involves identifying the nucleotide change or changes that give rise to the allelic difference, for example a mutation that deletes, truncates, or mutates a protein or RNA, makes a protein or RNA more or less active, or leads to over or under-expression of a protein or RNA. Indirect identification involves identifying changes in the DNA that are closely associated with inheritance of that allele. In some cases, the DNA changes can be within the gene itself, or in DNA sequences outside, or between the genes of interest.

In some variations of the present disclosure, alleles can be investigated through association with one or more nucleotide polymorphisms. In some variations, the polymorphism can occur at a single nucleotide position. In some variations one allele can be associated with a first nucleotide, for example thymine, at a given position and an alternative allele associated with a second nucleotide, for example cytosine, at that position. In other variations, the nucleotide polymorphism can include substitutions, deletions, insertions, copy number variation, translocations, nucleotide modification (such as methylation), and other changes in DNA sequence. In some variations the polymorphism can include two, three, four, or more contiguous nucleotides.

In some cases, many loci can be investigated in a single individual. In some variations, this can be used to genotype or DNA-fingerprint the individual. In some cases, by genotyping or DNA-fingerprinting an individual, it can be possible to determine the characteristics of that individual, for example specific traits or relatedness to specific groups of individuals. Finger printing can also be used to identify a specific individual from a pool of related individuals.

With reference to FIG. 1, the polymorphic nucleotide at Locus A can be either T or G. Thus individuals that are diploid for Locus A can be one of three genotypes: T/T, T/G, or G/G. In some instances, in a normally diploid species, an individual can have more than two copies of a gene and/or allele (as in trisomy), in other cases, an individual can have a single copy of a gene (as in monosomy).

Variations of the presently disclosed method may be used to analyze nucleotide polymorphisms, comprising a single nucleotide or multiple nucleotides. In some cases a single nucleotide position can be associated with two, three, or four different alleles. In some cases, one allele can be associated with multiple nucleotide polymorphisms.

FIG. 4 depicts one use of the present method to determine the genotype of a single target polynucleotide using complementary polynucleotides that further comprise a PCR tag sequence (diagonal lines). Here, two complementary polynucleotides are used. Each first complementary polynucleotide consists of a first complementary sequence, or hybridization sequence, and a PCR amplification sequence. The first complementary polynucleotide sequence further includes a 3' nucleotide(s) sequence that is complementary to the polymorphic nucleotide sequence on the target polynucleotide (in this figure "A"). The second complementary polynucleotide includes a second complementary sequence and a 5' phosphate group. If the first complementary polynucleotide sequence, including the 3' terminal nucleotide(s) base pairs with the target polynucleotide, a ligase enzyme will be able to ligate the first and second complementary polynucleotides to create a single ligated product polynucleotide If however, the first polynucleotide sequence 3' nucleotide(s) does not basepair with the target polynucleotide's polymorphic nucleotide sequences, the ligase may be unable to ligate the two polynucleotides. Thus, the ligase is used to discriminate a base pair mismatch at the first complementary polynucleotide sequence's 3' position.

As shown in steps (c) and (d) of FIG. 4, the next step in the presently disclosed method involves amplification of product polypeptides. For this step, the PCR amplification sequences on the first complementary polynucleotide and second complementary polynucleotide can be used to aid in creating highly multiplexed reaction. The enriched product polynucleotides can then be submitted for sequence data generation.

Step (a) of FIG. 4 shows the target polynucleotide with an adenine, "A," polymorphic nucleotide, two first complementary polynucleotides (LHS; one with a 3' G nucleotide [LHS-G] and its counterpart with a 3' T nucleotide [LHS-T]) and one second complementary polynucleotide (designated RHS) that is 5' phosphorylated (P) is added to target polynucleotide. Step (b) shows the period after hybridization, wherein a ligase is added and the successfully hybridized LHS-T is ligated to the adjacent RHS polynucleotide. Step (c) depicts the ligation polynucleotide serving as a template for PCR amplification. Step (d) shows a first PCR primer (diagonal arrow) directing amplification (second PCR primer not shown).

The locus shown in FIG. 4 can be A or C. Thus the LHS polynucleotides are either LHS-T or LHS-G, with T or G, at their 3' terminal nucleotides, respectively. In an genome that is homozygous for the A allele at this particular locus, (A/A), only a first complementary polynucleotide with a 3' T nucleotide, LHS-T, would basepair with the target polynucleotide, allow ligation between the first and second complementary polynucleotides, and form a subsequent product polynucleotide in the amplification step. The LHS-G polynucleotide, shown with a thick dark line in the middle, does not hybridize with an A/A homozygous sample having two target polynucleotides with A at the polymorphic nucleotide. An A/C heterozygous genome would produce two product polynucleotides: LHS-T joined to RHS and LHS-G joined to RHS. A C/C homozygous genome would produce the LHS-G joined to RHS product polynucleotide.

In some variations, during the PCR amplification step, a sample-specific tag sequence can be added to the first and/or second PCR primers and incorporated into the product polynucleotides. In some variations, two different sample-specific tags (one on each PCR primer) can aid in increasing the number of individuals that can be analyzed in a single genotyping experiment. In some variations, where fewer samples, or individuals are analyzed in a single experiment, only one PCR primer can include a sample-specific tag sequence. In some variations, the sample specific tag is on the LHS and/or the RHS and is not introduced in this PCR enrichment step.

In variations wherein the product polynucleotides are sequenced by next generation sequencing, the PCR primers can also contain sequences for use with a specific sequencing technique. For example, in some variations, Illumina sequencing can be used and the PCR primers can include sequences for permitting the product polynucleotides to anneal to the surface-bound DNA oligonucleotides within an Illumina NGS flow cell. In some variations, the sequences required for Illumina based sequence data generation are on the LHS and or the RHS and are not Introduced in this PCR enrichment step.

In some variations, two sequence data generation reads can be performed in order to identify the sample, locus, and allele identities of each product polynucleotide. In other variations, three sequence data generation reads can be used to determine the individual, locus, and allele identities of each product polynucleotide. In some variations, one sequence data generation read can be performed in order to identify the sample, locus, and allele identities of each product polynucleotide. In some variations, four sequence data generation reads can be performed in order to identify the sample, locus, and allele identities of each product polynucleotide.

Figure 5:
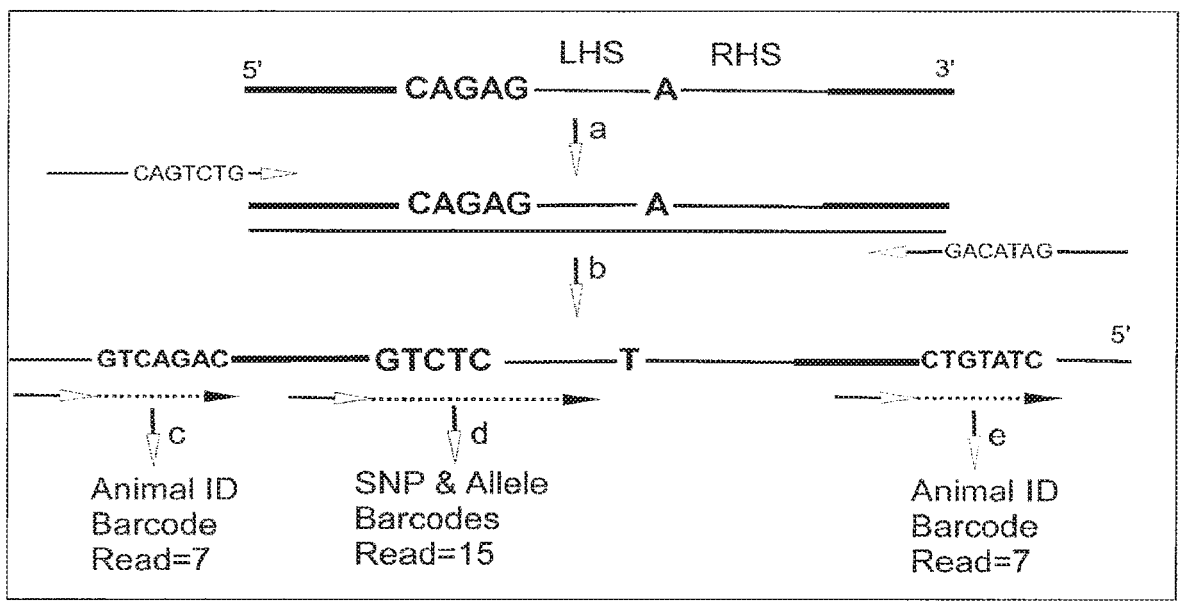
FIG. 5 depicts PCR steps used to add sample-specific sequence tags (GTCAGAC and CTGTATC) and the steps involved in reading said tags on a sequencing device.

In some variations the various first complementary polynucleotide, specific for a given locus, can include short polymorphism-specific or allele-specific tags (FIG. 5). The polymorphism-specific tag can allow identification of the specific polymorphic nucleotide (or allele) without having to sequence through the complementary/target sequences. Identification of the polymorphism in this way, can shorten read lengths and minimize sequencing reagent use and data acquisition time. Polymorphism-specific tags can be designed to allow up to 1, 2, 3, 4 or more sequencing errors while still allowing identification of the specific allele. In some variations, polymorphism-specific tags can be designed to allow up to 1, 2, 3, 4 or more sequencing errors while still allowing identification of the specific allele. In some variations, sample-specific tags can be designed to allow up to 1, 2, 3, 4 or more sequencing errors while still allowing identification of the specific sample. In some variations, locus-specific tags can be designed to allow up to 1, 2, 3, 4 or more sequencing errors while still allowing identification of the specific locus. Specific loci can also be identified by sequencing through the complementary/target sequences. In some variations, less than 15 nucleotides or more can be used to identify the individual polynucleotides and thus the specific locus.

FIG. 5 depicts the PCR steps used to add sample-specific sequence tags and the steps involved in reading said tags. In Step (a), after ligation of the first complementary polynucleotide (the 3' A nucleotide is shown) (LHS) and second complementary polynucleotide (RHS), a PCR primer containing a sample—specific sequence tag (GACATAG) directs PCR amplification of a first PCR product. In Step (b), a second PCR primer anneals to the first PCR product. The second PCR primer includes a second sample-specific sequence tag (CAGTCTG). In this figure, the reverse complement of the final product polynucleotide is shown and the 5' end that is bound to a sequencing flow cell is noted (5'). In Step (c), a first sequencing primer (sequencing primer 1; open arrow) is used to generate sequence data on the 7-base sample-specific sequence tag. In Step (d), a second sequencing primer (sequencing primer 2) is used to generate sequence data on the 5-base polymorphism-specific sequence tag and the first 10 bases of the first complementary polynucleotide (locus-specific sequence tag). In Step (e), a third sequencing primer (sequencing primer 3) is used to generate sequence data on a second sample-specific sequence tag. Sequencing reads from Steps (c) and (d) can be combined such that one long read starting with the outer Illumina primer (open arrow under GTCAGAC), generates the sequence data on the left sample-specific sequence tag, then a common PCR primer region (left thick bar), the polymorphism-specific sequence tag, and then the first complementary polynucleotide sequence containing the locus-specific sequence tag.

If the Illumina tags on either end of the LHS and RHS are exchanged, then the sequence read strategy can begin from the right side. In some embodiments, the read lengths would need to increase as the allele information exists in the LHS and not the RHS probe sequences. In other embodiments the allele tag may be placed on the RHS probe. Alternatively, the Illumina tags on either end of the LHS and RHS are swapped for one another and the allele (or other variation) information is on the RHS probe sequence. In other embodiments, sample and or locus tags may be placed in the RHS. In further embodiments the tags may be placed in either or both LHS and RHS probes. In further embodiments the tags may be in the LHS and or RHS probes or they may be added to the product polynucleotide after if is formed.

In many variations, the presently disclosed method can use low molecular weight target polynucleotides when only short regions of the polynucleotide are required for hybridization.

Figure 15:
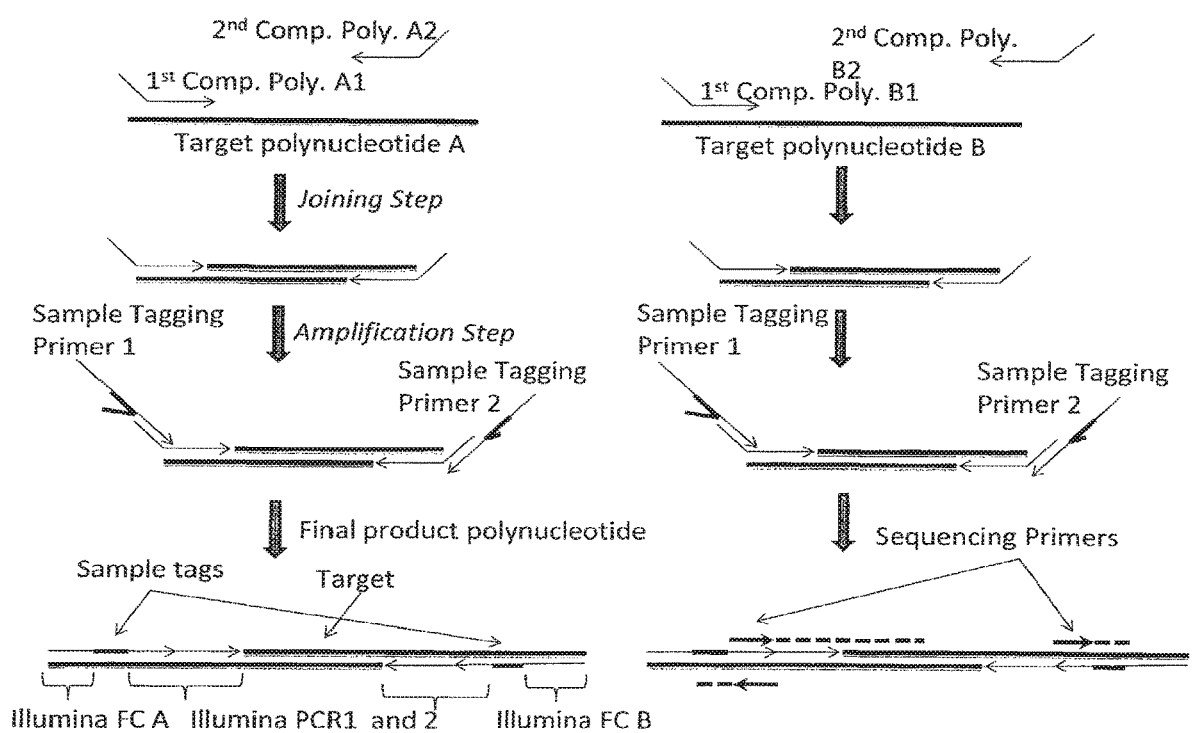
FIG. 15 depicts A PCR only based strategy for the detection of target polynucleotides and or their polymorphisms in a multiplex manner. Two different target polynucleotides (A and B) are shown in single stranded forms (bottom strand 3' to 5'). In the Joining Step, first complementary polynucleotide (A1) and second complementary polynucleotide (A2) primers amplify the A target polynucleotide while first complementary polynucleotide (B1) and second complementary polynucleotide (B2) amplify the B target polynucleotide. Each primer set is bounded by common sequences (diagonal lines). In the Amplification Step, these common sequences permit the Sample Tagging Primer 1 and Sample Tagging Primer 2 primers to amplify both product polynucleotides A and B concurrently. The diagonal red bars are sample-specific barcodes that tag the PCR products that comprise the product polynucleotide. The final product polynucleotides are arranged as shown with Illumina FC A and FC B on each end, these are the flow cell binding sequences. Next are the sample tags (gray bars), then the location for Illumina Sequencing Primer 1, the actual target polynucleotide sequence, the location for Illumina Sequencing Primer 2, the next sample tag (gray bars), and the final Illumina FC B flow cell binding sequence.

FIG. 15 depicts a non-ligation-based strategy comprising PCR in the joining step of the method.

With reference to FIG. 15, two different target polynucleotide (A and B) are shown in single stranded forms (bottom strand 3' to 5'). In the first amplification reaction, first complementary polynucleotide (A1) and second complementary polynucleotide (A2) amplify target polynucleotide A, while first complementary polynucleotide (B1) and second complementary polynucleotide (B2) amplify target polynucleotide B. In some variations, including this one, the second complementary sequence can be identical to the second target sequence, instead of complementary to it. In the amplification step, PCR tag sequences of first complementary polynucleotide (A1) and first complementary polynucleotide (B1), and second complementary polynucleotide (A2) and second complementary polynucleotide (B2), permit Sample Tagging Primer 1 and Sample Tagging Primer 2 to amplify both target polynucleotide A and target polynucleotide B concurrently. In various embodiments, it will be understood that any of, or any combination of, Primers A1, A2, B1, and B2 can include sample-specific tags, and further that the sample-specific tags can be included in either the joining or enrichment steps. The joining and enrichment steps can be performed in a single reaction or in multiple, discrete successive reactions.

Various tags can be included in any of the amplification steps. These tags can be specific for a sample, an allele or set of alleles, a target, and/or a locus or set of loci.

In one variation, the product polynucleotides can include one or more Illumina or other NGS-specific sequence. In this variation, the sequences in the product polynucleotide are arranged as shown with Illumina FC A and FC B on each end. These are the flow cell binding sequences. Next are the Sample Tagging Primer 1 tag sequence, then the first complementary polynucleotide (A1) or first complementary polynucleotide (B1) sequence, then polymorphism-containing target sequence, then the second complementary polynucleotide (A2) or second complementary polynucleotide (B2) sequence, the next Sample Tagging Primer 2 tag, and the final Illumina FC B flow cell binding sequence. It will be understood that the sequences can exist without NGS sequences (e.g. Illumina FC A and FC B).

This disclosure makes possible the high-throughput, lost cost genotyping of large numbers of samples for targeted polymorphism detection, including single-nucleotide polymorphism (SNP) detection, through next generation sequencing (NGS). By applying sample tags to the product polynucleotides, the sample from which each sequence read can be determined based on sample tag sequence in a specified location within the sequence of each read. Many samples can be pooled prior to obtaining a library for sequencing.

In various embodiments, any amplification reaction can be used. For example, the polymerase chain reaction (PCR) can be used to add tags to polynucleotides, making it feasible to pool thousands or tens of thousands of samples within one NGS lane. Two independent tags can be combined at different locations within the polynucleotide to allow labeling many samples using relatively few primers (e.g., 96×384=36,864 samples identified by 96+384=480 primers). In contrast with other applications of tagging samples for NGS, the method produces sequencing reads only of specifically tagged targets, such as SNPs. Therefore sequencing reads are not wasted on uninformative loci and the number of samples (individuals) that can be evaluated in one NGS lane is much greater (tens of thousands).

In various embodiments, the test can be used in agricultural industries. A large number of animals can be tested in a single run. The accuracy of testing could be improved greatly by genotyping several hundred of the most significant SNPs from research populations in 10-30,000 animals, including beef cattle, dairy cattle, swine and sheep. Outside agriculture, the method can be used to identify sequences in human genetics, food safety testing, environmental sampling, research animal genotyping, and human and livestock diagnostics.

The following example was performed: In the original proof-of-concept application (developed by ARS), the target SNP fragments were selected by highly multiplexed (96-fold) PCR. The method (and others described) uses the plateau effect of PCR to normalize the number of sequence reads with respect to both individuals and SNP loci.

In some variations, the joining step further comprises a PCR reaction in which the first and second complementary polynucleotides are PCR primers, the second complementary polynucleotide is identical to the second target sequence, and the second complementary polynucleotide is oriented 3' to 5' from left to right.

In some variations, the joining and enrichment steps are combined in one reaction step.

Genotyping

One variation of the presently described method combines identification of allele-associated nucleotide polymorphisms, and high throughput parallel sequencing technology, in order to simultaneously genotype or fingerprint very large numbers of individuals at a moderately large number of loci.

Sample

The sample can be anything that includes the target polynucleotide. For example, a sample can be obtained from a biological sample. Optionally, the sample can be modified by adding or removing non-nucleic acid components. The polynucleotide in the sample can be modified. Samples need not be homogenous. The sample may or may not contain a mixture of polynucleotides from many organisms. The sample may or may not contain a mixture of polynucleotides from individuals of the same species. The sample may or may not have been processed so that the analyte is a non-nucleic acid molecule. The sample can contain polynucleotides that have been processed, such as by amplification, purification, digestion, chemical modification, enrichment, selection, etc. The sample may or may not contain one or more non-target polynucleotides.

Sample DNA, target polynucleotides, can be obtained from a variety of sources. For example, the presently disclosed method can be used to genotype domesticated animals, non-domesticated animals, cultivated plants, non-cultivated plants, micro-organisms, viruses, and humans. In these variations, genomic DNA can be obtained. In some variations individuals can be mammals, for example, humans, cows, sheep, hogs, pigs. In other variations the individuals can be fish, for example, trout, salmon, or fowl, for example chicken, turkey, etc. In other variations, target polynucleotides other than genomic DNA can be used. For example, target polynucleotides can also be mitochondrial DNA, chloroplast DNA, extra-chromosomal DNA, plasmid DNA, artificial DNA, transposable elements, etc. Sources of target DNA can include air, water, soil, food, tissue, skin, hair follicles, feces, waste, semen, saliva, blood, and other bodily fluids. In some variations, samples can be obtained from a crime scene.

In many variations, the amount of DNA obtained can be less than about 100 μg, about 10 μg, about 1 μg, about 100 ng, about 10 ng, about 1 ng, about 100 μg, about 10 μg, about 1 μg, or about 100 fg. In some variations, the target polynucleotides can be isolated from samples using a variety of methods, for example mechanical isolation (such as glass-bead technology), chemical extraction methods, column based methods, or combinations thereof. DNA extraction methods are well-known to one of skill in the art, for example in Molecular Cloning: A Laboratory Manual, Third Edition, Joe Sambrook and David Russell, Jan. 15, 2001 (3rd edition), ISBN-10: 0879695773.

In some variations of the presently disclosed method, the target polynucleotides can have an average length of between 10 kbp and 100 kbp. In other variations, the target polynucleotides can have an average length of less than 10 kbp, or greater than 100 kbp. In other variations, the target polynucleotides can have an average length of less than 1 kb. In other variations, the target polynucleotides can have an average length of less than 750 bases. In other variations, the target polynucleotides can have an average length of less than 500 bases. In other variations, the target polynucleotides can have an average length of less than 250 bases. In other variations, the target polynucleotides can have an average length of less than 100 bases. In other variations, the target polynucleotides can have an average length of less than 50 bases. In many variations, the purified and isolated target polynucleotides can comprise little or no salt, for example the salt concentration can be less than 60 mM, 10 mM, 1 mM, 100 μM, 10 μM, 1 μM, 100 nM, 10 nM, or 1 nM.

First and Second Complementary Polynucleotides

In many variations, the length of the complementary sequence of the second and first complementary polynucleotide can be determined based upon the length, sequence, and Tm of a given complementary/target sequence, as well as the complexity of the sample DNA. For example, in some variations wherein the target polynucleotides are obtained from genomic DNA, the length of the complementary sequence can vary with the size of the organism's genome, for example a complementary sequence for a mammal can be required to be longer than the complementary sequence of a virus or a bacterium.

As described above, in some variations, the size of a given complementary sequence can correspond to the complexity of the target DNA. For example, a viral genome can comprise between 1 kb and 1 Mb. For a 1 kb viral genome, a specific 5 nt polynucleotide should occur only once ($4^5=1,024$), while 10+nt polynucleotide would theoretically be required to interrogate a 1 Mb genome ($4^{10}=1.049M$), and a 16+nt polynucleotide would theoretically be required to interrogate a 1 Bp genome ($4^{16}=4.3B$). Thus, in some variations, it can be possible to make a set of first and second complementary polynucleotides that are specific for pathogenic viruses.

For example, a polynucleotide sequence specific for the human pathogen *E. coli* 0157 can be detected from a 40 to 90 base region specific for this bacteria strain (or any pathogen DNA sequence or antibiotic resistance DNA sequence). In other variations, a 30 base region can be detected. In other variations, a 20 base region can be detected. In other variations, a 10 base region can be detected. Other polynucleotides would be made for other bacteria, or even viruses, or other organism or other sequences whose detection is desired. The polynucleotide panel would be run with a gDNA sample obtained from patient, saliva, gut lavage, stool sample, blood sample, food sample, animal sample, processing facility sample, air sample, plant sample, water sample, swab, swipe, etc. The sequencing library would be made, tagged for the number of samples in the library and sequence data generated. The results would show the relative intensity of the *E. coli* gDNA in the sample. Thus indicating the presence of that bacteria, or bacterial strain, or virus or organism, or presence of an antibiotic resistance DNA sequence, etc. As copy number variation can be detected, the test could also be made semi-quantitative.

Figure 14:
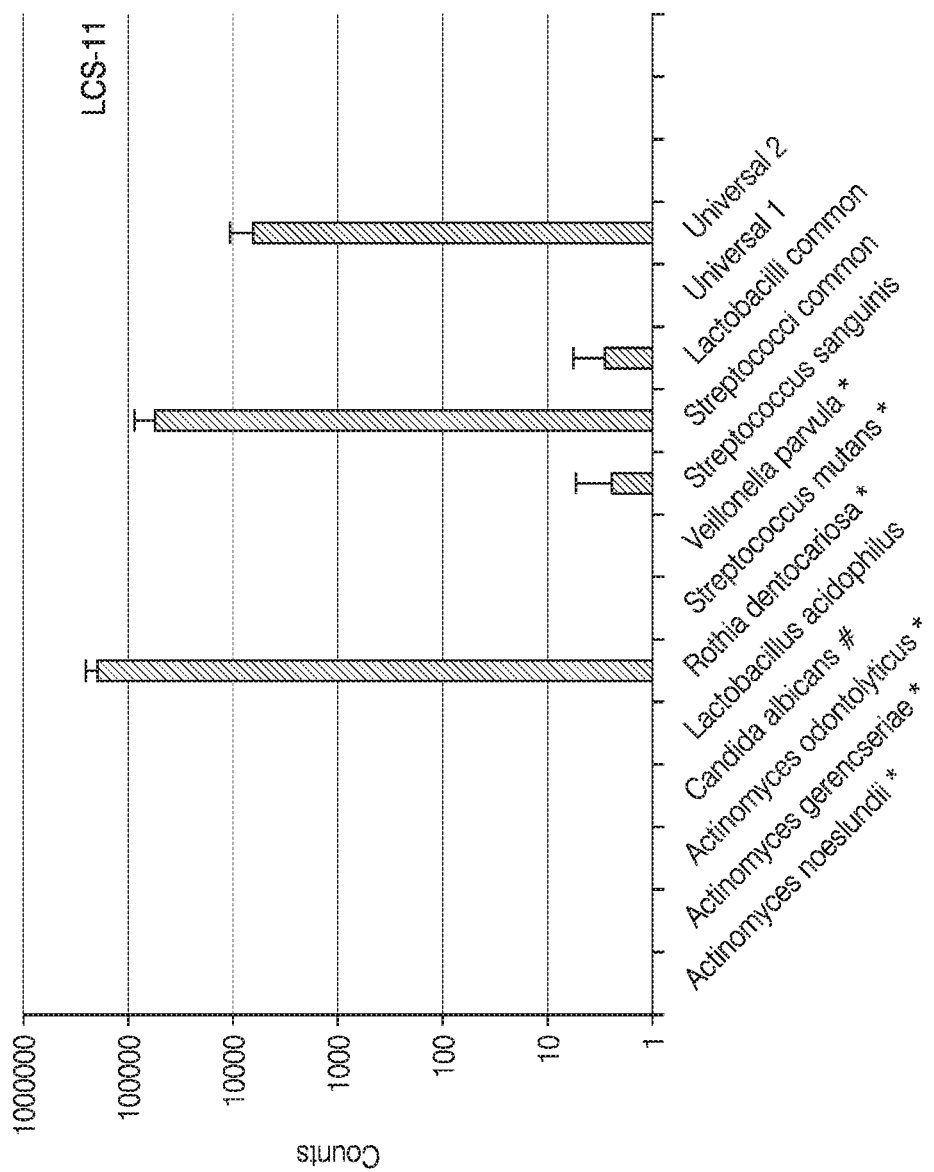
FIG. 14 depicts a spectrum of cariogenic oral bacteria (*), oral fungi (#), and other oral bacteria that may be present in the human oral cavity. The spectrum of the oral bacteria present in the saliva of two human subjects (LCS-11 and LCS-14) was determined by the oral bacteria specific MDST. In various embodiments, MDST is used to determining the presence or absence of a target polynucleotide in a sample as described herein, in a multiplex format. The mean counts are shown (bars) with standard deviations (whiskers).
Figure 14:
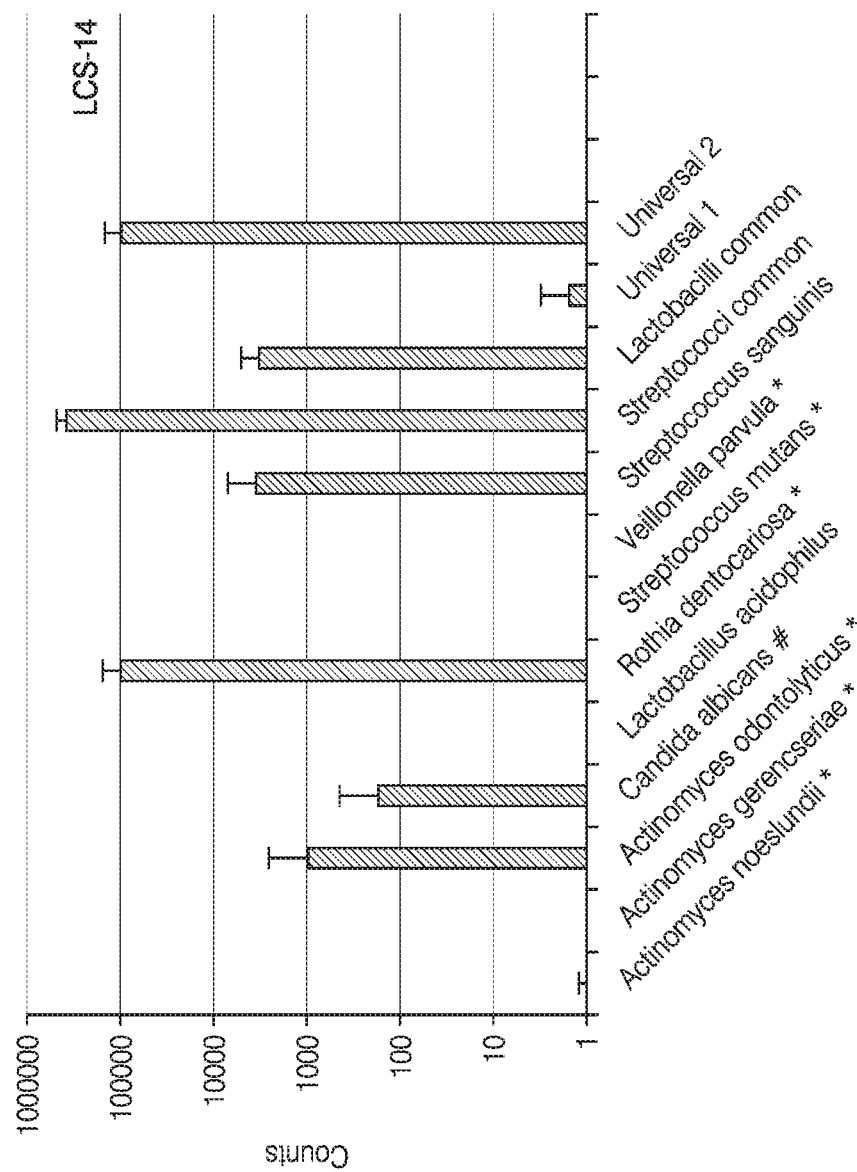

In another variation, the first and second complementary sequences are complementary to a target polynucleotide in the organism to be detected. In one variation, human saliva is processed into genomic DNA, which contains a mixture of human and bacterial genomic DNA. The DNA is mixed with a panel of first and second complementary polynucleotides that have sequences characteristic of cariogenic bacteria, a common fungal agent, and commensal bacteria, and target sequences that are common in most bacterial species. After hybridization of the panel of first and second complementary polynucleotides to the target polynucleotides, adjacent first and second complementary polynucleotide are joined, for example by the Taq DNA ligase enzyme to produce a panel of product polynucleotides. Optionally, sample specific tags, and/or sequences required for the Illumina sequencing reaction, are added by PCR. Sample tags are sequenced and compiled by sample and microbial target based on the microbial target locus tag. An example of the resulting data is depicted in FIG. 14. The sequence reads derived from the first complementary polynucleotide provide the tag for the locus information. Reading, or generating sequence data from, 6 to 15 bases of the first complementary polynucleotide can be sufficient to distinguish it from any of the first complementary polynucleotides in the panel.

A panel of probes (Terefework et al. 2008) with target polynucleotide sequences specific for cariogenic oral bacteria as well common oral bacterial and tagged with Illumina specific sequences were generated. Human saliva samples were processed to obtain purified genomic DNA. This genomic DNA was analyzed by the methods described herein. Samples were separately tagged. The first and second complementary polynucleotides were designed based on the target sequence described in Terefework, Z., C. L. Pham, et al. (2008). "MLPA diagnostics of complex microbial communities: relative quantification of bacterial species in oral biofilms." J Microbiol Methods 75(3): 558-565.

The first and second complementary polynucleotides may be of various lengths. For example, the first and second complementary polynucleotides may be longer than about 10 nt and/or shorter than about 400 nt. In some cases, the first and second complementary polynucleotides are of the same length. In other cases, the first and second complementary polynucleotides are of different lengths. In some cases one set of first and second complementary polynucleotides may have the same lengths as another set of first and second complementary polynucleotides. In various cases, the first and second complementary polynucleotides may be longer than about 20 nt, 30 nt, 40 nt, 50 nt, 60 nt, 70 nt, 80 nt, 90 nt, 100 nt, 110 nt, 120 nt, 130 nt, 140 nt, 150 nt, 160 nt, 170 nt, 180 nt, 190 nt, 200 nt, 210 nt, 220 nt, 230 nt, 240 nt, 250 nt, 260 nt, 270 nt, 280 nt, 290 nt, 300 nt, 310 nt, 320 nt, 330 nt, 340 nt, 350 nt, 360 nt, 370 nt, 380 nt, 390 nt, and shorter than about 400 nt, 390 nt, 380 nt, 370 nt, 360 nt, 350 nt, 340 nt, 330 nt, 320 nt, 310 nt, 300 nt, 290 nt, 280 nt, 270 nt, 260 nt, 250 nt, 240 nt, 230 nt, 220 nt, 210 nt, 200 nt, 190 nt, 180 nt, 170 nt, 160 nt, 150 nt, 140 nt, 130 nt, 120 nt, 110 nt, 100 nt, 90 nt, 80 nt, 70 nt. 60 nt, 50 nt, 40 nt, 30 nt, 20 nt.

In some cases, the first and second complementary polynucleotides may comprise complementary sequences and other nucleotides, nucleotide sequences, or tags. In some cases, the first and/or second complementary polynucleotide may comprise a polymorphism-, allele-, or nucleotide-specific tag, locus-specific tag, sample-specific tag, or combinations thereof. In some cases, the first and/or second complementary polynucleotides may comprise an amplification-specific tag, or a sequencing-specific tag. Amplification-specific tags may be used in cases wherein the method includes an amplification-based enriching step. Sequencing-specific tags may be specific for various types of sequencing protocols.

The complementary sequences may be of various lengths. In some cases the complementary sequence length may vary depending upon the complexity and/or size of a sample, for example where the sample is a small genome of a sample from a complex environment. In other cases, the complementary sequence length may depend upon the target sequence and the type and number of nucleotides in that sequence. In other cases the complementary sequence length may be varied depending on the melting temperature, Tm, of the sequence, pH, salt concentration, or temperature of the incubating step. In some cases the complementary sequence length will be greater than about 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, 31 nt, 32 nt, 33 nt, or 34 nt and less than about 35 nt, 34 nt, 33 nt, 32 nt, 31 nt, 30 nt, 29 nt, 28 nt, 27 nt, 26 nt, 25 nt, 24 nt, 23 nt, 22 nt, 21 nt, 20 nt, 19 nt, 18 nt, 17 nt, 16 nt, 15 nt, 14 nt, 13 nt, 12 nt, 11 nt, 10 nt, 9 nt, 8 nt, 7 nt, 6 nt, or 5 nt. In many cases where a sample may or may not have multiple complementary sequences and/or polynucleotides, the Tm's of the various complementary sequences will be within about 1° C., about 2° C., about 3° C., about 4° C., about 5° C., about 6° C., about 7° C., about 8° C., about 9° C., and about 10° C. of each other.

In some variations the thermodynamic equation for Tm is based on nearest-neighbor interactions;
$Tm=((\Delta H°-1000)/(A+\Delta S°+R \ln(C_t/4)))-273.15+16.6 \log[Na^+]$. Where $\Delta H$ (Kcal/mol) is the sum of the nearest neighbor enthalpy changes for hybrids, A is a small, but important constant containing corrections for helix initiation, $\Delta S$ (eu) is the sum of the nearest neighbor entropy changes, R is the Gas Constant (1.987 cal deg$^{-1}$ mol$^{-1}$) and $C_t$ is the total molar concentration of strands. If the strand is self complementary, $C_t/4$ is replaced by $C_t$. $\Delta H$, $\Delta S$, $\Delta G$ values for nearest neighbor interactions of DNA 1M NaCl are:

| Nearest-neighbor sequence (5'-3'/3'-5') | $\Delta H°$ kJ/mol | $\Delta S°$ J/(mol · K) | $\Delta G°_{37}$ kJ/mol |
| --- | --- | --- | --- |
| AA/TT | −33.1 | −92.9 | −4.26 |
| AT/TA | −30.1 | −85.4 | −3.67 |
| TA/AT | −30.1 | −89.1 | −2.50 |
| CA/GT | −35.6 | −95.0 | −6.12 |
| GT/CA | −35.1 | −93.7 | −6.09 |
| CT/GA | −32.6 | −87.9 | −5.40 |
| GA/CT | −34.3 | −92.9 | −5.51 |
| CG/GC | −44.4 | −113.8 | −9.07 |
| GC/CG | −41.0 | −102.1 | −9.36 |
| GG/CC | −33.5 | −83.3 | −7.66 |
| Terminal A-T base pair | 9.6 | 17.2 | 4.31 |
| Terminal G-C base pair | 0.4 | −11.7 | 4.05 |

In some cases, Tm can be determined by methods well known to one of skill in the art, for example by using an algorithm such as that found in the oligo designing program Go-Oli-Go. For example, Tm is determined by standard/common algorithms such as the nearest neighbor as taught, for example, in Breslauer et al., (1986) Proc. Nat. Acad. Sci. 83:3746-50. A first complementary polynucleotide and second complementary polynucleotide can be greater than 17 nt, 18 nt, 19 nt, 20 nt, 21 nt, 22 nt, 23 nt, 24 nt, 25 nt, 26 nt, 27 nt, 28 nt, 29 nt, 30 nt, 31 nt, 32 nt, 33 nt, 34 nt, and less than 35 nt, 34 nt, 33 nt, 32 nt, 31 nt, 30 nt, 29 nt, 28 nt, 27 nt, 26 nt, 25 nt, 24 nt, 23 nt, 22 nt, 21 nt, 20 nt, 19 nt. In many variations the length of a complementary sequence of a specific first complementary polynucleotide or second complementary polynucleotide, can depend on the specific sequence of nucleotides. In most variations the annealing temperature, or melting temperature, Tm, of a specific sequence will be great than about 69° C., about 74° C., about 79° C., about 84° C., about 89° C., or about 94° C. and less than about 95° C., about 90° C., about 85° C., about 80° C., about 75° C., or about 70° C. In some variations the hybridization sequences can have Tm within about 1° C., about 2° C., about 3° C., about 4° C., about 5° C., about 6° C., about 7° C., about 8° C., about 9° C., and about 10° C. of each other.

In some variations, a first complementary polynucleotide sequence, in addition to the 3' polymorphic nucleotide and the complementary sequence, can further comprise a polymorphism-tag sequence. In some variations, the polymorphism-tag sequence is not complementary to target sequence at the given locus. In some variations the polymorphism-tag sequence can code for the identity of the 3' polymorphic nucleotide on a specific first complementary polynucleotide, and thus the specific polymorphic nucleotide in the target polynucleotide. In some variations, the polymorphism-tag sequences of the various first complementary polynucleotide, specific for a given locus, will not be the same. In some variations the polymorphism-tag sequence can be more that about 1 nt, 2 nt, 3 nt, 4 nt, 5 nt, 6 nt, 7 nt, 8 nt, 9 nt, or 10 nt, or less than about 15 nt, 14 nt, 13 nt, 12 nt, 11 nt, 10 nt, 9 nt, 8 nt, 7 nt, 6 nt, 5 nt, 4 nt, 3 nt, or 2 nt.

In some variations, the polymorphism-tag sequence can code for a specific nucleotide: adenine, thymine, cytosine, or guanine. In variations wherein the polymorphism-tag sequence codes for a specific nucleotide identity, first complementary polynucleotide from different loci can have similar or the same polymorphism-tag sequences. For example, in one variation of the polymorphism-tag sequence GTCTC can code for a thymine, T, nucleotide; GCACT for C; GGAGT for G; and GACAC for A. In other variations, T, C, G, and A can be coded for by different sequences.

In some variations the first complementary polynucleotide can further comprise a locus-specific tag sequence. In some variations the locus-specific tag sequence cannot be complementary to target sequence at a given locus. In some variations the locus-specific tag sequence can code for the identity of a given locus. In some variations, the locus specific tag sequence can be greater than 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, or 20 nt, and less than about 29 nt, 28 nt, 27 nt, 26 nt, 25 nt, 24 nt, 23 nt, 22 nt, 21 nt, 20 nt, 19 nt, 18 nt, 17 nt, 16 nt, 15 nt, 14 nt, 13 nt, 12 nt, 11 nt, 10 nt, 9 nt, 8 nt, 7 nt, 6 nt, or 5 nt.

In some variations, the first complementary polynucleotide and second complementary polynucleotide can Include sequences used in amplification (e.g. PCR). In some variations, the amplification sequences can be complementary to, or completely complementary to, sequences of polymerase chain reaction (PCR) amplification primers. In some variations, the amplification sequences can have lengths greater than 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, or 20 nt, and less than about 29 nt, 28 nt, 27 nt, 26 nt, 25 nt, 24 nt, 23 nt, 22 nt, 21 nt, 20 nt, 19 nt, 18 nt, 17 nt, 16 nt, 15 nt, 14 nt, 13 nt, 12 nt, 11 nt, 10 nt, 9 nt, 8 nt, 7 nt, 6 nt, or 5 nt.

In some variations the first complementary polynucleotide and second complementary polynucleotide of a given locus can further comprise sequencing tags. In some variations, the sequencing tag sequence can be greater than 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, or 20 nt, and less than about 29 nt, 28 nt, 27 nt, 26 nt. 25 nt, 24 nt, 23 nt, 22 nt, 21 nt, 20 nt, 19 nt, 18 nt, 17 nt, 16 nt, 15 nt, 14 nt, 13 nt, 12 nt, 11 nt, 10 nt, 9 nt, 8 nt, 7 nt, 6 nt, or 5 nt. In some variations the sequencing tags and/or PCR tags can comprise sequences that correspond to part or all of an Illumina sequencing adapter. In one variation, the two Illumina tags can be (A)=5'-AG-ACGTGTGCTCTTCCGATCT on the second complementary polynucleotide, and (B)=5' A-CACTCTTTCCCTACACGACGCTCTTCCGATCT on the first complementary polynucleotide. These sequences can be reversed as required. For example the Illumina A tag can replace the Illumina B tag so long as the Illumina B tag is replaced with the Illumina A tag.

In some variations, the second complementary polynucleotide can further comprise a 5' terminal phosphate group.

Incubating

The target polynucleotides can be made single stranded by denaturation. The samples may be denatured before or after combining with the first and second complementary polynucleotides. In some cases, samples comprising target polynucleotides can be denatured in a solution. The solution can be any solution known in the art. For example, a water solution without buffer can be used. Alternatively, a solution of Tris-HCl and EDTA can be used. After raising the temperature of the solution to about 98° C. for about five minutes, double stranded polynucleotides are denatured. In these cases, after denaturation of the target polynucleotides, first complementary polynucleotides, second complementary polynucleotides, and a hybridization solution can be added to create an incubation mix, to aid in creating duplex DNA. In other cases, the sample, and first and second complementary polynucleotides may be combined and then the sample may be denatured. In some cases, the sample may be single stranded and may not need to be denatured.

The temperature of the hybridization solution can then be raised to about 98° C. for about 1 min to about 10 min. In other variations, the incubation mix can be raised to greater than about 95° C., about 96° C., about 97° C., about 98° C., about 99° C., or about 100° C., and the temperature held constant for about 1 min, about 2 min, about 3 min, about 4 min, about 5 min, about 6 min, about 7 min, about 8 min, about 9 min, about 10 min, about 11 min, about 12 min, about 13 min, about 14 min, about 15 min, about 16 min, about 17 min, about 18 min, about 19 min, about 20 min, or greater than 20 min.

The incubation mix can then be allowed to cool to 60° C., room temperature, or other temperature and held at this temperature for a period of time. In other variations, the incubation mix can be allowed to cool to about below 25° C., about 30° C., about 35° C., about 40° C., about 45° C., about 50° C., 55° C., about 56° C., about 57° C., about 58° C., about 59° C., about 60° C., about 61° C., about 62° C., about 63° C., about 64° C., about 65° C. about 70° C., about 75° C., or about 80°. The temperature held constant for a period of time, such as greater than about 1 minute, greater than about 3 minutes, greater than about 5 minutes, greater than about 15 minutes, greater than about 30 minutes, greater than about 45 minutes, greater than about 1 hr, greater than about 1.5 hrs, greater than about 2 hrs, greater than 2 about 0.5 hrs, greater than about 3 hr, greater than about 3.5 hr, greater than about 4 hr, greater than about 4.5 hr, greater than about 5 hr, greater than about 5.5 hr, greater than about 6 hr, greater than about 6.5 hr, or greater than about 7 hr.

Joining

In some cases, after the target polynucleotide, and the first and second complementary polynucleotides have been Incubated under conditions that allow hybridization of complementary polynucleotides, the first and second complementary polynucleotides may be joined. Joining can be accomplished in a variety of ways. In some cases the first and second complementary polynucleotides may be joined non-covalently as described herein. In other cases, the first and second complementary polynucleotides may be joined covalently. In some cases, the covalent joining may be accomplished by use of a ligase, for example ligase from *T. aquaticus*.

A DNA ligase and ligation buffer solution can be added to create a ligation mix for aiding in ligating adjacent first complementary polynucleotide and second complementary polynucleotide molecules. In some variations, the ligation solution can contain DNA Ligase from *T. aquaticus* or Ligase-65. The temperature of the ligation mix then can be held constant for about 1 min, about 2 min, about 5 min, about 10 min, about 11 min, about 12 min, about 13 min, about 14 min, about 15 min, about 16 min, about 17 min, about 18 min, about 19 min, about 20 min, or greater than 20 min. This can aid in completing the ligation of the first complementary polynucleotide and second complementary polynucleotide molecules.

The temperature of the ligation mix can then be increased to about 94° C. for about 1 min to aid in inactivating the DNA ligase and denaturing the product polynucleotides. In other variations the temperature can be increased to about 90° C., about 91° C., about 92° C., about 93° C., about 94° C., about 95° C., about 96° C., about 97° C., about 98° C., or about 99° C. for about 1 min, about 1 min, about 2 min, about 3 min, about 4 min, or about 5 min. The ligation mix can then be rapidly cooled to room temperature, about 4° C., or about 0° C.

In some variations involving ligase mediated joining, the first complementary polynucleotide and second complementary polynucleotide can join if the 3' nucleotide(s) of the first complementary polynucleotide is complementary to the target polymorphic nucleotide or nucleotides. In other variations the first complementary polynucleotide and second complementary polynucleotide can join if the 3' nucleotide(s) of the first complementary polynucleotide is not completely complementary to the target polymorphic nucleotide or nucleotides, provided that the terminal ends of the first and second complementary polynucleotides are hybridized to the target polynucleotide.

Universal Base

In some variations the use of a "universal base," for example, inosine or 5-Nitroindole, can aid in preventing joining of molecules wherein the first complementary polynucleotide is not complementary to the target polymorphic nucleotide or nucleotides. In these variations, a universal base can be substituted at the $2^{nd}$, $3^{rd}$, $4^{th}$, $5^{th}$, $6^{th}$, $7^{th}$, $8^{th}$, $9^{th}$, or $10^{th}$ 3' nucleotide to aid in preventing or reducing joining of first complementary polynucleotide molecules that do not have a 3' nucleotide or nucleotides complementary to the target polymorphic nucleotide. Alternatively, or in addition to the above, a universal base can be substituted at the $2^{nd}$, $3^{rd}$, $4^{th}$, $5^{th}$, $6^{th}$, $7^{th}$, $8^{th}$, $9^{th}$, or $10^{th}$ 5'-nucleotide if the second complementary polynucleotide to aid in preventing or reducing joining of the second complementary polynucleotide molecules that do not have a 5'-nucleotide or nucleotides complementary to the target polymorphic nucleotide.

Enriching

In some variations of the present method, there can be an enriching step. The enriching step may increase the ratio of product polynucleotide to non-product polynucleotide. In some variations that include an enriching step, the product polynucleotide may be selected by size, affinity, charge, or sequence. In other cases the enriching step may comprise removal of some or all of the non-product polynucleotides, for example by selection, segregation, or digestion.

In some variations the enriching step may include size selection of the product polynucleotide, wherein the results of the joining step are separated on a gel or sizing column. In some embodiments, the product polypeptide may be selected based on the presence of a specific sequence, a tag, or the complementary sequence. In some cases, the product polynucleotide may be enriched by selecting for a sequence at one end of the product polynucleotide, and then selected again for a sequence at the other end of the product polynucleotide. This double selection may aid in removing sample sequence, target sequence, and the first and second complementary polynucleotides that have not been joined. In some cases, the product polynucleotide may comprise a sequence tag that is designed to be selected during an enrichment step.

In some cases the enriching step may comprise amplification of the product polynucleotide. In some of these cases, the enriching step can comprise amplification of the product polypeptides to create an amplified product. In these cases, the product polypeptides can be used as templates for DNA amplification, for example by PCR. In these variations, PCR primers can be combined with the product polynucleotide.

In some variations the PCR primers can comprise an annealing sequence that is complementary to a portion of the product polynucleotide or the target polynucleotide. For example, where a first and a second PCR primer are used to direct PCR amplification of a product polynucleotide, the first PCR primer may comprise an annealing sequence that is complementary to a sequence on the product polynucleotide, and the second PCR primer may have an annealing sequence that is homologous to a sequence on the product polypeptide. This can allow the second PCR primer to anneal to the polynucleotide created by polymerizing from the first PCR primer.

In some cases, the PCR primers may further comprise other sequences, for example, sample-specific tags and/or sequencing tags.

Sample Specific Sequence/Tag

As described above, in some variations of the present method, an enrichment step is added. In these variations, such as wherein the enrichment step comprises an amplification step and amplification primers, the amplification primers can further include sequences that can be used to identify the sample being amplified (sample tags). In some of these variations, the amplification primers can further include sequences that can aid in the sequencing of amplified products with a variety of sequencing methods. In some variations the sequencing method can be Illumina-based, and the amplification primers can include Illumina sequencing sequences. In some variations a portion of the sample tag may be added to one end of the product polynucleotide and a portion of the sample tag may be added to the other end of the product polynucleotide. In other variations the entire sample tag may be added to one or the other end of the product polynucleotide or to both ends of the product polynucleotide.

In some variations of the presently disclosed method, first and or second complementary polynucleotide design can obviate the need for sequencing the complementary or target sequences. In these variations, sample, locus, and allele (or other variation) identity are all encoded by sequence tags on the various polynucleotides and primers.

Determining the Presence or Absence of a Nucleotide or Nucleotide Sequence

In some variations of the method, the presence or absence of a nucleotide or nucleotide sequence may be determined by determining the product polynucleotide's sequence. Sequencing of the product polynucleotide may be accomplished by a variety of methods including chain termination, sequencing by synthesis, next generation sequencing, and other sequencing methods disclosed herein.

In some cases, such as wherein Illumina sequencing is used to determine the sequence of the product polynucleotide, the product polynucleotide can comprise sequences that allow the product polynucleotide to be captured by a flow cell and/or amplified on the flow cell.

The presence or absence of the target polynucleotide can be determined indirectly by detecting the sequence of at least a part of a tag sequence. In various embodiments, the tag sequence is a polymorphism-specific tag that corresponds to the sequence of a complementary polynucleotide. By way of illustration as described in FIG. 2E, the first complementary polynucleotide can comprise a polymorphism-specific tag sequence 5' of the complementary sequence. The polymorphism is detected by detecting at least part of the tag sequence. The present of the target polynucleotide is then detected.

It will be appreciated that a polymorphism-specific tag can be attached to a first or second complementary sequence.

Quantitation.

In some variations of the method, target polynucleotide copy number may be determined. For example, sequences can vary by number, from one to 1000s of copies. CNV (copy number variation) is implicated in gene control and human disease. To analyze CNV by the presently disclosed method, it can be possible to design first and second complementary polynucleotides for each potential CNV gene and one or more single gene copies. These polynucleotides can be tagged as described above. The relative read counts of the CNV gene (target polynucleotide) and single copy target polynucleotide(s) can be used to estimate copy number of the CNV gene (target polynucleotide). Alternatively, differential expression of RNA can be detected by measuring the relative change in quantity of tagged RNA. Alternatively, quantitation of the amount of a target polynucleotide in a sample containing nucleic acids from more than one individual of the same species can be determined. An example is the detection of the presence of genetically modified (GMO) soybean seeds in a mixture of GMO and non-GMO seeds. Alternatively, quantitation of the amount of target polynucleotide in a sample of nucleic acids obtained from more than one individual of different species can be determined. An example is the detection of a pathogen in a clinical sample or in a food sample.

CNV is determined solely by comparing samples with differing or known CNV to the unknown samples. For example a sample may have one copy of a locus, while another sample may have two or more copies; the first sample will yield a signal of X, while the second sample would have a greater signal of 2× or more. If required samples with constructed CNV can be used for the generation of standard curves. These would be synthetic DNA sequences doped into similar DNA samples. The doping would be in genome equivalents and greater, and the doped samples would output differing signals, forming a standard curve by which the unknown samples could be compared and the copy number (and its variation) determined.

Data analysis can reveal the sequence copy number and distinguish the fold differences from a normalized sample or gene (target polynucleotide). In some variations this is applied to the determination of copy number variation. For a sample with two copies of the target polynucleotide, the total number of sequence reads would, relative to the normalized sample, show that there are two copies of the target polynucleotide. But a sample with a 4-fold gene variation would yield 4 times the number of sequence reads. A sample with a deletion, would yield no sequence reads at all. Thus the assay reads CNV and even gene deletion.

Restriction Endonuclease/Methylation-Based Identification

Restriction endonucleases target specific DNA sequences for cutting. Again for Illustration, if a restriction endonuclease with a target recognition sequence GTACGC Is used on the DNA sequences depicted in FIG. 2A, only one target polynucleotide will be cut—the sequence depicted in FIGS. 2A, and 2B (i).

A sample that may or may not contain a target polynucleotide is combined with the first and second complementary polynucleotides and set to hybridize, then joined to produce product polynucleotides. The product polynucleotides are split into two different reactions. One reaction is seeded with a methylation sensitive restriction enzyme that has a recognition sequence within the probe binding area. The other reaction does not have an added restriction enzyme. The two reaction products can then be amplified. Sites that are methylated will not be digested and will present signal. This is compared to the non-digested sample. Sites that are non-methylated will be digested and will not amplify and will not present signal, and again these are compared to the non-digested sample signal. In another variation, the second non-digested sample is not required. In another variation the enzyme is not methylation dependent. In yet another variation the sample is treated with a restriction enzyme (methylation dependent or not) and then treated so that the cut ends cannot join. The first and second complementary polynucleotides are added to the treated sample and set to hybridize and then joined and sequence data is generated. The presence of the restriction site in or near the target sequence in the sample, allows the restriction enzyme to destroy the ability of the first and second complementary polynucleotides to be positioned in a manner that allows the joining. When joining is prevented, the product polynucleotide is not generated and direct or indirect sequencing of the product polynucleotide does not occur, or alternatively rarely occurs. In contrast, samples in which the restriction site is modified or missing between the first and second complementary polynucleotides will generate sequence reads. In an alternative approach the two reactions are seeded with a methylations sensitive and a methylation insensitive restriction endonuclease that recognize the same polynucleotide sequence. An example of this type of endonuclease pair is AscI (GG/CGCGCC).

In some variations, restriction endonucleases that are methylation-dependent can be used to digest sample DNA and thus target polynucleotides prior to hybridization, joining and sequencing. Digested target DNA will not allow joining of the first and second complementary polynucleotides. It will be appreciated that the presence or absence of other methylation sensitive restriction sites can be similarly interrogated. It will be appreciated that the presence or absence of other non-methylation sensitive restriction sites can be similarly interrogated.

In this variation of the presently disclosed method, first and second complementary polynucleotides can be made for a gene regulated by DNA methylation and present at a site/loci that contains a methylated restriction site (example HhaI). Sample DNA is then digested with the HhaI restriction enzyme [restriction site is GCGC] which does not cut at the methylated site. Alternatively, other methylation-sensitive restriction enzymes may be used that recognize sequences within the target polynucleotide. An uncut target DNA sample is also analyzed. Multiple polynucleotides for different potentially methylated sites can be made up with locus-specific tags. Multiple samples can be differentiated by using sample-specific tags. The joining and enrichment is performed and the library then sequenced. Analysis of the sequence data can then be used to determine either (A) or (B). In (A) for site1 cut sample—no signal AND for site1 uncut sample—a full signal. This indicates that site 1 is methylated. Alternatively, the data analysis can show (B) for site 1 cut sample—a full signal, AND for site 1 uncut sample—an equal signal. This indicates that site 1 is non-methylated. Hundreds of sites for hundreds of samples can be analyzed.

Scoring

The sequences of the product polynucleotides are determined either by direct sequencing of the complementary sequences or by sequencing of the tag sequences. In variations of the method for determining genotype of various samples, the sequencing data can be analyzed to determine whether specific loci are heterogeneous or homogeneous. In some variations, as described above, the copy number of specific target sequences may be determined. For example, specific loci can have only one copy (ie be monozygous), or have more than two copies (eg where the individual is trisomic at that locus). In many variations, number of loci as well as polymorphisms within those loci can be determined by a mathematical algorithm.

Wherein the method of genotyping combines ligation-dependent analysis and multiplexed sequencing, genotypes can be determined by examining allele frequencies. Allele frequency can be determined for a given two-allele locus by dividing the number of reads for a given allele by the total number of reads at that locus. For example, where a locus has two alleles, Allele A and Allele B, the frequency of Allele A can be determined by dividing the number of Allele A reads by the sum of Allele A and Allele B reads.

Wherein the method of genotyping combines ligation-dependent analysis and multiplexed sequencing, genotypes can be determined by examining allele read counts. For a two allele locus, the genotype can be determined by computing the ratio $R_A/(R_A+R_B)$, where RA is the number of reads confirming allele A and the RB is the number of reads confirming allele B at this locus. In this manner, when the ratio is near zero, the homozygote BB genotype can be inferred. Likewise, when the ratio is near one, the homozygote AA genotype can be inferred. Finally, ratio values around 0.5, correspond to the heterozygote AB genotype.

The processes by which reads confirming allele A and B are obtained are not always equally efficient. This means that for some loci and probe combinations a typical ratio of 0 for BB, 0.5 for AB and 1 for AA will not be appropriate. For example, a particular locus or probe may exhibit a ratio of 0.2 for BB, 0.7 for AB, and 0.9 for AA genotypes. To account for this, behavior of probes for a given locus (expected ratio values for genotypes) can be determined by running training experiments to establish mean ratio (using samples with known genotypes) and variance estimates. Alternatively, clustering techniques can be used to identify expected mean ratios, provided the number of distinct genotypes for a given locus is known (1, 2, or 3).

One such clustering technique is k-means clustering (though other clustering approaches may be used). Under this approach, ratios $R_A/(R_A+R_B)$ from multiple, different samples (animals) at a particular locus can be partitioned into k clusters, such that each observation assigned to a cluster is closer to this cluster's mean than to the mean of any other cluster. The number of clusters must be specified prior to start of clustering to avoid significant misclassification issues. This can be achieved by manually specifying the number of clusters (expert opinion); quality-of-fit selections strategies whereby partitioning with varying number of clusters is attempted for the data (in this case the choices are 1, 2, or 3) and the best fit (whether by minimizing cluster variance, cluster separation, or by other means) is chosen; or by other established k-means clustering techniques. Other clustering approaches include, but are not limited to (i) machine learning approaches, such as neural networks or Support vector machines, (ii) statistical approaches, such as non-parametric density clustering and k-means clustering with expectation maximization, and (iii) parametric modeling based on counts of reads for allele A and B. If there are more than two alleles the clustering approach may include the above (and other frequency space methods) and may be expanded to include three dimensional count space.

Once the observations for a given locus have been partitioned into one, two, or three clusters (depending on the observed ratios), the genotype call—AA, AB, or BB can be assigned to each cluster. One approach that can be used for this genotype assignment involves computing the distance between the cluster center points and expected frequencies for each genotype at a given locus and selecting the genotype call with the minimum distance to the cluster center. Expected frequencies can be the default ratios of 0 for BB, 0.5 for AB and 1 for AA, expert specified ratios, or mean ratio from previous training set experiments.

Alternatively, clustering can be performed on the counts of reads for allele A and Allele B, rather than in the frequency space. To do this, rather than projecting the counts onto the frequency line by computing the ratio of $R_A/(R_A+R_B)$, the read counts $R_A$ and $R_B$ are used directly. For example, $R_A$ can be displayed on the x-axis, while $R_B$ can be displayed on the y-axis. The k-means clustering approach outlined above can still be applied in two-dimensional space without any significant modifications. Similarly, for loci with 3 possible alleles (A, B, or C), a three dimensional approach can be used, where x axis is number reads for allele A, y-axis is the number of reads for allele B, and z axis is the number of read for allele C. The same clustering approaches (for example k-means), will also work here.

The sample tag sequence can be used to identify the sample a given read on the lane of the flowcell belongs to. Currently, this tag is placed in the index portion of the Illumina GAIIx read. In this fashion the sample assignment can be handled by simple de-multiplexing of a lane. The location of the tag is not exclusive to the index portion the read however—the sample tag can be incorporated into the read itself (added to the beginning of each sequenced read, in the middle, or in the end), without affecting the rest of the genotyping effort.

There are currently two different variants for the placement of the allele tag (to call A or B allele), with locus tag placement being common across both variants. Under the first variant, the allele tag is 5 bases (the first 5 bases of the read), while the locus is the next 15 bases of the read. The allele tag used for this variant are: "GTCTC", "GCACT", "GGAGT", and "GACAC" (although other allele tag may be designed in the future, if warranted), with the fourth base of the tag specifying the allele nucleotide A, C, T, or G. Multiple mismatches are allowed when identifying the allele tag (by default at most 2). Under the second variant, the allele tag is 3 bases (the first three bases of the read), while the locus is the next 15 bases. The third base of the allele tag specifies the allele nucleotide (A, C, T, or G), with no mismatched tolerated during its identification. Immediate following the allele tag in both variants is the locus tag of 15 bases. The 15 bases of the locus tag are specific to each of the locus being examined and are known a priori. Multiple mismatches are tolerated when identifying the locus tag (up to 3 by default).

Each lane undergoes a binning process, whereby each read on a lane is assigned appropriate sample (based on sample tag), locus (based on locus tag), and allele (based on allele tag and variant type). For each locus, only the reads corresponding to the two expected nucleotides (for allele A and B) are kept. Reads that cannot be binned to the proper sample-locus-allele are discarded from further analysis.

In some cases, a heterozygous, diploid sample can produce a similar number of reads for each allele at a given locus. In these variations the ratio of reads will be approximately 1:1. In these variations, the read frequencies for each allele can be around 0.5 of the total number of reads at that specific locus. In many variations the allele frequency for one polymorphism or allele of a heterozygous locus can be greater than about 0.01, 0.05, 0.10, 0.15, 0.20, 0.25, 0.30, 0.35, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.65, 0.70, 0.75, 0.80, 0.85, 0.90, or 0.95. In many variations the allele frequency for one polymorphism or allele of a heterozygous locus can be less than about 0.99, 0.95, 0.90, 0.85, 0.80, 0.75, 0.70, 0.65, 0.61, 0.60, 0.59, 0.58, 0.57, 0.56, 0.55, 0.54, 0.53, 0.52, 0.51, 0.50, 0.49, 0.48, 0.47, 0.46, 0.45, 0.44, 0.43, 0.42, 0.41, 0.40, 0.35, 0.30, 0.25, 0.20, 0.10, or 0.05. In many variations the allele frequency for one allele of a heterozygous locus will be between about 0.44 and 0.56. The allele frequency can be allele dependent and can vary.

In some variations, a diploid sample can be said to be homozygous if one polymorphism or allele at a given locus is greater than about 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, or 0.99, or less than about 0.45, 0.44, 0.43, 0.42, 0.41, 0.40, 0.39, 0.38, 0.37, 0.36, 0.35, 0.34, 0.33, 0.32, 0.31, 0.30, 0.29, 0.28, 0.27, 0.26, 0.25, 0.24, 0.23, 0.22, 0.21, 0.20, 0.19, 0.18, 0.17, 0.16, 0.15, 0.14, 0.13, 0.12, 0.11, 0.10, 0.9, 0.8, 0.7, 0.6, 0.5, 0.4, 0.3, 0.2, or 0.1. In some cases, one polymorphism or allele frequency can be about 0.70 or greater, while the other polymorphism or allele can have a frequency of about 0.30 or lower.

It will be understood that more than two alleles can be measured.

Figure 16:
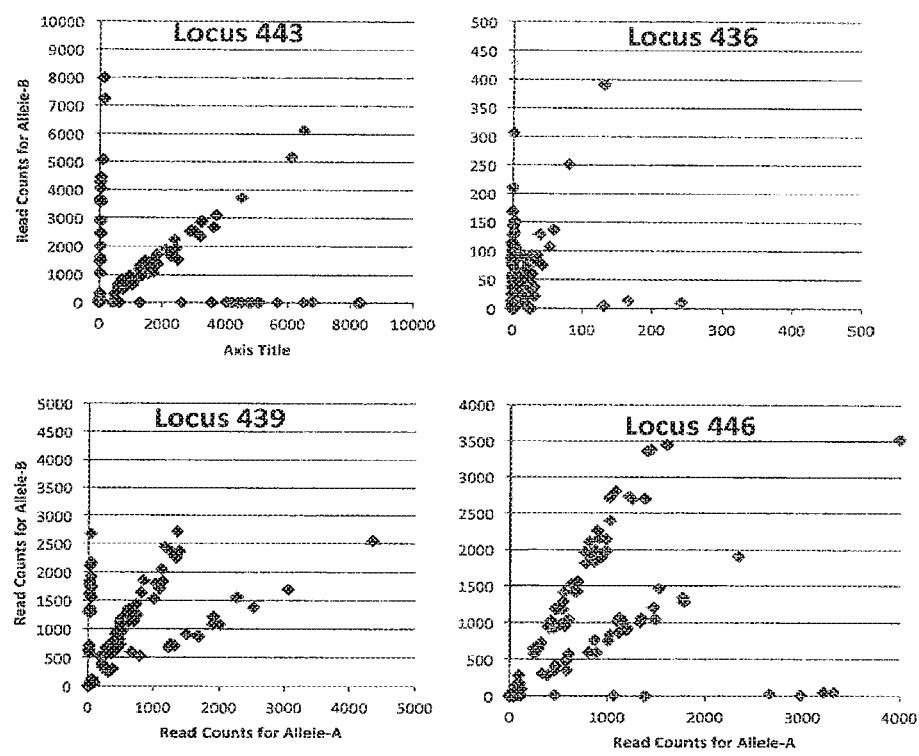
FIG. 16 depicts examples of genotyping data where the data fits the expected genotype frequency ratios, and examples where the data is shifted off the expected genotype frequency ratios.

FIG. 16 depicts examples of genotyping data where the data fits the expected genotype frequency ratios, and examples where the data is shifted off the expected genotype frequency ratios. Locus 443 demonstrates data distribution for samples containing either AA or BB homozygote genotypes that are clustered along the X and Y axis, respectively. Samples containing the AB heterozygous genotype in locus 443 are evenly split between the A and B axis such that the counts for Allele-A are nearly equal the counts for the Allele-B. Locus 436 shows a significant skewing in the sample containing the AB heterozygous genotype toward the Y-axis. Locus 439 shows reads for samples containing the AA homozygous genotype close to the X-axis contains some non-allele A information. Locus 446 shows the same effect but for samples containing the homozygous BB genotype contain some non-allele B information.

For many loci, the data fits the genotype frequency ratio where the homozygotes AA has a ratio at or near 1.0 while samples containing the homozygous BB genotype have a ratio at or near zero. Samples with the heterozygotes AB genotype have intermediate frequencies at or near 0.5.

In some variations, for example, if where a specific locus generates about 1,000 reads, the locus can be scored as heterozygous if one allele generates about 440-560 reads, alternatively the locus can be scored as homozygous if one allele generates from about 700 to about 1000 reads, or the other allele generates from about 0 to 300 reads. In alternative variations, the locus can generate about 10 reads per sample.

In some variations, genotype probabilities can be computed for each locus and each sample. The probability of the most likely genotype for each call (locus by sample) can be used as a call quality score. A threshold can be applied to this call quality score, resulting in "no call" results in situations in which insufficient information is available (likely due at least in part to a random, unusually low number of reads). Genotype probabilities can be computed using Bayes Rule by multiplying the likelihood of having observed the data conditional on each of the three possible genotypes (for example A/A, B/B, and A/B) by the prior probability of each of those three genotypes and then scaling the three products to sum to one. In some variations, the Bayesian prior probabilities are simply the population estimate of genotype frequencies. Under the common assumptions of random mating and other conditions of a population in Hardy-Weinberg equilibrium, the prior probabilities of genotypes A/A, A/B, and B/B can be computed as $p^2$, $2pq$, and $q^2$, respectively, where p and q are the population frequencies of alleles A and B, respectively and p+q=1. In variations in which a pedigreed population is being genotyped, fewer reads can be required by computing genotypes by iterative allelic peeling (Thallman et al., 2001; Thallman, R. M., Bennett, G. L., Keele, J. W., and Kappes, S. M. Efficient computation of genotype probabilities for loci with many alleles. II. Iterative method for large, complex pedigrees. J. Anim. Sci. 79:34-44. 2001). Briefly, the Bayesian approach described is used, but the prior probability is made more informative by conditioning it on the allele counts of the parents and their relatives and mates. Furthermore, the likelihood is made more informative by multiplying the likelihood of the individual (based on the allele counts of the individual) by a likelihood conditional on the allele counts of the progeny and their relatives and mates. The net effect is that, for a given average number of reads, the call rate will typically be higher if pedigree can be considered.

In some cases, such as where the method is used to determine the presence or absence of a polymorphism at a specific target sequence, two sets of first and second complementary polynucleotides can be used. In these variations, two sets of first and second complementary polynucleotides may be used, wherein the two sets may have the same second complementary polynucleotide, and different first complementary polynucleotides. In some variations, the total concentration of the first complementary polynucleotide in each set is 2× that of the second complementary polynucleotide. In some variations, one or both of the first complementary polynucleotides at a specific locus can be unable to discriminate one or both of the target polynucleotides. In some variations, one or both of the first complementary polynucleotides can have different efficiencies of hybridizations and of ligation. In these variations, where the read data may be graphically presented, the read data can be compressed along one axis and the read frequency thresholds adjusted. In some variations a sequencing system can be maximally multiplexed. In these cases, a priori and loci specific modifications will likely be required.

EXAMPLES

The following examples are intended to illustrate aspects of the disclosure, and are not Intended to limit the scope of any description or claims.

Example One: Illumina Sequencing of Product Polynucleotides

Genomic bovine DNA was obtained from either whole blood or bull semen. The target DNA was extracted using either a salt extraction method (whole blood) or proteinase K/organic solvent treatment (semen). DNA isolated from bull semen kindly provided by Dr. Mark Thallman, USMARC, USDA.

Illumina genotyping has previously been used to genotype these specific individuals, using the Illumina BovineSNP50 BeadChip. Those results were made available by Dr. Thallman.

Figure 6:
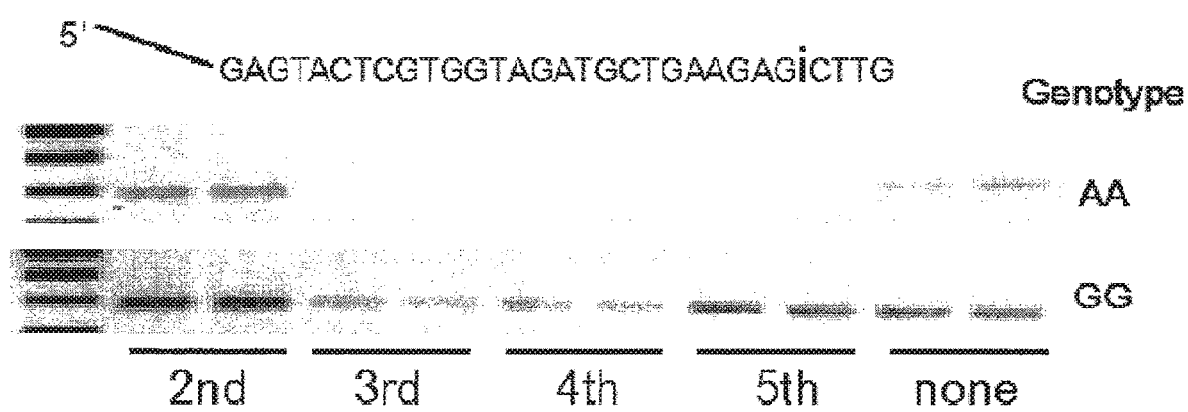
FIG. 6 depicts results from a ligation-dependent assay performed with and without deoxyinosine at various positions 5' of the 3' terminal nucleotide of the first complementary polynucleotide.

First, a single bovine DNA sample was analyzed for eight single nucleotide polymorphisms (SNPs). These specific SNPs were previously characterized in a "weaning weight" study, and were provided by Dr. Thallman. Separate reactions were performed for each target polynucleotide at a given locus. Each first complementary polynucleotide for a given locus was ligated to the second complementary polynucleotide in a separate reaction. Seven of the eight first complementary polynucleotides were able to form G:T mismatches with their target polynucleotides. As discussed below, substitution of deoxyinosine at the third 3' position of the first complementary polynucleotide can aid in preventing potential mismatches resulting in visible product polynucleotides (FIG. 6). Differences in band intensity observed between the different loci sets (for example, loci 192 vs 193) indicate that the polynucleotide sets can require balancing (discussed below).

The second complementary polynucleotides were 5'-phosphorylated and contained an Illumina-specific sequence tag immediately 3' of the second complementary sequence. Illumina sequences can permit the addition of sample-specific sequence tags to the product polynucleotide, as well as a final Illumina sequence required for binding to the sequencing flow cell. Polynucleotides were obtained from IDT, Integrated DNA Technologies (Coralville, Iowa). Polynucleotides were diluted to 1 uM in a 1 mM Tris-HCl (pH=8.3) 0.1 mM EDTA buffer (TE). A final dilution of the polynucleotide was 4 nM in TE.

FIG. 7 depicts a single ligation-dependent assay on eight loci (numbers 192-249) on target polynucleotides from a single diploid sample. For each locus, two pairs of polynucleotides were used (LHS-A, and LHS-B with an RHS common for the given locus). LHS-A and LHS-B are specific for different polymorphic nucleotides representing different alleles at each locus. Ligated polynucleotides, LHS+RHS, were PCR amplified and resolved on an ethidium bromide stained agarose gel and imaged. The previously established allele identities are noted above and the allele identities based on this experiment are noted below. The first complementary polynucleotides contained deoxyinosine when there was potential for a G:T mismatch (loci 193 to 249). All product polynucleotides were not of identical length as it was necessary to vary the length of individual first and second complementary polynucleotides in order to maintain similar annealing temperatures.

After initial characterization described above. DNA samples were collected from 21 individual bovine. Sample DNA was assayed at 24 different loci. The 24 loci were previously identified as part of a "weaning weight" panel. These individual loci are coded 192 to 249.

A 3' nucleotide polymorphism-specific tag was incorporated into the first complementary polynucleotides. In this variation, specific sequence tags were added only to one PCR primer, the right-side primer. In total, 21 individuals were genotyped. One DNA sample was tested in quadruplicate.

DNA solutions were prepared with 200 ng of target DNA in a 5111 volume of TE. The target DNA solutions were initially heated to 98° C. for 5 minutes and then cooled to room temperature.

Hybridization solutions were then prepared by adding 1.5 1l of hybridization buffer (1.5M KCL, 0.3M Tris-HCl pH=8.5, 1 mM EDTA) and 1.51 µl of each polynucleotide, two LHS and one RHS polynucleotides (4 nM each), to the target DNA solution. These hybridization solutions were then heated to 98° C. for 1 minute and incubated at 60° C. After about 4+ hours of incubation the hybridization solution was cooled to 54° C.

A ligation solution was prepared by adding 321 µl of a 1× ligation mix (0.2 U of Taq DNA ligase and the supplied 1× ligation buffer (NEB)) to the hybridization solution. The ligation solution was held at 54° C. for 15 minutes, then heated to 94° C. for 1 minute, followed by rapid cooling to 4° C.

In some cases, a PCR amplification solution was created by adding 4 µl volume of the completed ligation reaction to 21 µl volume of PCR mixture (0.5 Units of Promega GoTaq® Hotstart, with supplied 1× buffer and 0.2 mM each dNTP) along with forward and reverse DNA oligonucleotides (400 nM each). The PCR amplification solution was thermo-cycled (9400 for 5 minutes, then 30 cycles of 94° C. for 10 sec and 650 for 15 sec, followed by a final extension at 72°C for 1 minute and chilled to 4° C.). PCR reactions destined for agarose gel analysis completed an additional 6 cycles.

Some PCR amplification solutions were resolved by agarose gel electrophoresis. These solutions comprised two different samples, one containing the Allele-A LHS and the RHS polynucleotide and the second sample containing the Allele-B LHS and the same RHS polynucleotide. Separating the two samples permitted the similarly-sized product polynucleotides to be resolved on agarose gels in adjacent lanes and genotypes resolved for the locus.

Some PCR amplification solutions were resolved with sequence data from an Illumina sequencing platform. These solutions contained 4 nM of each the LHS-Allele-A, LHS-Allele-B, and the adjacent RHS polynucleotides for each of the 24 loci in the weaning weight SNP panel.

Sample-specific tagging of individual ligated products was accomplished by adding left and right sample-specific sequence tag primers to the PCR amplification solution. The first PCR primers contained 96 different 7 nucleotide sequence tags. The second PCR primers contained up to 96 different 7 nucleotide tag sequences and, in this example, were matched to those used in the first PCR primers for each locus. When less than 96 sample-specific sequence tags were needed, only the right tag set was used. If more than 96 sample-specific sequence tags were needed, then two or more left sample-specific sequence tags could be used to effectively multiply the sample-specific sequence tags as needed.

Sample-specific tagged and completed PCR reactions (one for each ligation reaction) were combined into a single volume. A portion of the combined volume was run out on an agarose gel to visually inspect the average product polynucleotide size which for this polynucleotide set should be around 190 bp (167 to 210 bp), and to estimate the DNA concentration. A suitable portion of the library volume was then cleaned up on a silica based PCR clean up column (Zymo Research, Hayward, Calif.) and eluted into 20 ul TE. A portion of the eluate was examined on a 2100 Bioanalyzer DNA 1000 chip to determine the concentration of the library and to ensure that it was essentially free of PCR primers and their dimers.

A portion of the eluate was denatured, and 5.5 pM was pumped through the assigned lane of the Illumina flowcell and allowed to hybridize to the flowcell's surfaces. Cluster formation and amplification on the cluster station was performed using supplied reagents from a TruSeq Paired End Cluster Kit (Illumina, Hayward, Calif.). The flowcell with the amplified clusters and hybridized sequencing primer was subsequently loaded onto an Illumina Genome Analyzer IIx (GAIIx) where appropriate cycles of multiplexed sequencing data were generated.

Figure 8:
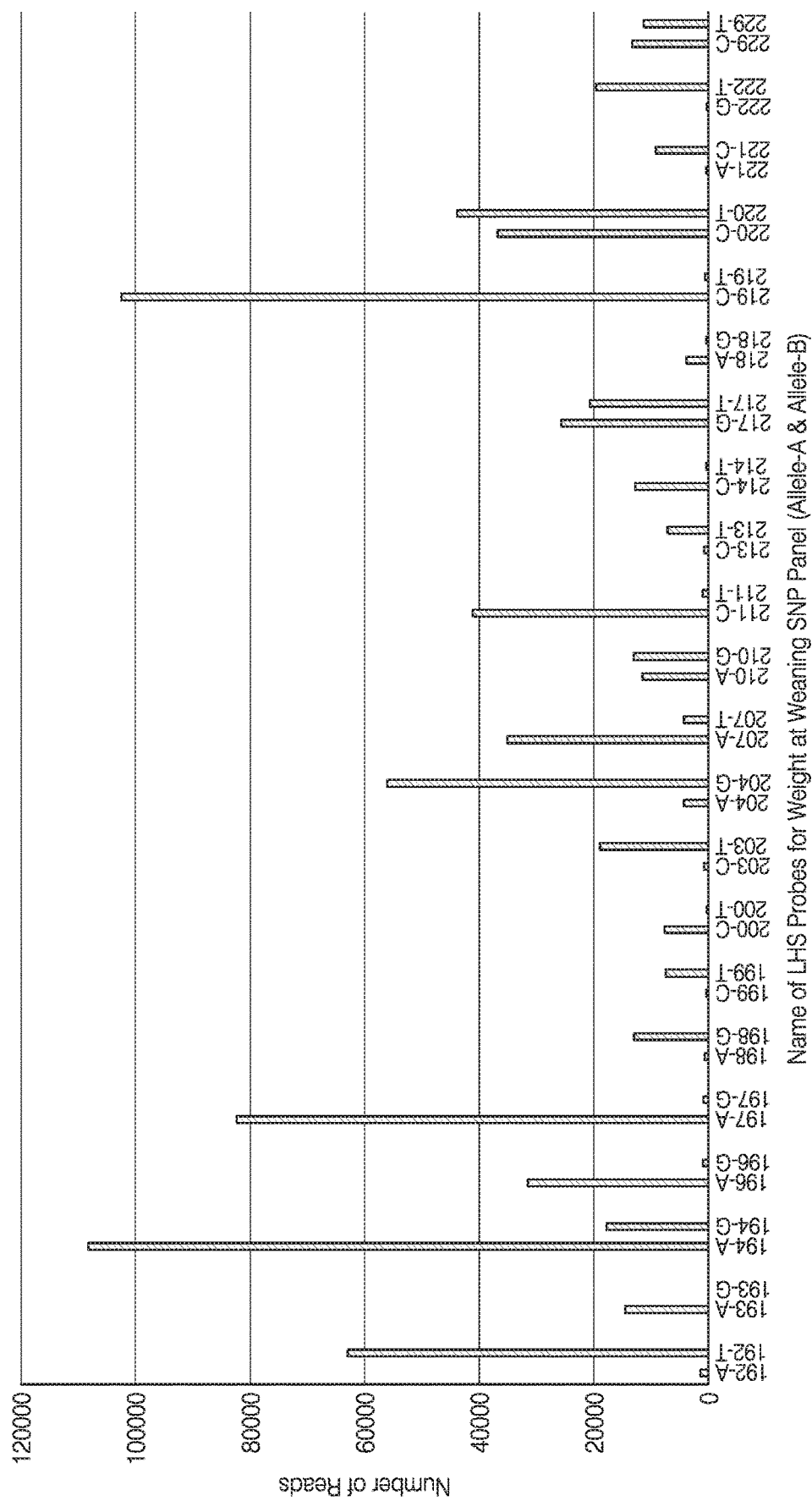
FIG. 8 depicts a bar graph of number of reads versus locus (Allele-A, Allele-B) or (locus×allele) obtained by sequencing the ligation products en masse.

A 36-cycle, indexed sequence data set was generated. After data quality filtration ($4.7 \times 10^6$ failed the filter), $25.29 \times 10^6$ sequence reads were obtained and 120,992 had a sample-specific sequence tag that could not be assigned to a specific Individual. The remaining sequence reads were sorted by the sample-specific sequence tag. Each individual had $1.199 \times 10^6$ reads$\pm$SD $0.194 \times 10^6$. The data (number of reads) was then plotted by the locus and SNP tags for one sample (FIG. 8).

The library of product polynucleotides, in which each sample member was differentially tagged by sequences during the PCR, was introduced into one GAIIx flow cell and clusters produced and 36-cycle, indexed sequence data was generated. The remaining sequence reads were sorted by the sample-specific sequence tags. After data quality filtration ($4.7 \times 10^6$ failed the filter), $25.29 \times 10^6$ sequence reads were obtained and 120,992 had sample ID tags that were unreadable. This is often because the camera cannot resolve overlapping flow cell clusters. Each individual had $1.199 \times 10^6$ reads$\pm$SD $0.194 \times 10^6$. Table I. The data (number of reads) was then plotted by the locus and polymorphism/polymorphism-specific sequence tag (FIG. 5).

TABLE 1

Sequencing read counts for dNTP and dUTP prepared Libraries

|  | dNTP Library | dUTP Library |
|---|---|---|
| Total Reads | $25.29 \times 10^6$ | $25.17 \times 10^6$ |
| Reads per Sample | $1.199 \pm 0.194 \times 10^6$ | $1.094 \pm 0.171 \times 10^6$ |

FIG. 8 depicts the analysis of data produced by the presently disclosed method for a single animal. Product polynucleotides from twenty animals with sample-specific sequence tags were sequenced in a single lane of an Illumina GAIIx flow cell using an indexed 36 cycle single end run. The data was de-indexed and sorted into sample specific sets. A sample's specific reads were then sorted by locus (n=24) and polymorphism call (A, C, G, or T), then the number of reads per polymorphism per locus was plotted. In this example of the presently disclosed method, the polynucleotide sets were not normalized.

Figure 9:
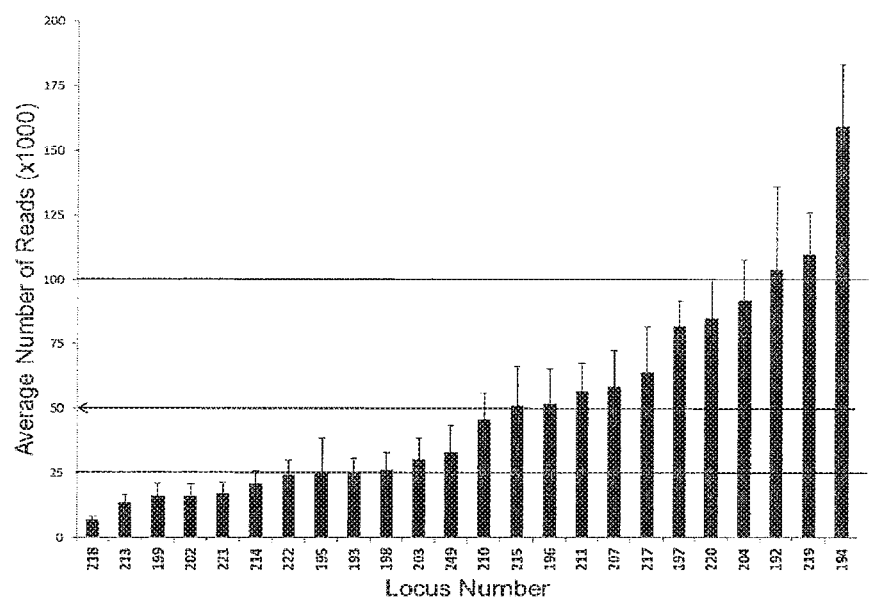
FIG. 9 depicts a bar graph of number of reads versus locus for a single library which contains a total of 24 genomic DNA samples

FIG. 9 shows the average number of Allele-A and Allele-B (summed) reads per locus. Data for 21 genotyped samples is shown. The number of reads for Allele-A plus Allele-B at each locus (for 21 samples) were averaged (bars) with the standard deviations (whiskers), then ranked lowest to highest for clarity. The mean number of reads per locus is 50,639 (horizontal line with left-pointing arrow) with a +2-fold (100K) and −2-fold (25K) lines shown above and below, respectively. This represents our normalization goal where we will attempt to bring the average number of reads per locus into by adjusting the ligation polynucleotide concentrations.

As evidenced by the small relative error bars, polymorphism-specific product polynucleotides were consistent between animals. For example at locus 193, where all animals were of the AA genotype, the recovered A allele tag had a mean count of 24,484+SD 5079.

Two additional issues were identified. First, in some cases the number of reads varies by approximately two orders of magnitude between different polynucleotide sets (FIG. 5: 7,371 to 108,000 reads from expected alleles only). While first and second complementary polynucleotide concentrations were all 4 nM, raising and/or lowering this concentration can aid in providing a more consistent read number. In some cases, changing the first base after the common PCR primer sequence from G to A can lower the output of a particular polynucleotide set. A more consistent read number can aid in analysis of copy number variations.

Figure 10:
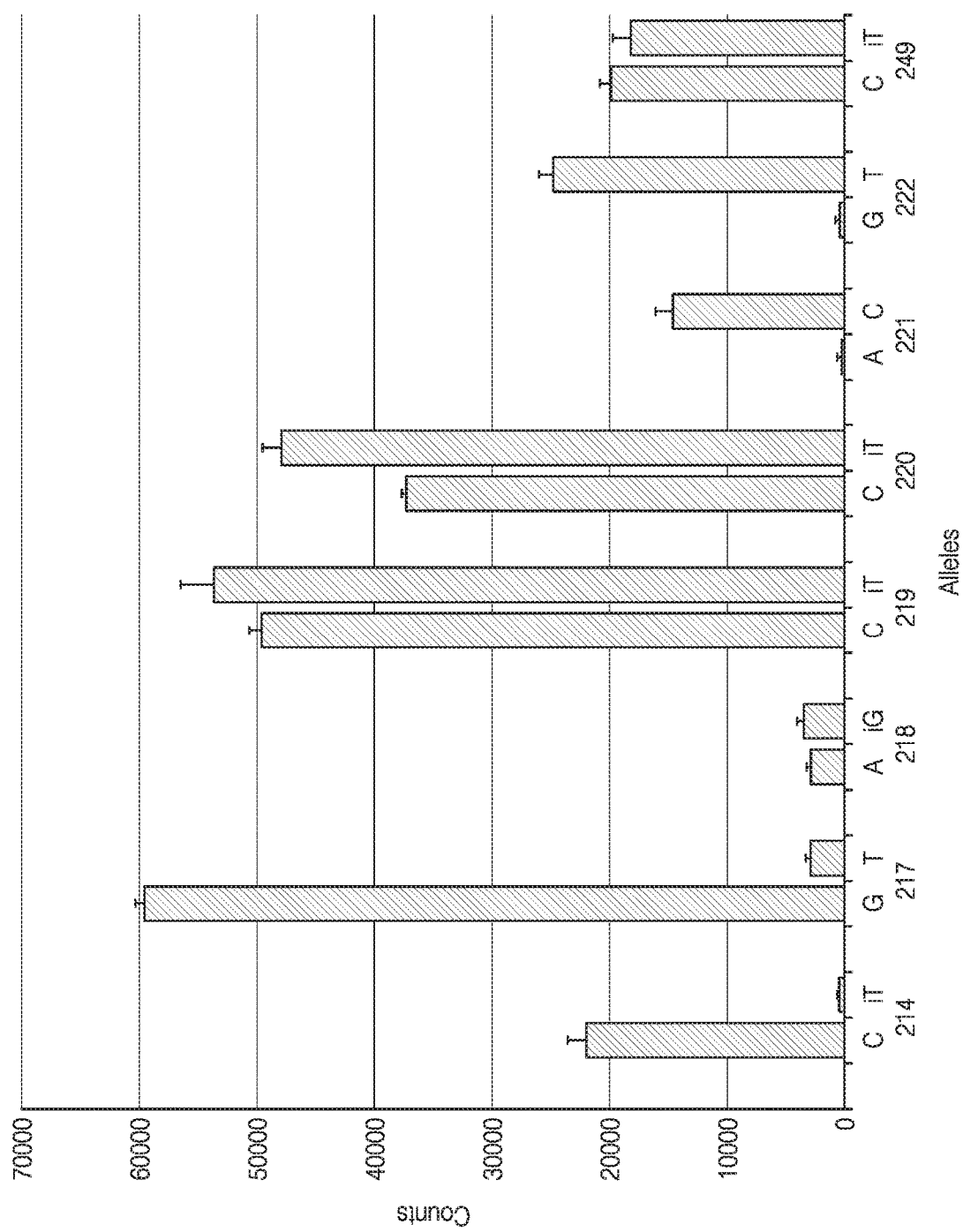
FIG. 10 depicts results for a single sample repeated in quadruplicate within a single MGST (mass genotyping by sequencing technology) reaction. MGST is a type of multiplexed detection sequence technology (MDST). A subset of 8 loci from the 24 loci that were utilized are shown for clarity.

FIG. 10 depicts results for the quadruplicate assay of the commercial sample. In this case, each replicate was given a different sample-specific sequence tag such that each replicate could be distinguished in the sequencing data. The tight standard error bars show the high reproducibility of the assay for this DNA sample.

In FIG. 10 the mean number of sequence reads with each first complementary polynucleotide is shown (bars) with standard errors. The iT and iG refers to the use of the 3rd 3' deoxyinosine base (discussed in more detail below) in the first complementary polynucleotide to reduce the amount of signal occurring due to product polynucleotides produced from ligated polynucleotides with G:T mismatches between the first complementary polynucleotide 3' T or G and the target polynucleotide G or T base, respectively, for the locus indicated.

In some cases, unknown polymorphisms can occur within the first and second complementary polynucleotides. Unknown polymorphisms can hinder polynucleotide binding and reduce the efficiency of proper ligation, with the result of reducing the number of product polynucleotide sequence reads. In the case of known polymorphisms within the polynucleotide hybridization sequences, a universal deoxyinosine can be used and/or the length of the polynucleotide can be increased increase annealing/melting temperature.

Normalization of product polynucleotide output from different polynucleotide sets can aid in reducing the cost of this technique, by allowing more samples to be included into each library. For example, where the polynucleotide sets are not normalized, under-represented alleles can be lost where over-represented product polynucleotides consume flow cell surface area.

In some variations, the presently disclosed method run on a single lane of the GAIIx can be used to assay 10,000 animals for 100 loci. Each lane of the GAIIx can be used to produce 25 to 40 million reads. Newer HiSeq-2000 sequencers from Illumina can have increased capacity and reduced cost. Such increased efficiency can permit even more loci (up to 200 or more) and/or more samples to be analyzed in a single lane.

In some variations, sequence data can be generated for alleles that are not present in the DNA, i.e. false positives are generated. For example in FIG. 8, sequence data collected at locus 192 showed evidence of an A allele (average of 1426 reads). The DNA of the individual used in developing the data in FIG. 8 has a T/T genotype (62821 reads) at locus 194. At loci with the potential for G:T mismatches, sequence reads are being generated from the incorrect LHS polynucleotide ligations even though the animals are homozygous. In most variations, false positives do not prevent accurate estimation/determination of allele frequencies.

Example Two

Determination of Allele Frequency

In some variations, the allele frequency can be estimated by dividing the number of sequence reads of one polymorphism (for example Polymorphism A) by the total number of sequence reads for that locus (which, for example can include a Polymorphism A and Polymorphism B)

Freq of Polymorphism $A$=(Number of Polymorphism $A$ sequence reads)/[(Number of Polymorphism $A$ sequence reads)+(Number of Polymorphism $B$ sequence reads)].

In most cases, samples from individuals that are heterozygous at a given locus can produce a similar number of sequencing reads for each polymorphism or allele at that locus. In these cases, the frequencies for both polymorphisms can be about 0.5. For example, heterozygous loci 218, 219, 220, and 249 had read frequencies for one polymorphism of 0.45, 0.48, 0.44 and 0.52, respectively (FIG. 10).

For some samples from individuals that are homozygous at a given locus, the frequency of one polymorphism or allele can be 0.70 or greater, and the frequency of the other non-present allele can be 0.30 or lower.

In some cases, read frequencies of about 0.5/0.5 and ≤0.3/≥0.7 can be used to determine the genotype of a given locus (here, heterozygous and homozygous, respectively.

Frequency cutoffs can be used when examining the data. For example, read frequency can be used to determine zygosity of a given locus from a given sample, where the zygosity has not yet been determined. For example, for a given locus with two possible polymorphisms or alleles, a read frequency for one of the possible polymorphisms of ≥0.7 and/or ≤0.3 can indicate homozygosity, and a frequency of between about 0.44 and 0.52 indicate heterozygosity.

In some cases, genotype probabilities can be computed by multiplying the likelihood of having observed the data conditional on each of the three possible genotypes by the prior probability of each of those three genotypes and then scaling the three products to sum to one. In the event, we consider each individual independently, the prior probabilities are simply computed ($p^2$, $2pq$, and $q^2$) from estimates of the population allele frequencies (p and q=1−p). We can gain power (or require fewer reads) in cases where we can take into account genotype probabilities of relatives to compute a prior probability that is more informative before multiplying by the likelihood.

Figure 11:
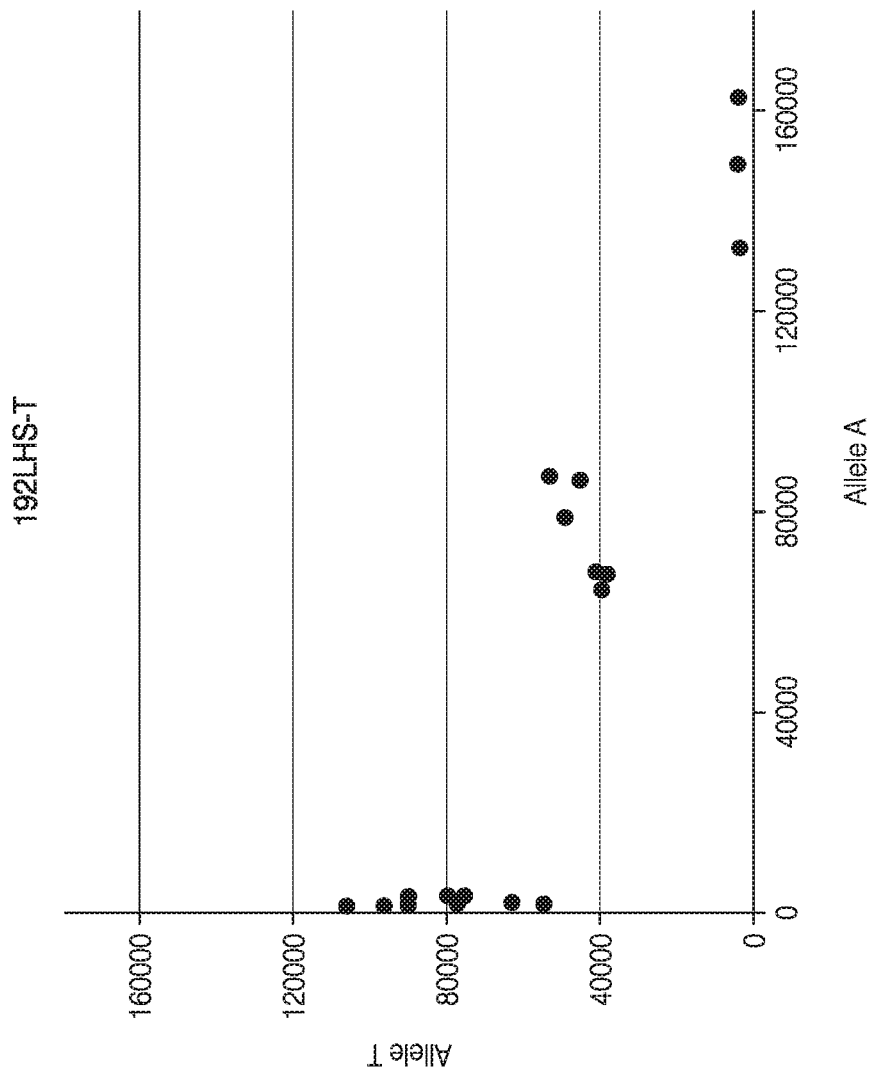
FIG. 11 depicts four dot plot graphs used for visual analysis of MSGT data for four single loci.
Figure 11:
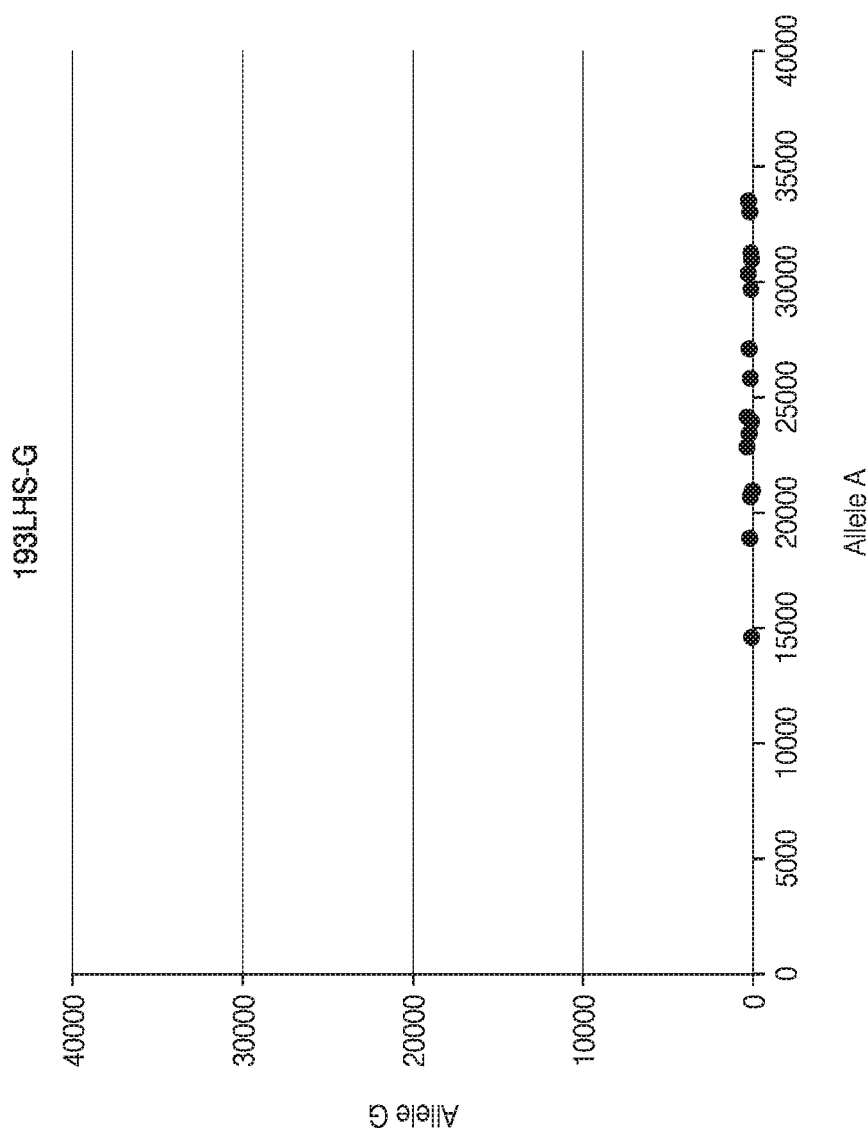
Figure 11:
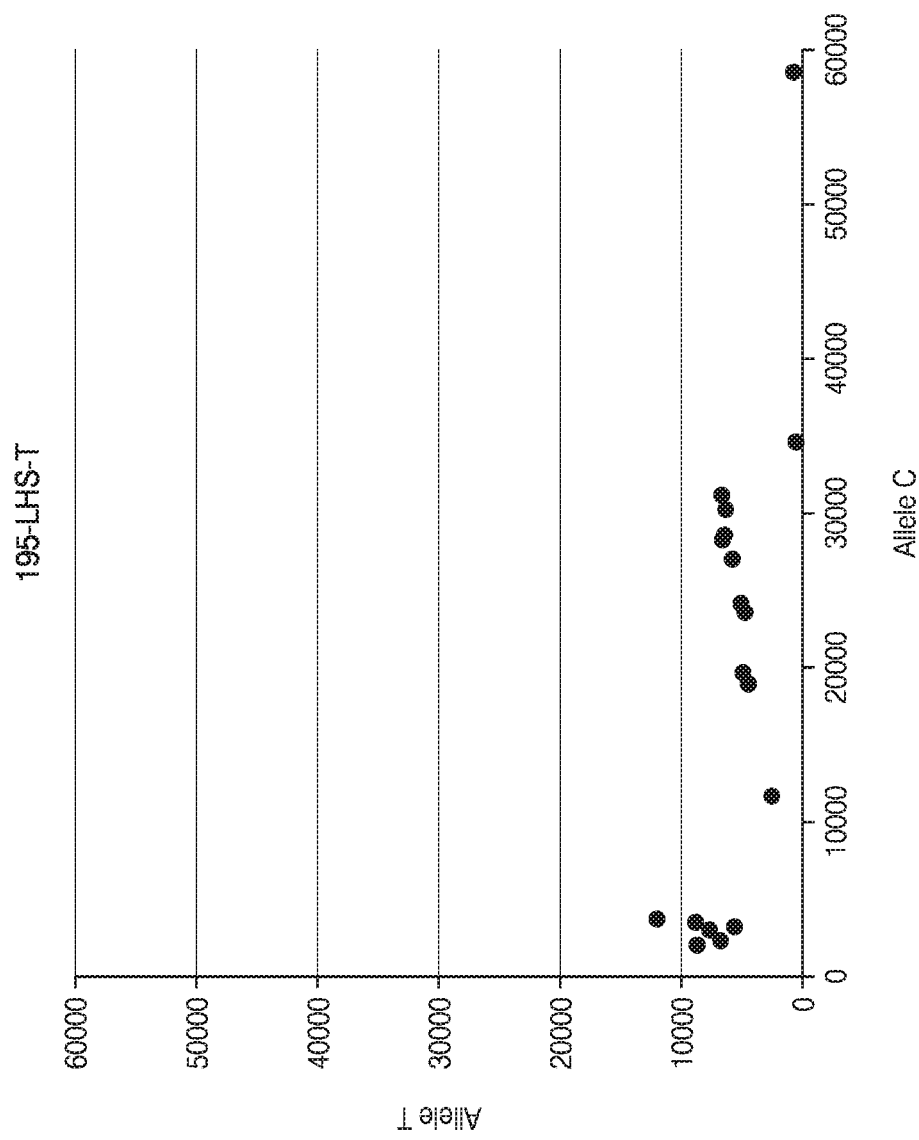
Figure 11:
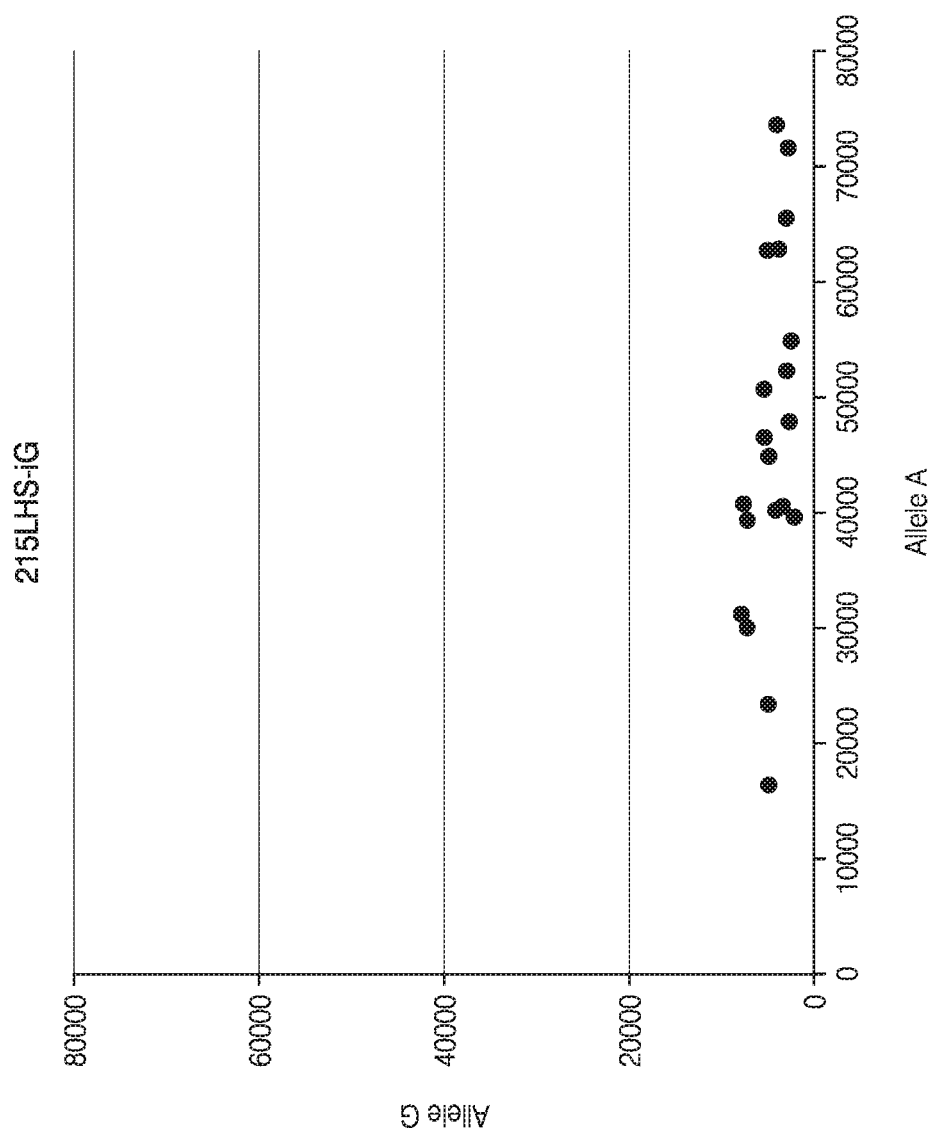

FIG. 11 depicts analysis of loci SNP-220 (polymorphisms C and T; FIG. 11A), and SNP-215 (polymorphisms A and G; FIG. 11B) loci. 19 samples were plotted as dots, with each sample represented by a dot. The horizontal axis is the number of T and A sequence reads for the 220 and 215 loci, respectively. The vertical axis is the number of C or G sequence reads for the 220 and 215 loci, respectively. For locus 220, the plotted data points fall into three groups: homozygous samples (CC or TT) cluster along the vertical and horizontal axes, respectively; and heterozygous samples (CT) cluster diagonally. FIG. 11B depicts a failed polynucleotide set, locus 215. All sequence reads for locus 215 cluster along the horizontal axis, polymorphism G. Although 7 animals were previously determined (via Illumina Bovine SNP50 BeadChip) to be heterozygous for locus 215, the first complementary polynucleotide LHS-G failed and does not produce product polynucleotides with equal efficiency to the LHS-A polynucleotide.

In the case of the data depicted in FIG. 11A, the read frequency cut-offs of ≤0.3 and ≥0.7 can be used to determine the genotype of the sample. FIG. 11B depicts data plot for an assay that did not properly discriminate alleles, wherein data points compressed along one axis. In this case, it may be necessary to adjust read frequency cut-offs.

FIG. 11C-F depict several single loci. SNP-192 (with polymorphisms T and A), is shown in FIG. 11C. The number of sequence reads with the T and A first complementary polynucleotides were plotted for 19 samples as in FIGS. 11A and 11B. These data, like locus 220, cluster into three genotype groups; homozygous sample (TT or AA) along the two axes, and heterozygous samples (TA) on a diagonal, down the middle. For locus 193 at FIG. 11D, (polymorphisms G and A) all samples were homozygous for polymorphism A, and the data are clustered along the x-axis. For locus 195, depicted at FIG. 11E, the number of sequencing reads for the first complementary polynucleotide, with polymorphism T, were approximately three-fold lower than the number of sequence reads obtained for the first complementary polynucleotide with the C polymorphism. For locus 215, FIG. 11F (with polymorphisms G and A) the data is clustered along the X-axis, this can signify that the first complementary polynucleotide with polymorphism G has failed.

Example Three

Universal Base to Decrease False Positives

In some cases, genotyping can misidentify G and A OR C and T polymorphisms. This can be caused by partial hydrogen bonding between the two nucleotides of a basepair. In some variations, G:T and T:G basepairs between the 3' nucleotide of the first complementary polynucleotide and the polymorphism in the target polynucleotide can permit ligation, despite the mismatch. In these variations, despite a mismatched basepair, the first complementary polynucleotide and second complementary polynucleotides can be ligated and subsequently amplified. In some variations, production of a product polynucleotide resulting from G:T mismatches can be minimized by adding a universal base, for example, deoxyinosine, to the first complementary polynucleotide. The universal base can be added proximal to the 3' nucleotide of the first complementary polynucleotide. In these variations, the first complementary polynucleotide comprising a universal base can be destabilized such that basepair mismatch between the polymorphic nucleotide of the target polynucleotide and the 3' nucleotide of the first complementary polynucleotide will aid in reducing ligation of a first complementary polynucleotide, with a mismatched 3' nucleotide, and a second complementary polynucleotide.

As mentioned above, FIG. 6 depicts use of a universal base to reduce the occurrence of product polynucleotides resulting from a first complementary polynucleotide with a 3' nucleotide mismatch to the polymorphic nucleotide on the target polynucleotide. As shown in FIG. 6, positioning inosine 5' of the 3' nucleotide can aid in reducing occurrence of a ligation event in these cases. Positioning inosine at the $3^{rd}$ position may reduce these mismatched ligation events more than positioning inosine at the 2nd position. The product polynucleotides of FIG. 6 were resolved on an ethidium bromide stained agarose gel and imaged.

Example Four

Uracil Incorporation

In some variations, laboratory space can be contaminated with previously produced product polynucleotides. In these cases, previous product polynucleotides can contaminate subsequent experiments and their analysis. In some variations, dUTP (2'-Deoxyuridine, 5'-Triphosphate) can be partially or fully substituted for dTTP in the amplification reaction.

In some variations, Uracil-DNA glycosylase (UNG) can be added to the amplification step. In some variations the presence of the UNG enzyme can digest polynucleotides containing uracil nucleotides. In these variations, the UNG enzyme can be denatured by incubating the enzyme at high temperature. In some variations, the first step of an amplification can denature and de-activate the enzyme. In most cases, after de-activation the UNG enzyme cannot digest polynucleotides containing uracil. In these variations the amplification step can include a 15 minute incubation at 37° C., which can permit the UNG enzyme to digest dUTP-containing product polynucleotides. In these variations, a subsequent 94° C., 5 minute incubation can be used to de-activate the UNG enzyme.

dUTP containing polynucleotides were prepared as described in Example One. Amplified polynucleotides were prepared from the ligation reactions. A portion (20%) of the completed amplification reactions were separated by electrophoresis on a 2% agarose gel to confirm the expected product polynucleotides. One sample did not produce the expected 200 bp band. All the remaining amplification reaction volumes for the dTTP library or for the dUTP library were then combined, cleaned-up and quantitated for use as a sequence data generation library. In this reaction the dNTP mix was replaced by a mix containing dUTP rather than dTTP. The purpose of the dUTP library was to demonstrate that dUTP libraries could be used in the presently disclosed method. This would permit a UNG step to be incorporated into the PCR reaction so that potential LD-PCR product polynucleotides contamination could be minimized.

The dUTP library required a non-hotstart Taq polymerase mix rather than the proof-reading Phusion mix prescribed by the manufacturer. The dUTP library had $25.17 \times 10^6$ sequence reads with each sample having $1.094 \times 10^6$ reads±SD $0.171 \times 10^6$.

PCR amplification can then be used to create novel dUTP containing product polynucleotides from newly ligated LHS and RHS polynucleotides.

Figure 12:
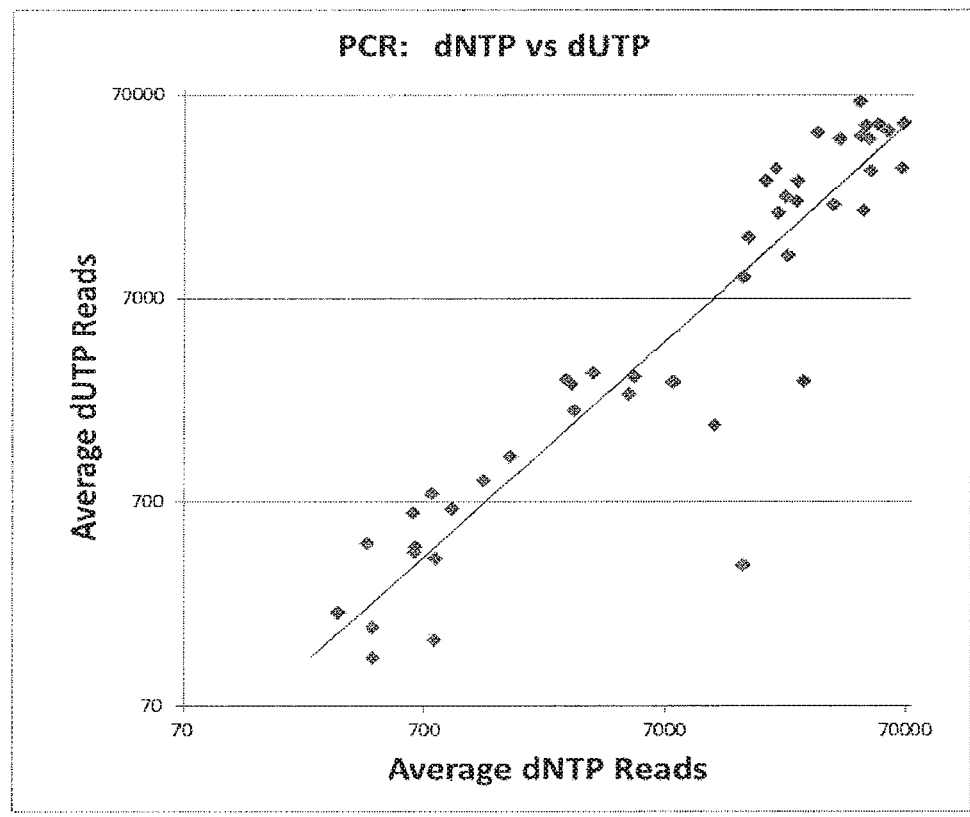
FIG. 12 depicts a comparison of the number of reads per locus obtained from the dNTP vs the dUTP prepared libraries for the bulk sample.

FIG. 12 demonstrates that the effect of dUTP use in amplification are minimal as the number of reads can be only slightly less than when dNTP was utilized. Failed loci were excluded from analysis, and the presently disclosed method repeated with a dUTP containing library. Amplification reactions comprising dUTP and dTTP were in agreement with each other and the previously obtained genotyping data (418/418). This indicates that dUTP libraries are suitable for use in the presently disclosed method and will be an effective method to prevent product polynucleotide contamination in the library. FIG. 12 compares the number of reads obtained from the dNTP vs the dUTP prepared library for the bulk sample. For each allele the average number of dNTP vs dUTP reads obtained from the four replicates were plotted and a line of best fit determined ($y=0.3683 \times 1.058$, $R^2=0.088$).

Example Five

Relationship of Reads/Locus and Specificity/Stability.

Three sets of computational experiments were performed. Data was obtained by performing the presently disclosed method as described above. Data was re-sampled 1000 times. Re-sampling resulted in 10, 20, or 30 reads obtained for each locus/individual combination (n=418). After application of genotype calculation and its cutoffs (0.70><0.30), genotypes were determined for each data set (418×1000×3). For each sample, locus and read number (10, 20, or 30 reads), the specificity of the genotyping approach was determined by computing the proportion of experiments (out of 1000) where the observed and expected genotypes were in concordance.

Figure 13:
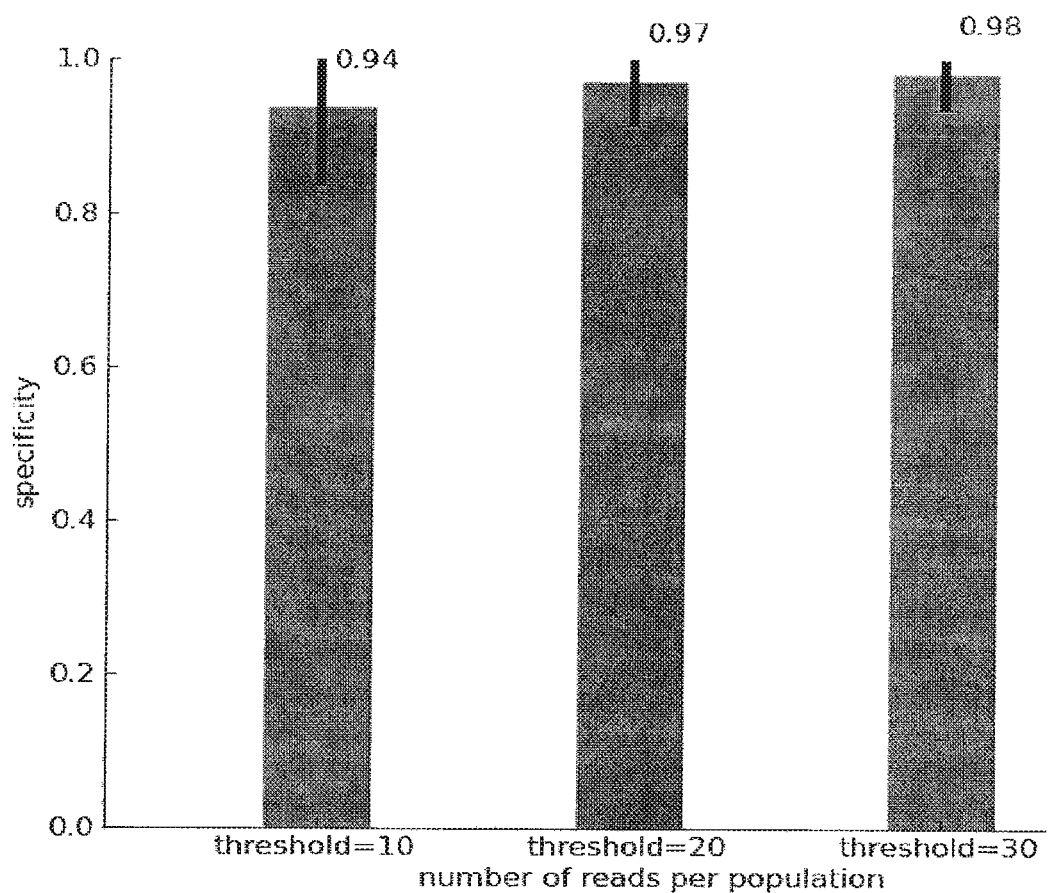
FIG. 13 depicts specificity of genotyping by the presently disclosed method from data resampling analysis.

FIG. 13 depicts specificity of genotyping by the presently disclosed method from data resampling analysis. The mean specificities (bar) are shown with standard deviations (line).

Variability (or stability) of the presently disclosed method was determined by observing variation in computed specificity proportions across all loci+animal+read number combinations. As depicted in FIG. 13, Increasing the number of reads per locus/individual combination improved the specificity and reduced variability. The rate of improvement as a function of number of reads can diminish as the number of reads increases. Locus-specific rules and a priori genotype frequency information will be required to improve the specificity and stability with low read numbers. For example, with 30 independent sequencing reads, the accuracy reaches approximately 98%.

Example 6

Routine genotyping of cattle is currently prohibitively expensive. Many fields in agriculture need an inexpensive high throughput method to provide flexible low-density genotyping. We demonstrate the feasibility of inexpensively genotyping cattle, using a novel combination of highly multiplexed ligation-dependent PCR (LD-PCR) combined with high throughput next generation sequencing (NGS) technology. We call this a mass genotyping by sequencing technology (MGST). The MGST has the potential to be highly multiplexed in terms of the number of SNP positions to be typed as well as the total number of animals that can be combined in a single assay run. MGST has the potential to be fully automated and could be offered as a very inexpensive service. Most of the cost is actually the DNA extraction process. Our results suggest that MGST has the capacity to accommodate at least 100 SNPs and upwards of 10,000 animals per assay run (single lane) of the Illumina NGS devices. We have designed two genotyping panels that interrogate 24 and 113 publically available SNPs in cattle. We would also explore other genotype panels, such as genetic defects and qualitative traits, which would be of great use for the agriculture industry.

Figure 17:
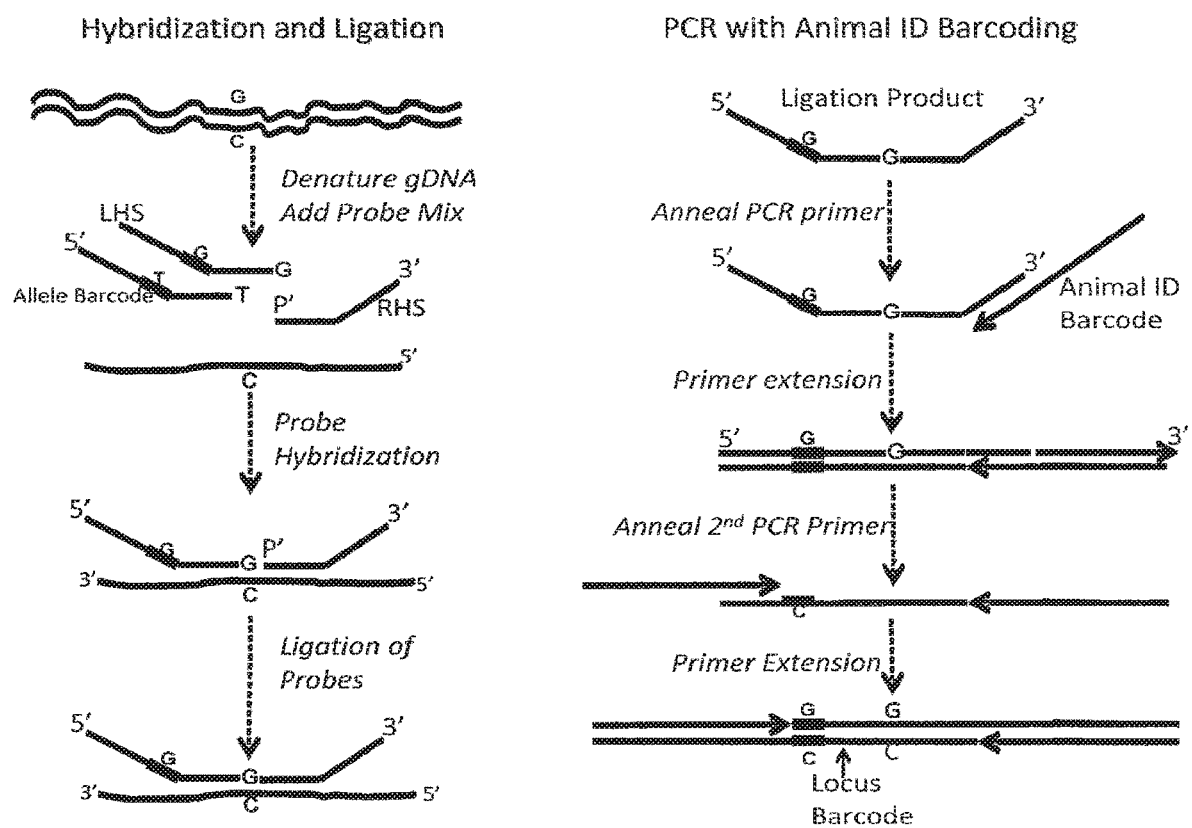
FIG. 17 depicts MGST combining multiple LD-PCR assays each at different loci.

With reference to FIG. 17, an example is shown of MGST combines multiple LD-PCR assays, each at different loci, permitting multiple animal samples to be genotyped within a single sequencing library. We have two SNP panels consisting of 24 SNPs from the Illumina BovineSNP50 Bead-Chip and another 113 SNPs for parentage and tenderness associated polymorphisms. For any given loci there are two types of probes, the left hybridization sequences (LHS) and the right hybridization sequences (RHS). For the LHS, there are two genotyping probes that differ in the last 3' nucleotide which is complementary to the SNP to be interrogated. The LHS probes also contain a short "Allele Barcode" that further differentiates one LHS from its partner. This also permits the allele information to be determined from short sequencing reads. (Barcodes as used herein are also referred to as tags.) The RHS probes are immediately adjacent the LHS and are 5' phosphorylated (P') so that a DNA ligase can ligate the LHS to the RHS. Only successfully ligated LHS and RHS probes can be amplified by the common PCR primers by means of common sequences that tail the LHS and RHS probes (diagonal lines on the LHS and RHS). Each animal's gDNA sample (25 to 200 ng) is processed in a single reaction tube for the probe hybridization and ligation steps while a subsequent PCR step adds an animal specific sample ID barcode to the ligation products. After the sample specific PCR, the reaction products are combined forming a single sequencing library. The libraries (6 pmol) are introduced into a lane of the Illumina GAIIx flow cell. After clustering on the flow cell, a single end with 36 reads is performed plus an additional barcode read. The first 5 bases read, determine the allele from the allele barcode engineered into the LHS probes. The subsequent bases determine which locus is being read while the animal ID is determined in a separate barcode read. The raw data is passed through the Iliumina quality control filter and then binned according to the animal ID barcode. Each animal's data is then binned according the locus barcode. Each locus is then binned according to one of the two allele types (Allele A or B). For each locus the read counts can then be used to determine the observed frequency according the formula Freq=Counts A/(Counts A+Counts B). Animals with near 1.0 frequencies are of the AA genotypes while animals with near 0.0 frequencies are of the BB genotypes. AB heterozygote animals have intermediate allele frequencies of ~0.5. Data can be plotted by these frequencies and clusters of AA, AB, and BB animals observed and compared to the expected genotypes as determined by the Illumina BovineSNP50 chip results. We have an automated pipeline that can call the genotypes based on a k-means clustering system.

Figure 18:
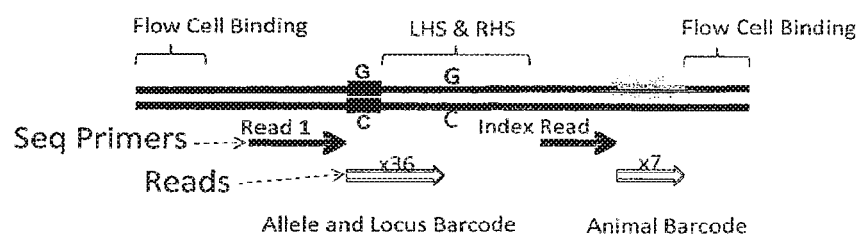
FIG. 18 depicts an exemplary sequence format of a sequencing library.

With reference to FIG. 18, members of an exemplary MGST sequencing library have a sequence format. The original LHS and RHS probe sequences that were joined by ligation are bounded by Illumina specific sequences that permit 'Flow Cell Binding'. Each LHS has an addition short allele barcode (thick grey bars G/C) that encodes the allele information. By placing the allele barcode information in this location, the "Read 1" does not need to extend into the site where the actual SNP is positioned (the junction of LHS and RHS). Read 1 begins with the sequencing of the allele barcode and then picks up the LHS sequence which is in essence the locus barcode. A short index read (7 to 8 bases) determines the sample specific animal ID barcode.

Figure 19:
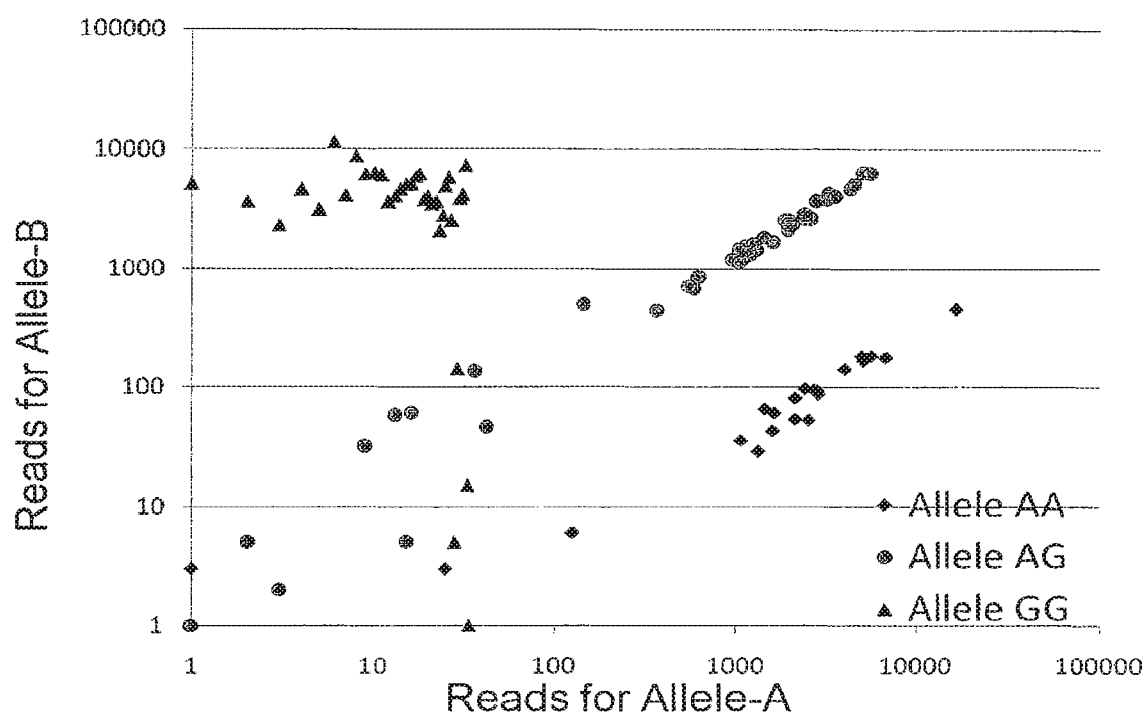
FIG. 19 depicts exemplary NGS data.

With reference to FIG. 19, exemplary NGS data is shown. For Run 115, the read count data for Allele-A vs Allele-B was plotted for a single marker (rs17870274). Three discrete groupings are apparent, reflecting the AA, AB, and BB genotypes for this locus. The genotypes established by the Illumina BovineSNP50 BeadChip are shown. For some animals the total number of reads for the Allele-A plus Allele-B were significantly below the mean number of reads obtained (3700). In this particular experiment several reaction wells had evaporated during hybridization resulting in the loss of those samples and the below mean read counts.

Table 1 depicts MGST Runs Performed. SNP Panels, panel-24 (P24), Parentage & Tenderness panel (PPTP). Failed loci are those where the groupings for the genotypes cannot be resolved. Two lanes in run 106 were performed with either dNTP or a dUTP nucleotide mix. The use of dUTP during library construction permits a uracil-n-gylcosylase based anti-contamination system to be used. *Sequence based non-calls have not been excluded.

Figure 20:
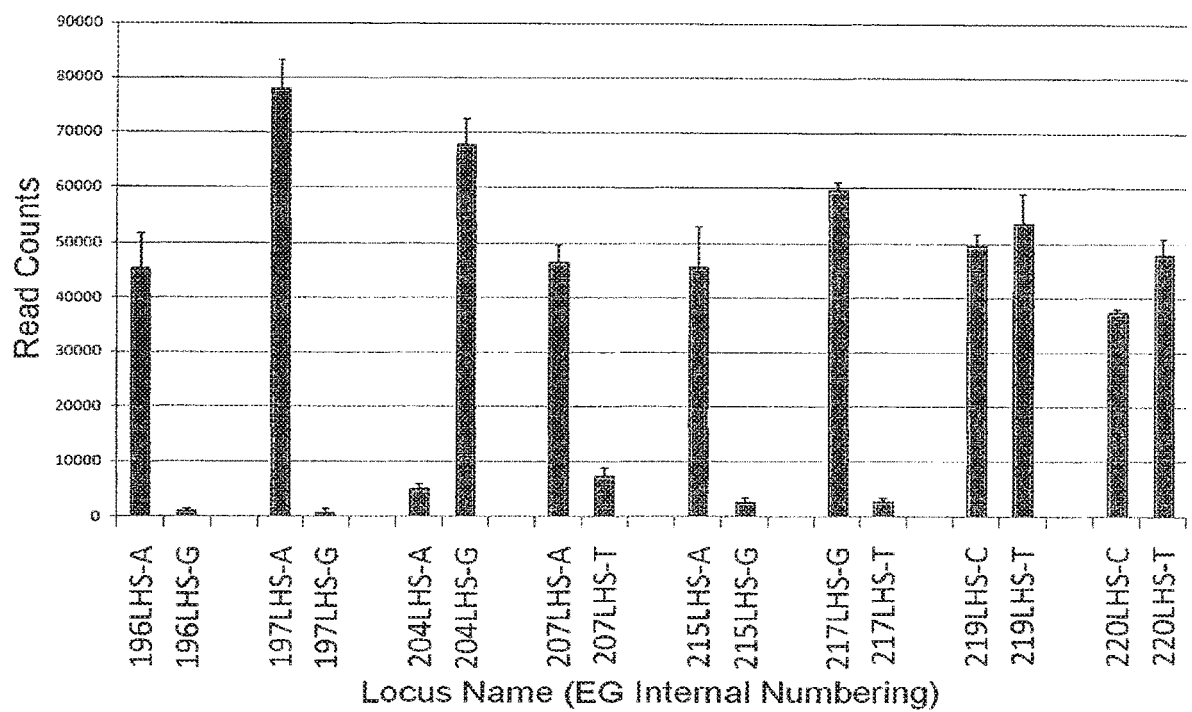
FIG. 20 depicts an example of the reproducibility of NGS data.

With respect to FIG. 20, an example of the reproducibility of NGS data is shown. For Run 106/dNTP, one animal was included as four replicates in the library. The mean number of reads (bars) with standard deviations (whiskers) are shown for a subset of the 24 loci that were assayed. The homozygous (196, 197, 204, 207, 215, 217) and heterozygous (219, 220) genotypes are apparent.

Figure 21:
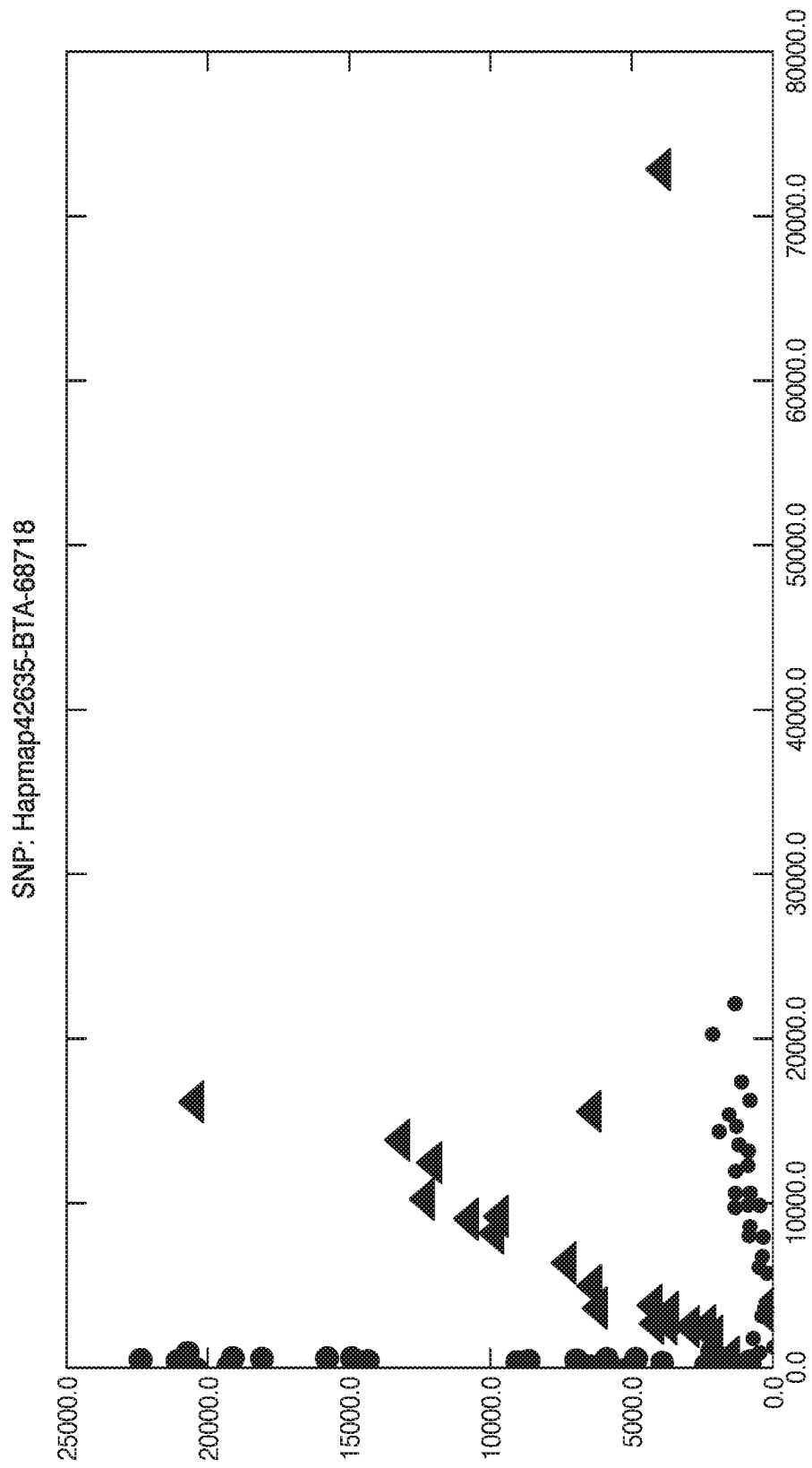
FIG. 21 depicts exemplary automated genotyping.
Figure 21:
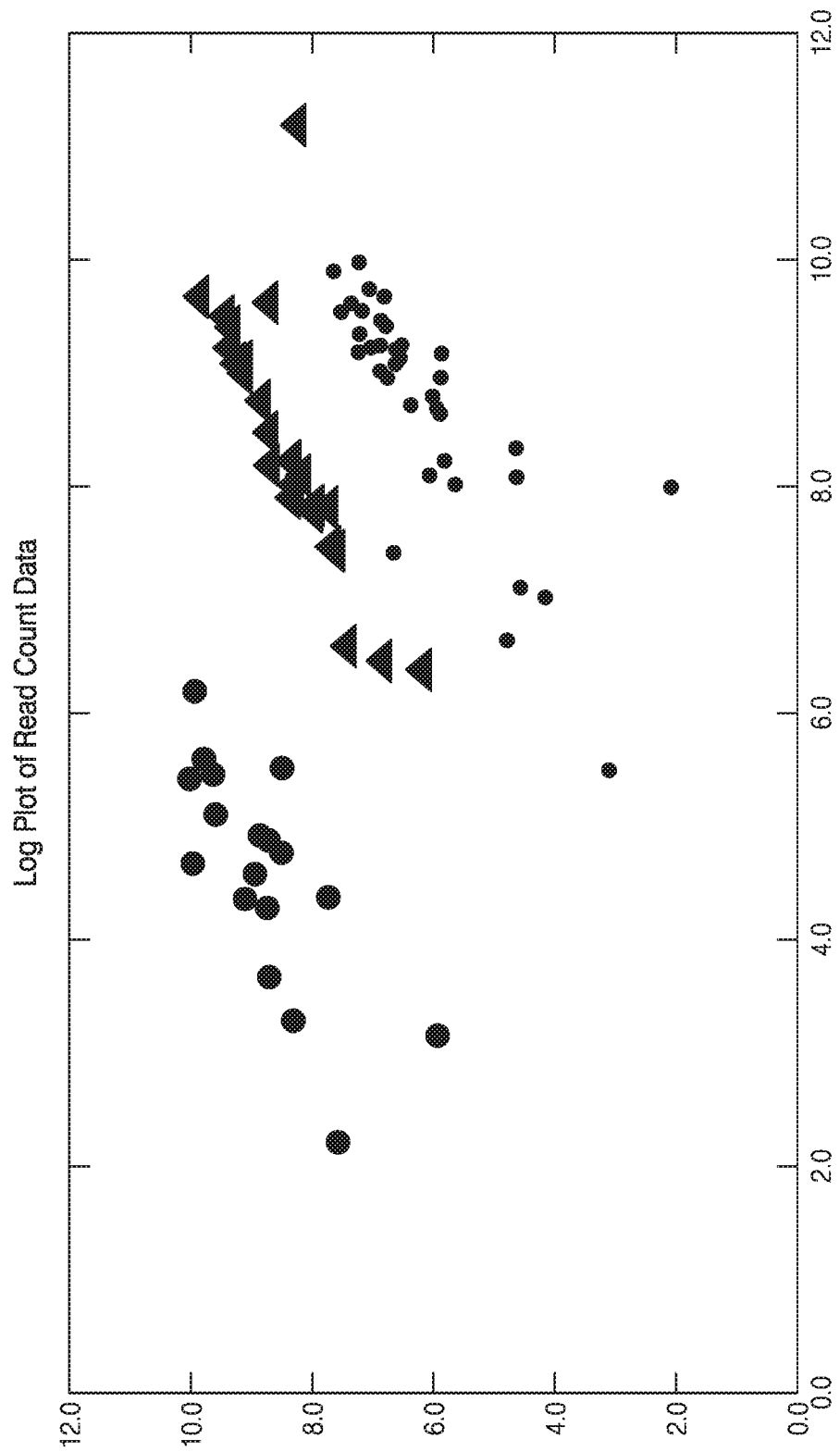
Figure 21:
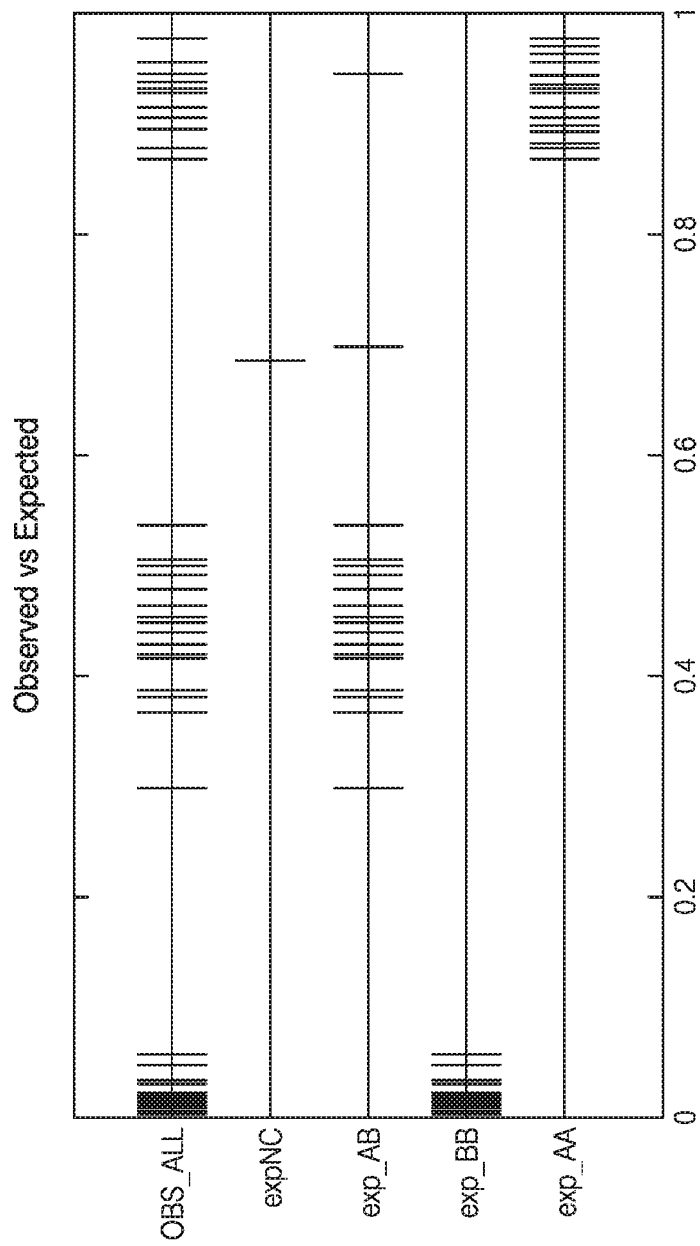

With respect to FIG. 21, exemplary automated genotyping is depicted. Our automated pipeline uses a k-means clustering approach to partition the number of observed sample points into its appropriate genotype category based on the observed frequency [Freq=(reads Allele-A/(reads Allele-A+ reads Allele-B)] for each 'sample×locus' combination. A simple input file with the established genotypes (from Illumina BovineSNP50 BeadChip data) (homozygous AA, BB or heterozygous AB) is provided to a pipeline as validation data. The pipeline then runs k-means clustering on this dataset and analyzes the clusters for accuracy and quality of clustering. The pipeline's genotype calls are compared to the validation genotypes calls and the concordance determined. If the validation data contains non-called datapoints (ex-pNC) they are excluded from concordance analysis. The pipeline currently produces genotype calls for all animal× SNP combinations for which BovineSNP50 genotypes exist. Some discordances are therefore due to low numbers of reads or other conditions which will more appropriately be classified as no-calls in future versions of the pipeline. The results can be viewed graphically in the form of plots or textual format (data from run 118 is shown).

Figure 22:
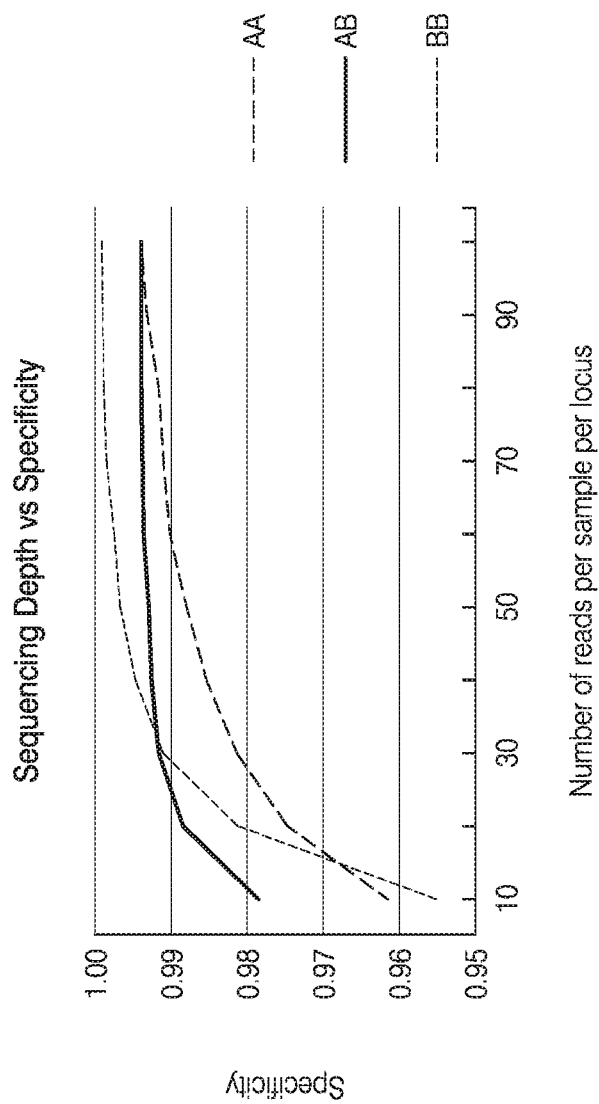
FIG. 22 depicts exemplary data resampling analysis.
Figure 22:
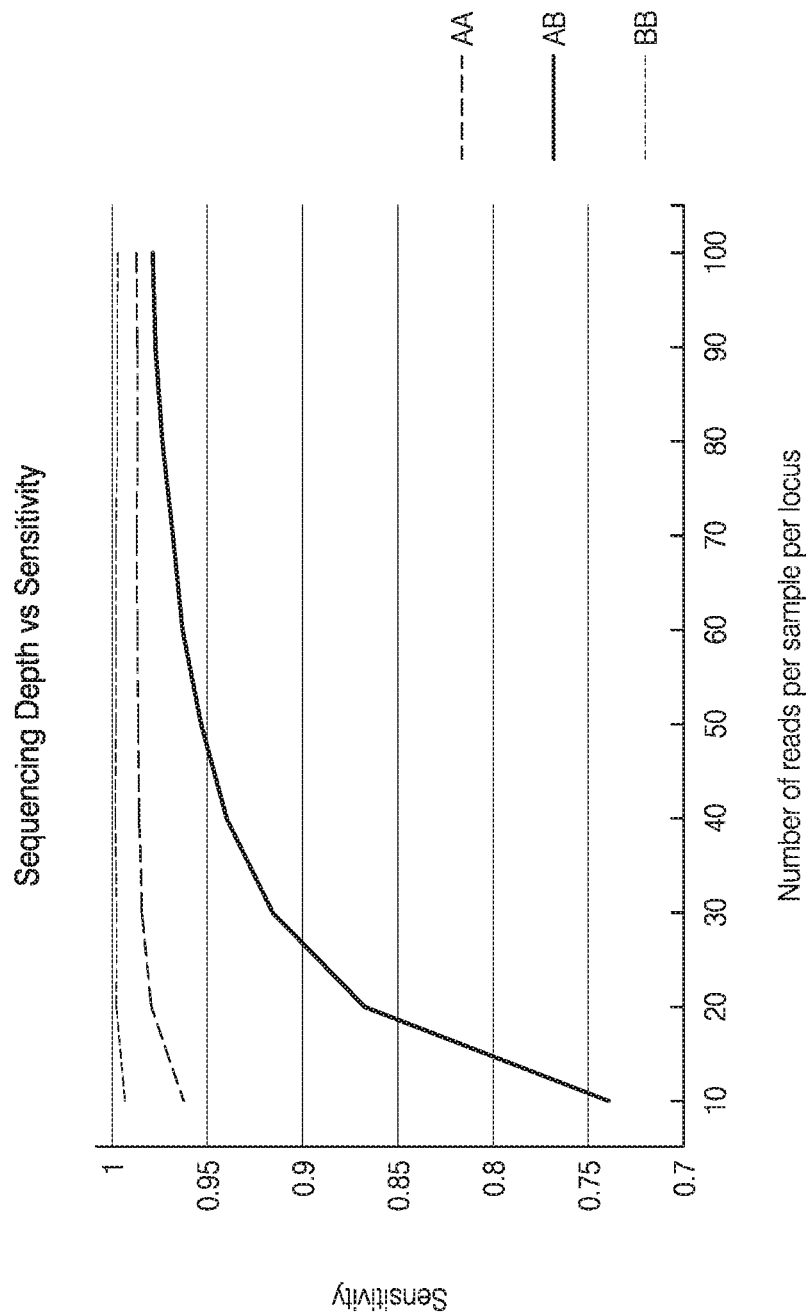
Figure 22:
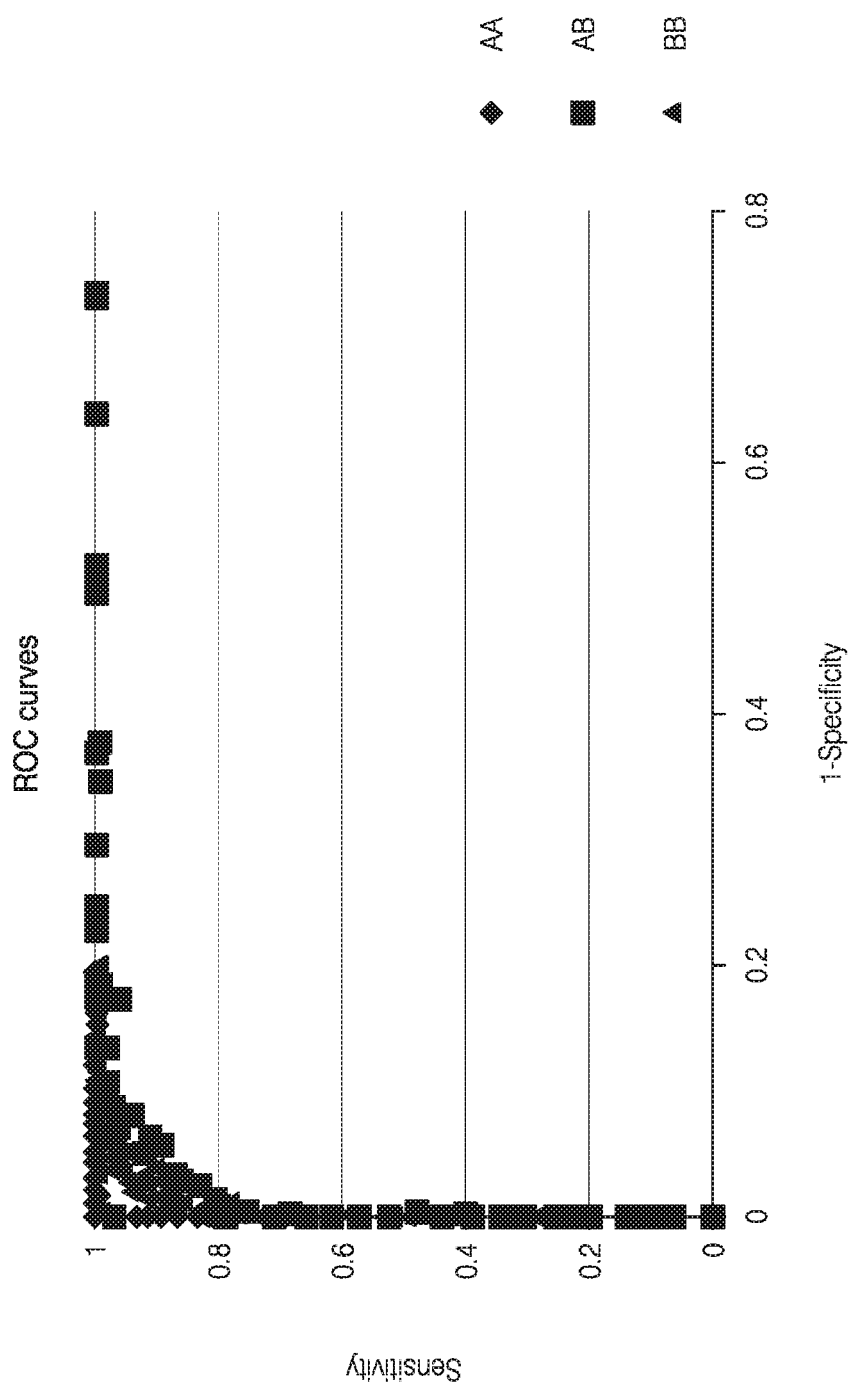

With respect to exemplary FIG. 22, exemplary data resampling analysis is depicted. In order for the MGST technology to be viable when 10,000 animals across 100 loci are used in a single assay, the genotype assignment method needs to be both sensitive and specific when the number of reads per animal per locus is very constrained. The validation assay presented here has orders of magnitude higher coverage per animal per locus than what is expected for the actual production-grade agricultural assay services. In order to explore the feasibility of accurate genotype identification under low read conditions, we have performed extensive re-sampling simulations.

The simulation was set up in the following manner. An implementation of Marsenne twister pseudorandom number generator was used to resample the reads from each animal and each locus until a desired sample size was obtained. A total of 10,000 random re-sampling experiments were performed with sample sizes of 10, 20, 30, 40, 50, 60, 70, 80, 90, and 100 reads per animal per locus. Each re-sampled animal-locus combination was assigned a genotype of AA, AB, or BB based on the frequency thresholds defined from the full data set (typically 0 to 0.33 for BB genotype, 0.33 to 0.66 for AB genotype, and 0.66 to 1 for AA genotype).

Sensitivity, specificity, and ROC curves were computed separately for each genotype (AA, AB, and BB). The average sensitivity and specificity (across all 10,000 simulations) is shown in the table above. At the lowest sample size of 10 reads per animal-locus, the sensitivity of the MGST is less than 75% for heterozygote but greater than 95% for both homozygous and the specificity Is greater than 95% for all three genotypes. Computational simulations show that both sensitivity and specificity improve as the number of reads per animal-locus increases. These computational results provide good evidence of the feasibility of the MGST approach at low read counts.

Using the Illumina sequencing platform to genotype multiple loci for multiple animals is feasible and economically practical. In addition, MGST can be easily applied to other sequencing platforms.

Reaction sizes have been scaled down successfully by 20 fold; (Ligation reactions reduced from 40 µl to just 2 µl). A simple one tube system has been successfully used where hybridization, ligation and the final sample indexing PCR all take place. In such a single tube system, 384 well plates have been utilized but we envision using 1536 well plates. At such sample densities we have explored the use of an acoustic based liquid handling device (Echo 555, from Labcyte, Sunnyvale, Calif.) which can move droplets of DNA and probe mixtures as low as 2.5 nL into such high sample plate geometries.

Using small reaction sizes in a single tube/sample format requires less than 10 ng of genomic DNA for the genotyping analysis of multiple of loci.

It will be understood that larger probe panels can include 137 different loci. It will also be understood that even larger probe panels can include 250, 500, 1000, 2000 and 5000 or more loci. It also will be understood that the disclosure can be performed using a robotics platform to handle the library preparations A dual sample ID barcode system can be performed where left and right index barcodes are added by a PCR reaction. This permits multiplying the number of sample ID barcodes (left×right) and obtain 10,000's of unique sample ID barcodes from a limited set of left and right PCR primers.

Sample probe panels can be designed for the detection (presence/absence) of microbial species in human and food samples.

Probe panels that permit gene methylation status to be determined have been designed.

Probe panels can be designed for the semi-quantitative analysis such as copy number variations as well as estimation of strain mixtures.

Figure 23:
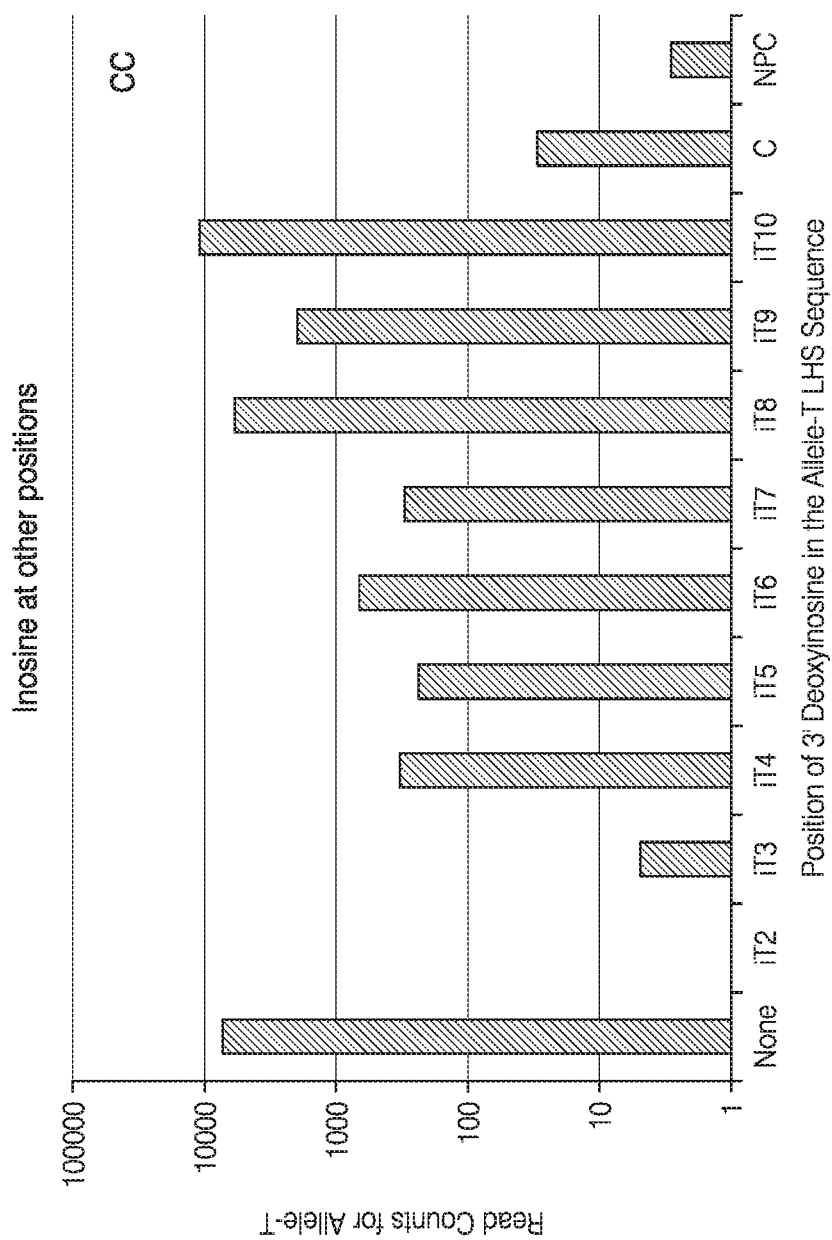
FIG. 23 depicts the effect of deoxyinosine at various positions
Figure 23:
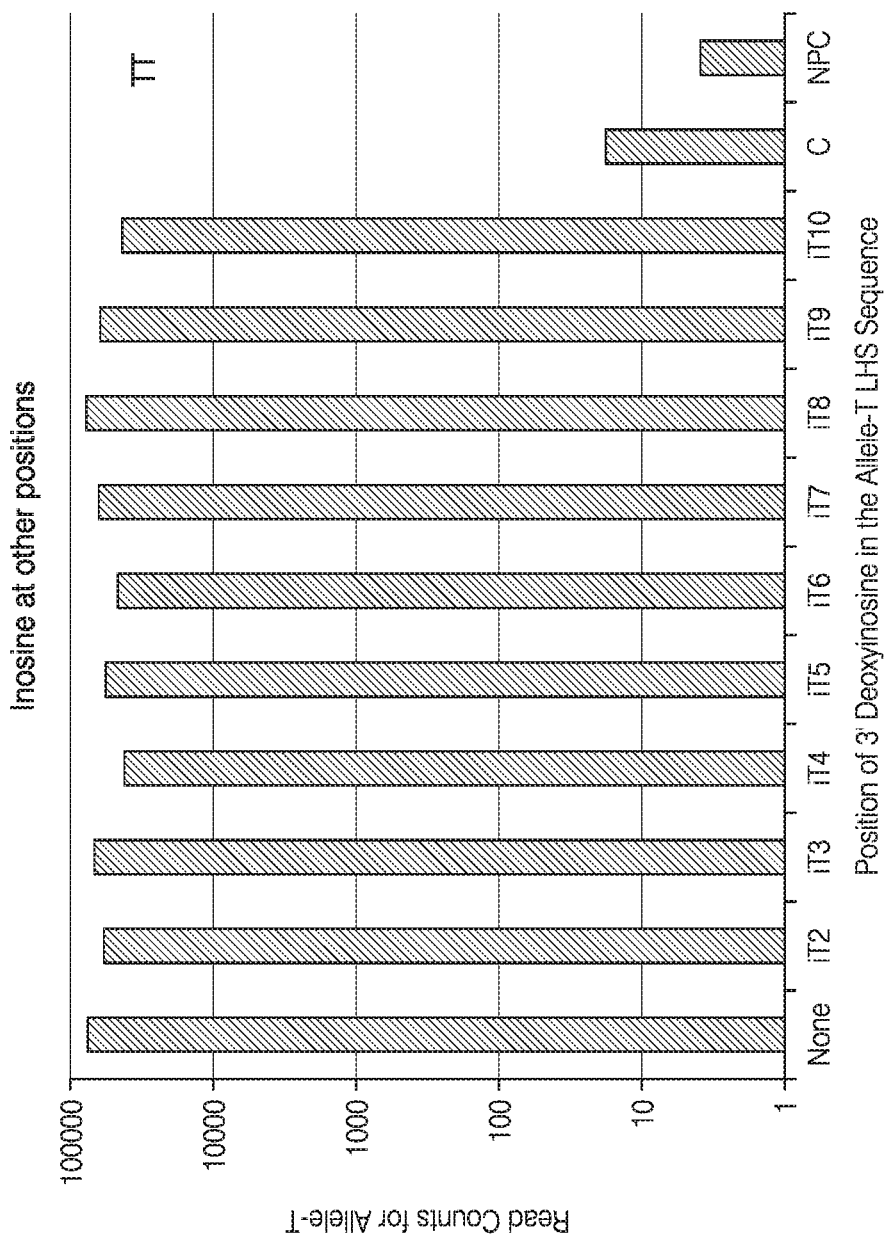
Figure 24:
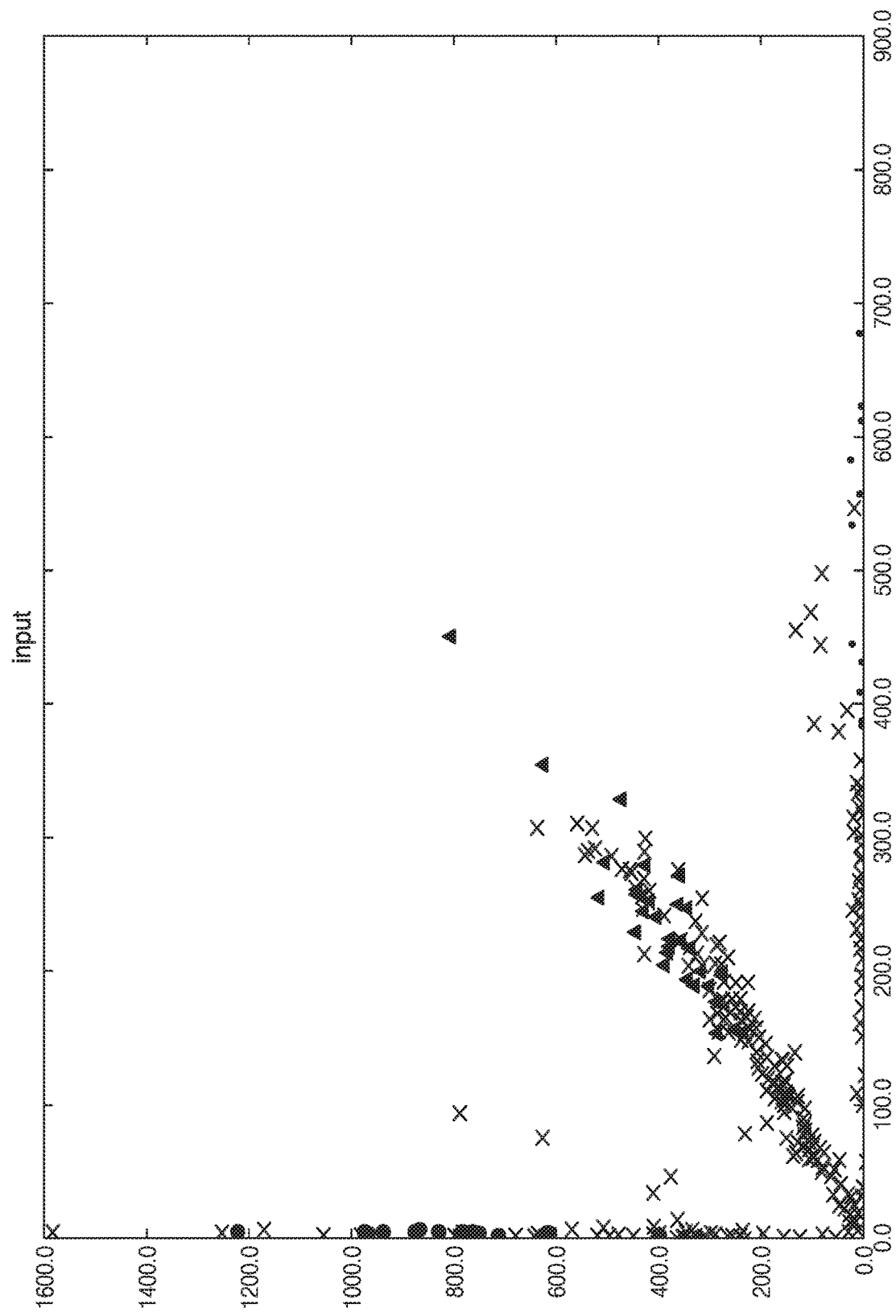
FIG. 24 shows the results from placing deoxyinosine at other positions in a first complementary sequence.
Figure 25:
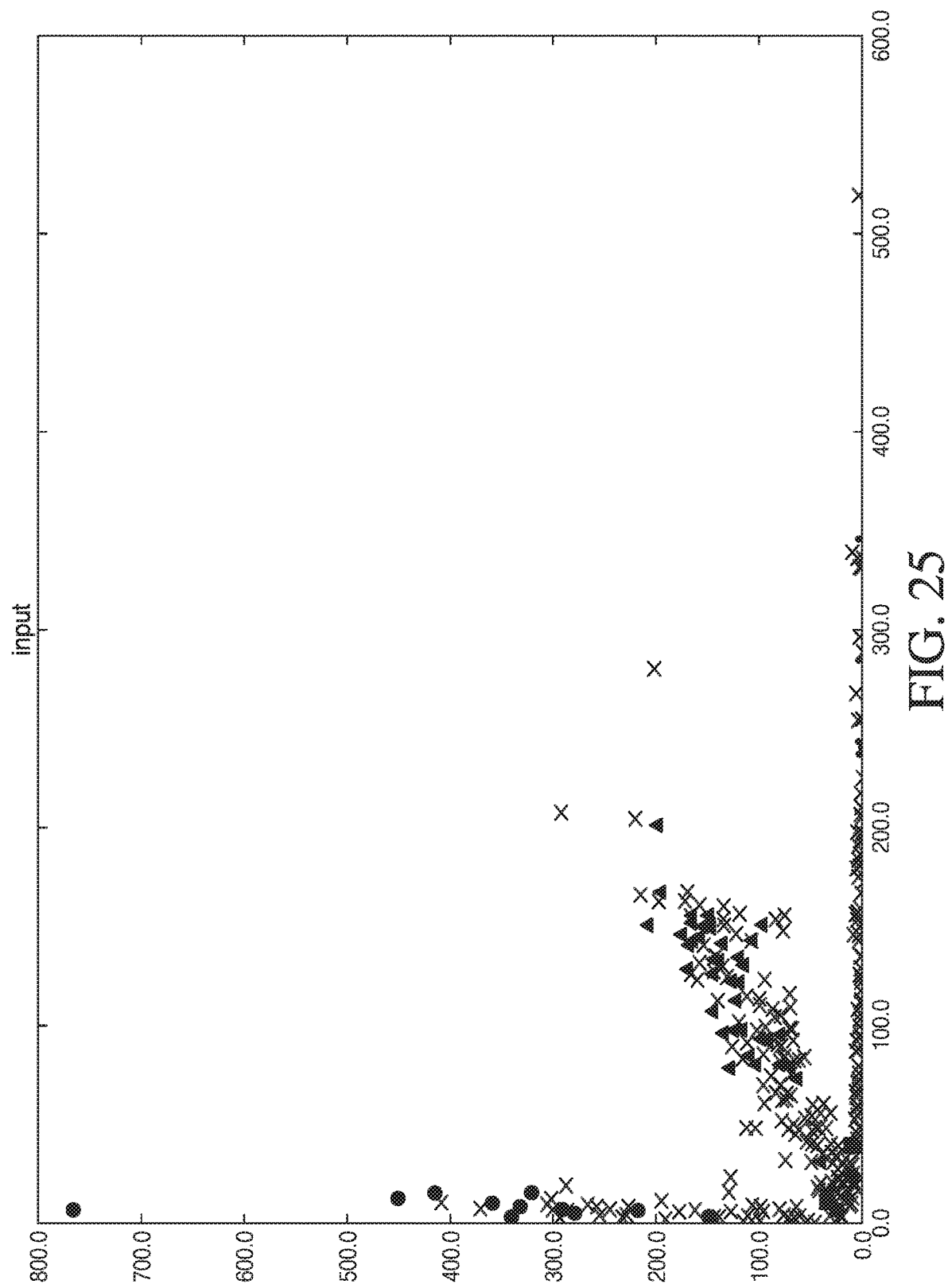
FIG. 25 shows the results from placing deoxyinosine at other positions in a second complementary sequence.

FIGS. 23, 24, and 25: Deoxyinosine

Taq DNA ligase poorly discriminates G or T mis-paired with T or G, respectively, due to partial hydrogen bonds that can occur between the mis-paired nucleotides. In general this mis-pairing with generate a 25% signal as compared to the properly paired G to C or T to A base pairing. This can confuse the genotyping assay.

The G:T mismatch effect can be alleviated by placing a non-pairing nucleotide such as the universal base deoxyinosine (dI) within the probe sequences (complementary polynucleotides) adjacent to the SNP interrogating nucleotide, a polymorphic nucleotide or nucleotide sequence in the complementary polynucleotide.

FIG. 23 is a CC animal with a first complementary polynucleotide comprising a 3' T (LHS-T). This figure demonstrates that the LHS-T probe produces a strong signal from the mis-pairing effect. However if a single deoxyinosine is placed at the 2nd (iT2) to 7th (iT7) 3' position of the LHS-T probe, the mismatch effect is removed. In this example, placement of the deoxyinosine at positions 8 (iT8) to 10 (iT10) have little effect and the mispairing produces a signal at nearly 25% of the properly paired sequences (FIG. 23, CC panel). The placement of the deoxyinosine in the LHS-T has no affect on the properly paired T:A match and its ligations by the Taq DNA ligase.

The CC panel of FIG. 23 shows the reads counts obtained from reactions programmed with genomic DNA from a homozygous CC animal at locus rs17870274 and probes that contained either no deoxyinosine (none) or deoxyinosine at the second (iT2) to tenth (iT10) 3' positions. A probe mix to examine the other allele-C is shown (C). A no probe control (NPC) is shown as well. The TT panel, at right, shows the reads counts obtained from reactions programmed with genomic DNA from a homozygous TT animal at the same locus rs17870274.

Continued examples of data obtained from LHS and RHS probes that have deoxyinosine at positions in the LHS and the RHS (FIGS. 24 and 25).

SNPs adjacent to the target SNPs have the potential to interfere with the hybridization of the first and second complementary polynucleotide and the target sequence, by altering the melting temperatures of the probes (the first and second complementary polynucleotides). To alleviate this issue we placed the universal base deoxyinosine at positions in the first complementary polynucleotide (LHS) and second complementary polynucleotide (RHS) that are affected by the adjacent SNPs. Deoxyinosine has no strong preference for complementarity and can be extended by Taq polymerase. FIGS. 24 and 25 show that placing the dI in the first complementary polynucleotide (LHS) or second complementary polynucleotide (RHS) does not affect the ability of the genotyping probes to operate and that the three expected genotypes (AA, AB, BB) are still presented as cluster spaces.

FIG. 24 shows the results from placing deoxyinosine at other positions in a first complementary polynucleotide. The first complementary polynucleotide, LHS402 [rs17871214] probes contain a single deoxyinosine at the ninth 3' position in order to alleviate the potential for a second single nucleotide polymorphism SNP 5' of that location (rs #17871215) to interfere with the binding the LHS probes. Closed circles represent the BB genotype, close triangles represent the AB genotype, closed little circles represent the AA genotypes, while the X marks are animals that had unknown genotypes.

FIG. 25 shows results of placing deoxyinosine at other positions in a second complementary sequence. The second complementary sequence, RHS480 [rs29021607] probe contain a single deoxyinosine at the fifth 5' position in order to alleviate the potential for a SNP 3' of that location (rs29021606) to interfere with the binding the second complementary sequence, RHS probe. Closed circles represent the BB genotype, close triangles represent the AB genotype, closed squares represent the AA genotypes, while the X marks are animals that had unknown genotypes. The LHS402 [rs17871214] probes contain a single deoxyinosine at the ninth 3' position in order to alleviate the potential for a SNP 5' of that location (rs #17871215) to interfere with the binding the LHS probes. Closed circles represent the BB genotype, close triangles represent the AB genotype, closed little circles represent the AA genotypes, while the X marks are animals that had unknown genotypes.

Example Seven

Figure 26:
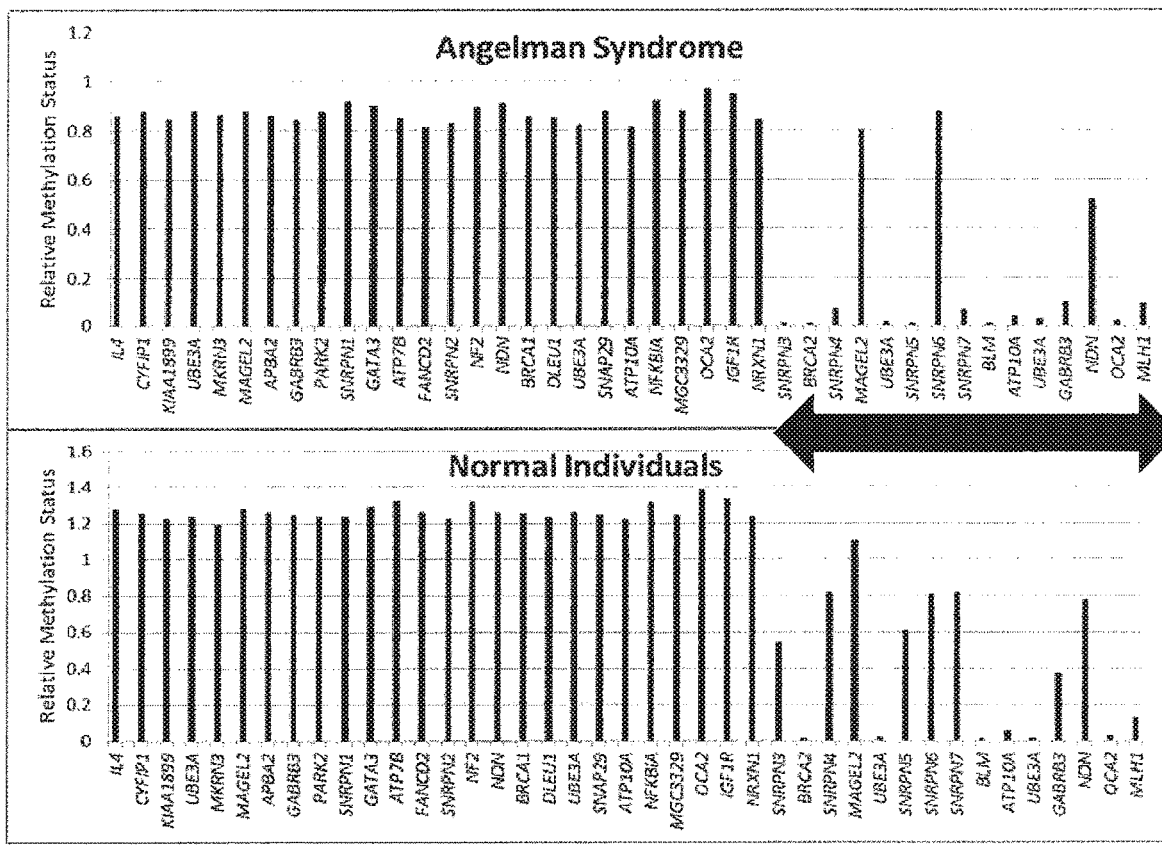
FIG. 26 shows results from the use of the presently disclosed method in the detection of methylation and copy number variation.

FIG. 26: Methylation and Copy Number Variation

FIG. 26 shows methylation and copy number variation status of the SNRPN gene in normal (n=3) and Angelman syndrome affected individuals (n=3). The mean relative methylation status is shown for the SNRPN gene. SNRPN was tiled with seven sets of complementary polynucleotides (1-7) of which SNRPN1 and SNRPN2 are not methylation sensitive sites and serve as controls, while the remaining five SNRPN3-7 are methylation sensitive. Only those sets of complementary polynucleotide for genes after (horizontal arrow) the NRXN1 gene are methylation sensitive. An approximately half fold reduction in methylation status for SNRPN3 indicates that only one maternal allele is methylated in the normal individuals, while both alleles are unmethylated in the AS individuals.

Methylation sensitive complementary polynucleotide sets in genes that are to be interrogated for methylation status are placed at HhaI sites within those genes. The HhaI site will only be cut by that methylation sensitive restriction enzyme if that site is not methylated. Sample genomic DNA to be tested is combined with the sets of complementary polynucleotide, hybridized, then ligated. The completed reactions are then split in half and one half treated with the HhaI enzyme and the other with mock enzyme mix. The split mixtures undergo PCR with different barcodes, and the library prepared for sequencing. For any particular gene the number of sequencing reads of the HhaI cut reaction are compared against the reads for the mock cut reaction. When the reads are equal, the gene is methylated, as the HhaI treatment does not destroy the ligated complementary polynucleotide. When the reads are disequal and the HhaI reads are reduced, this indicates that the HhaI sites were unmethylated and subjected to HhaI degradation. Angelman syndrome is a neurogenetic disorder resulting from aberrant expression of genes located in an Imprinting region on chromosome 15q11-q13. The SNRPN gene is located in that area and seven sets of complementary polynucleotides in that gene can monitor the imprinting (methylation), two of the seven are unaffected by methylation and serve as controls. FIG. 26 shows that the imprinting is lost in the SNRPN gene in AS affected individuals as compared to normal individuals. Genomic DNA was obtained from established lymphoblastoid cell lines, which maintain the original imprinting of the donor. The SNRPN3 and SNRPN5 complementary polynucleotide positions shows an approximately ½ fold reduction in copy number, as only the maternal copy of the imprinting region is methylated.

Example Eight

Figure 27:
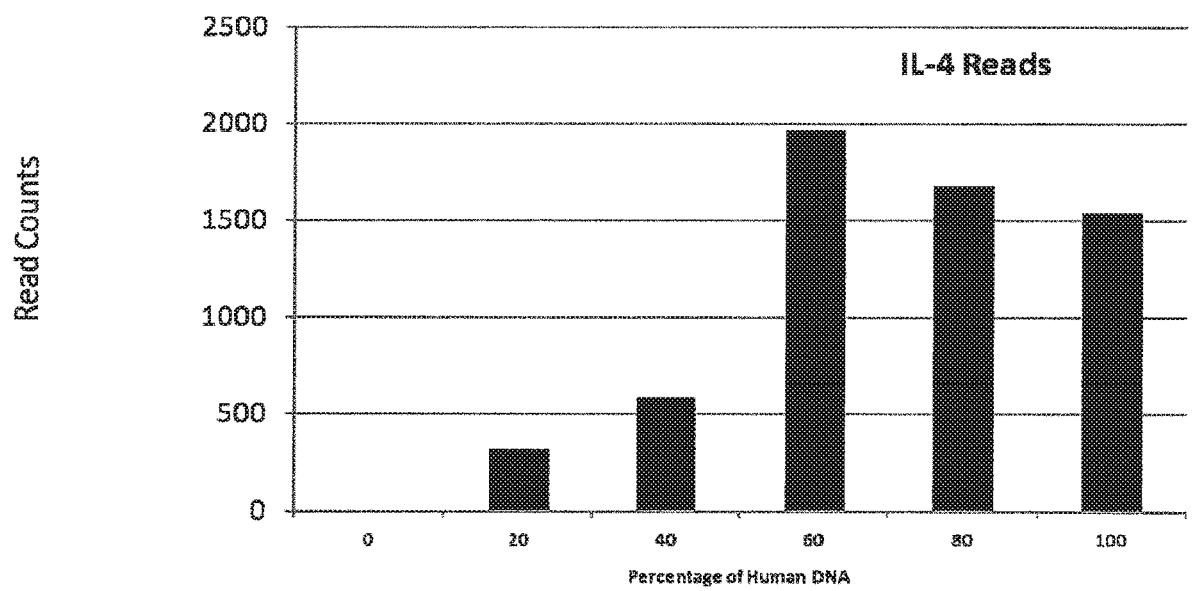
FIG. 27 shows the use of the presently disclosed method in the Quantification in a heterogeneous sample.

FIG. 27: Quantification of Heterogeneous Samples.

Human genomic sample DNA was mixed with *Bos taurus* genomic sample DNA at 6 increasing amounts. The mixtures were then mixed with a human first and second complementary polynucleotide sequence probe panel containing 41 different target gene detection probes (first and second complementary polynucleotide sequences), after hybridization, ligation, and barcoding PCR (addition of tag sequences), the library was sequenced. The read results for a single probe set (IL-4) are shown. In this example, between 0% and 100% the relationship between the % human DNA and the number of reads is roughly 15 reads per 1% of human DNA.

Example Nine

Figure 28:
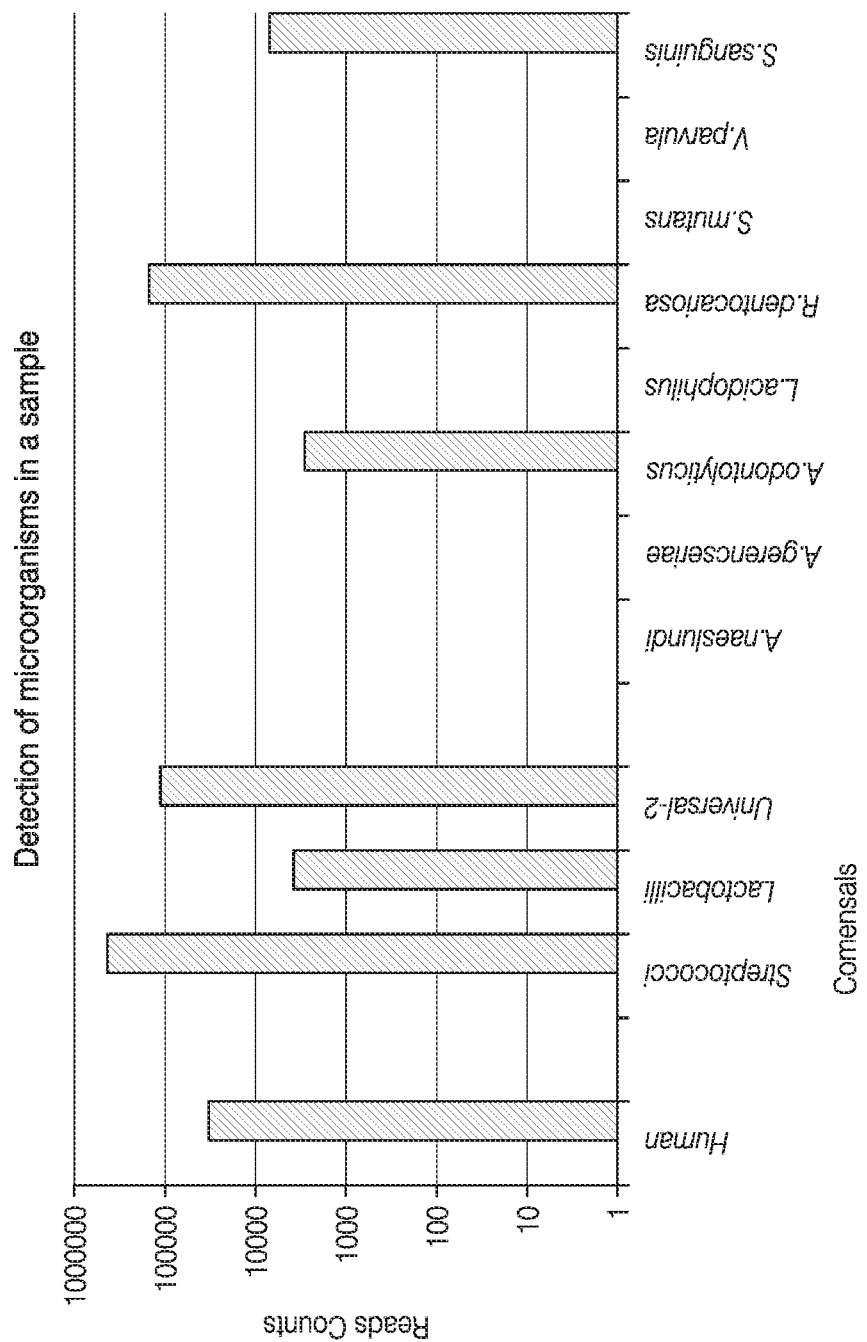
FIG. 28 shows the use of the presently disclosed method in detection of a microorganism in a sample.

FIG. 28: Detection of a Microorganism in a Sample.

Target DNA sequence of several cariogenic bacteria species were detected in a sample DNA preparation extracted from human saliva. A single human specific first and second complementary probe set was used to detected the human DNA target sequence expected in the saliva DNA sample, as well as first and second complementary polynucleotide probe sets for two commensal bacteria species (Streptococci, Lactobacilli), as well as a Universal-2 marker for bacterial DNAs'. A panel of seven first and second complementary polynucleotide probe sets for cariogenic bacteria probes sets, identified three species DNA in the subjects' saliva sample. In this example the probe sets have a single left hybridization sequence and a single right hybridization sequence.

Example Ten

Figure 29:
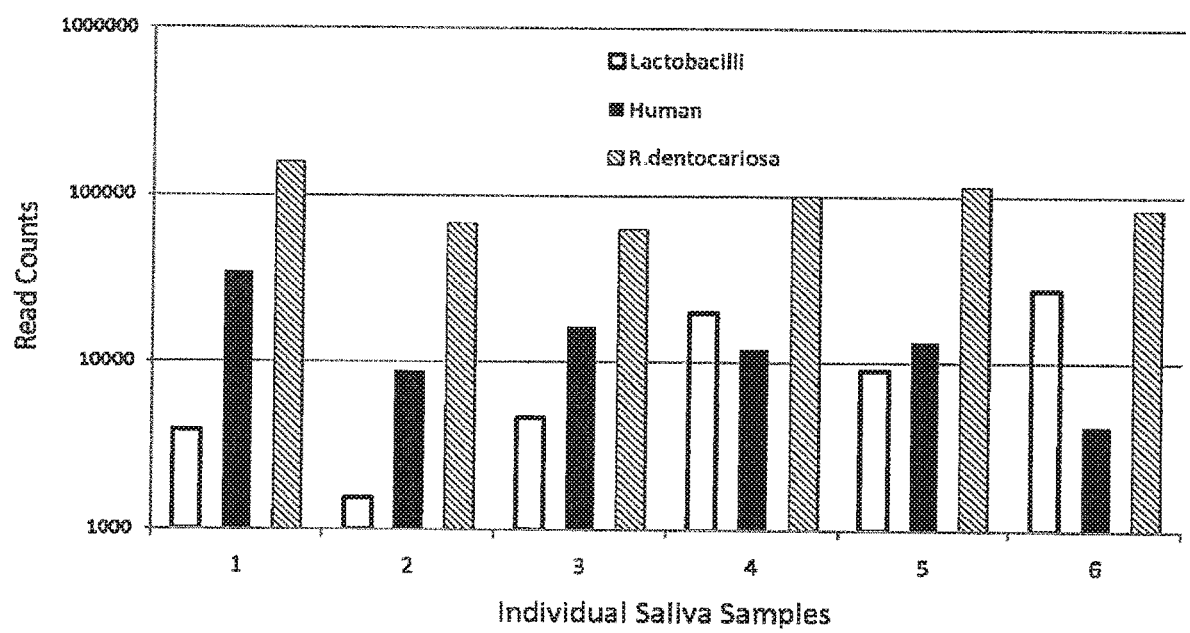
FIG. 29 shows the use of the presently disclosed method in quantification of different organisms in a sample

FIG. 29: Quantification of MO (Microorganisms) in a Sample.

Quantification of human genomic DNA and bacterial DNA in a sample of DNA extracted from human saliva. A single cariogenic bacterial species was quantified between six different individuals' saliva DNA samples. Complementary polynucleotide probe sets to human, common commensal bacteria, and a cariogenic bacterium were used to quantify differing levels of their presence in DNA samples obtained from the saliva of healthy human donors. Saliva contains a mixture of sluffed human epithelial cells as well as a plethora of commensal bacteria that populated the human oral cavity. Tooth decay causing bacteria can be detected within this complex mix and quantified. After normalizing to the number of reads produced with the complementary nucleotide sets directed to the human sample, the relative (or absolute) amounts of the organism detected with the other probes can be determined (based on the number of reads). Such an exercise can be facilitated with standard curves.

Example Eleven

Figure 30:
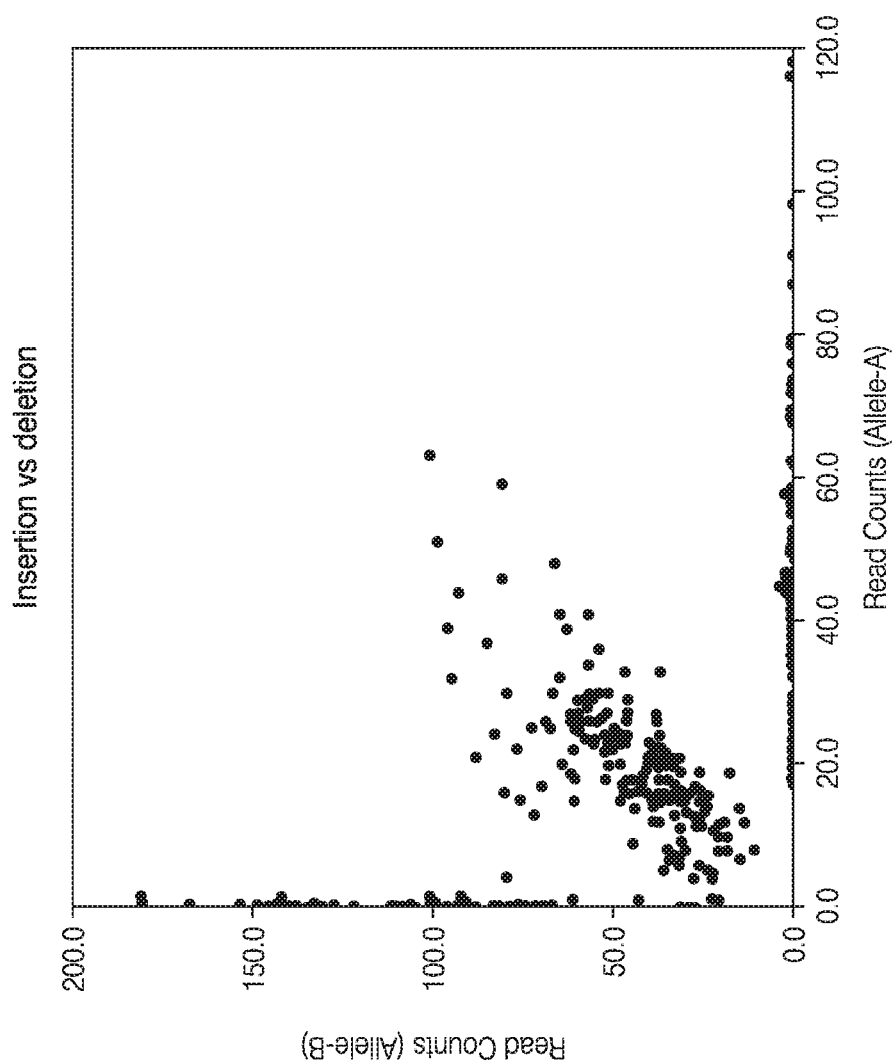
FIG. 30 shows the use of the presently disclosed method in detection of a small dinucleotide repeat variant (INDEL) and of a single nucleotide deletion.
Figure 30:
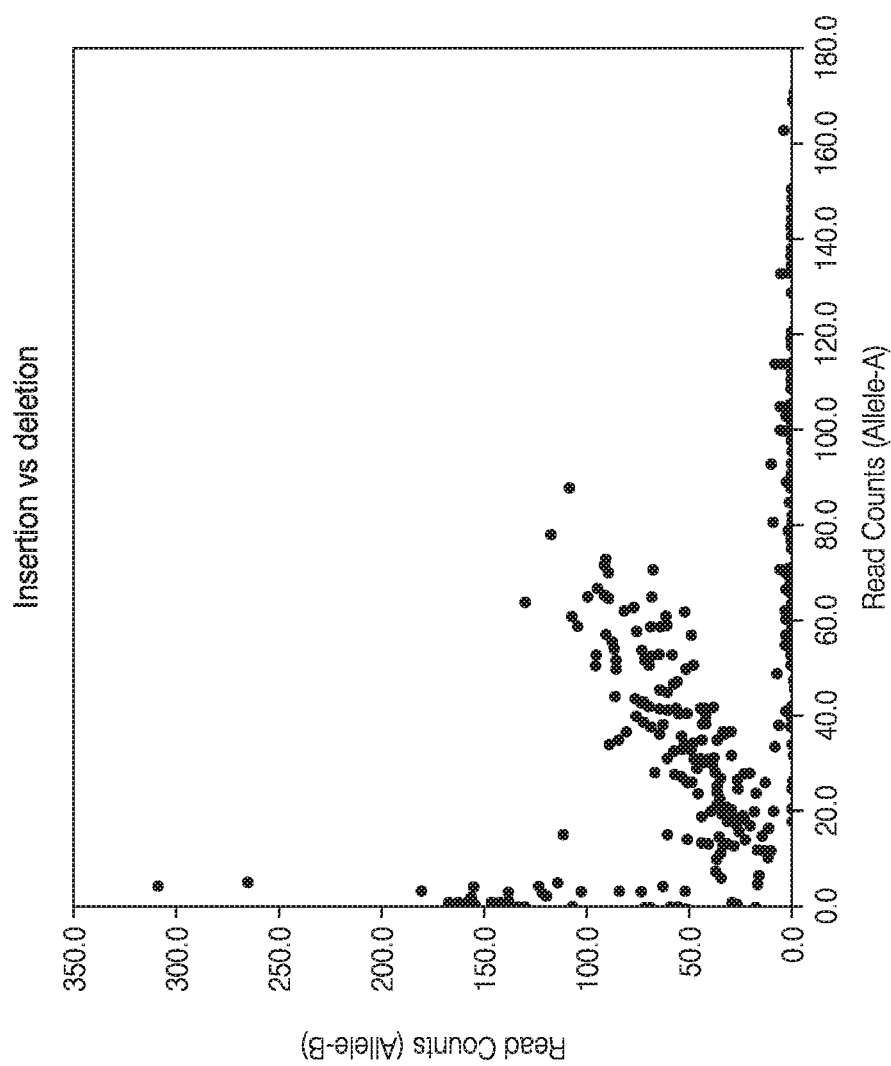

FIG. 30: Detection of a Small Dinucleotide Repeat Variant (INDEL) and of a Single Nucleotide Deletion.

The presently disclosed method, MGST, can detect other sequence changes such as the insertions and deletions.

The second complementary polynucleotide (RHS) is placed at the right most common sequence between the wild-type first target sequence and the polymorphic or variant sequence. The first complementary polynucleotide (LHS-wild-type probe) is placed such that its 3' sequences reflect the wild-type target sequences immediately 5' of the common second complementary polynucleotide (RHS) sequences. The variant second complementary polynucleotide (LHS) reflects the variant target sequence that is immediately 5' of the common second complementary polynucleotide (RHS) sequences. This LHS-wt/LHS-var/RHS probe (complementary polynucleotide) set can then detected homozygous or heterozygous individuals for that particular sequence alteration or wild type condition. Right Panel. A small CT dinucleotide insertion is detected (A>ACT). Left Panel. A single nucleotide deletion is detected (CAAAAAA>CAAAAA). Points along the Y axis are homozygous variants while those along the X axis are homozygous wild-type. Intermediate points are heterozygous and have a single copy of both the variant and the wildtype alleles.

Example Twelve

Figure 31:
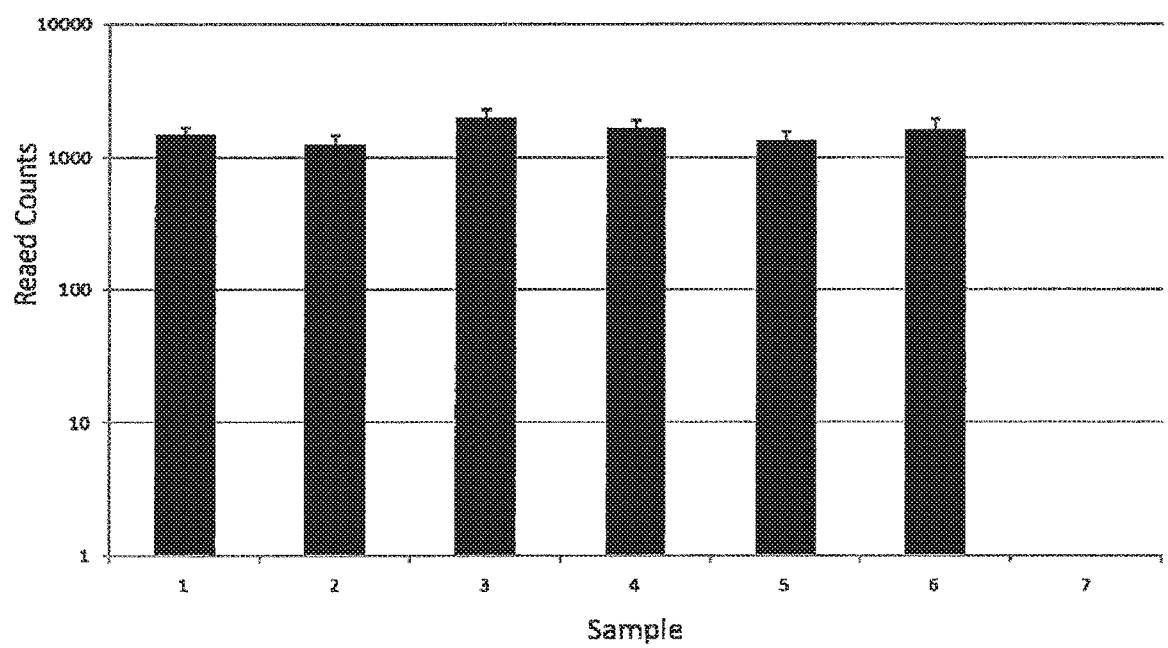
FIG. 31 shows the use of the presently disclosed method for the detection of insertion and deletion polymorphisms.

FIG. 31 Single Allele SNP, the Presence or Absence of a Single Target Polynucleotide The presently disclosed method, MGST, can be used to detect specific target sequences, essentially a presence or absence test. In this case a set of two complementary polynucleotides (i.e. one first complementary polynucleotide and one second complementary polynucleotide, a probe doublet) instead of a set of three complementary polynucleotides (i.e. two first complementary polynucleotide and one second complementary polynucleotide, a probe triplet) is used. FIG. 31 shows results for a detection of a specific high GC rich target sequence within chromosome 19 of the bovine genomic DNA sample. Six of the seven samples have the sequence and 1 of the seven samples does not.

Example Thirteen

Figure 32:
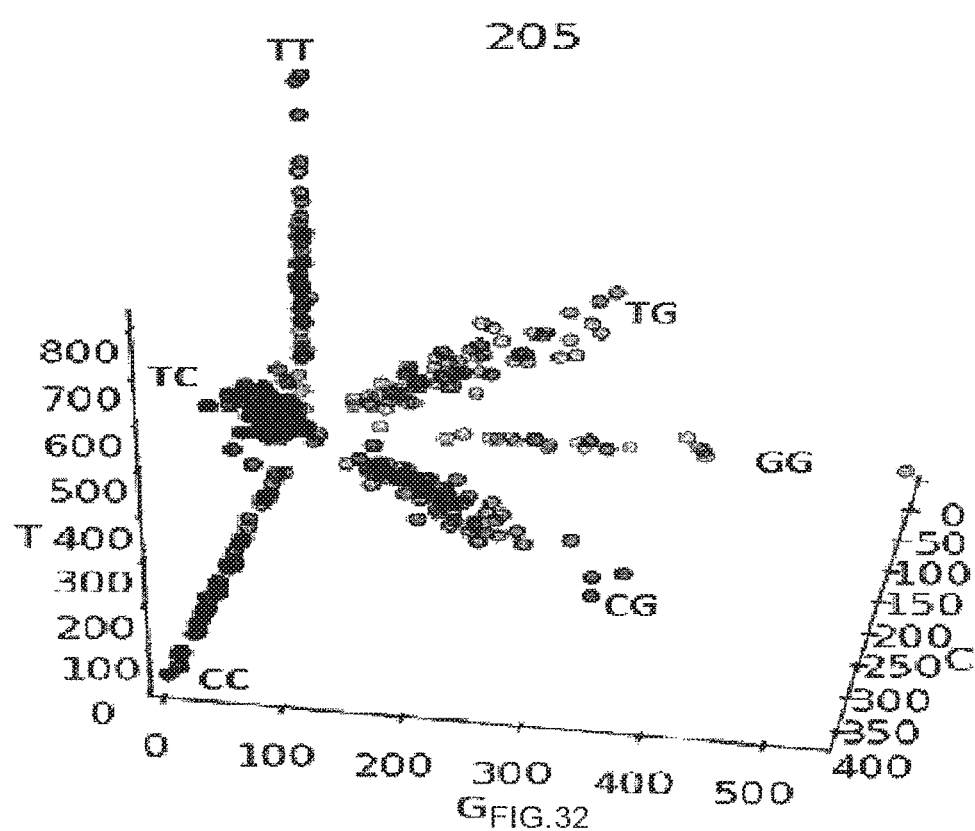
FIG. 32 shows the use of the presently disclosed method in detection of three-allele single nucleotide polymorphisms.

FIG. 32: Three Allele SNP Detection

The presently disclosed method, MGST, is able to genotype poly-allelic SNPs' by the simple addition of complementary polynucleotide sets comprising three or more first complementary polynucleotides (LHS; which differ in their 3' nucleotide(s)) specific for the additional allele/s in the target sequence. In the example shown in FIG. 32, there were three nearly identical first complementary polynucleotides (LHS), each first complementary polynucleotide with a different 3' terminal nucleotide complementary to a polymorphism (for example a SNP) in the genomic target sequence sample DNA. The allele-specific tag (allele barcode) was also altered to match the three possible SNPs. No other changes to the protocol were required, other than to bin the third allele type from the sequence data.

Example Fourteen

Figure 33:
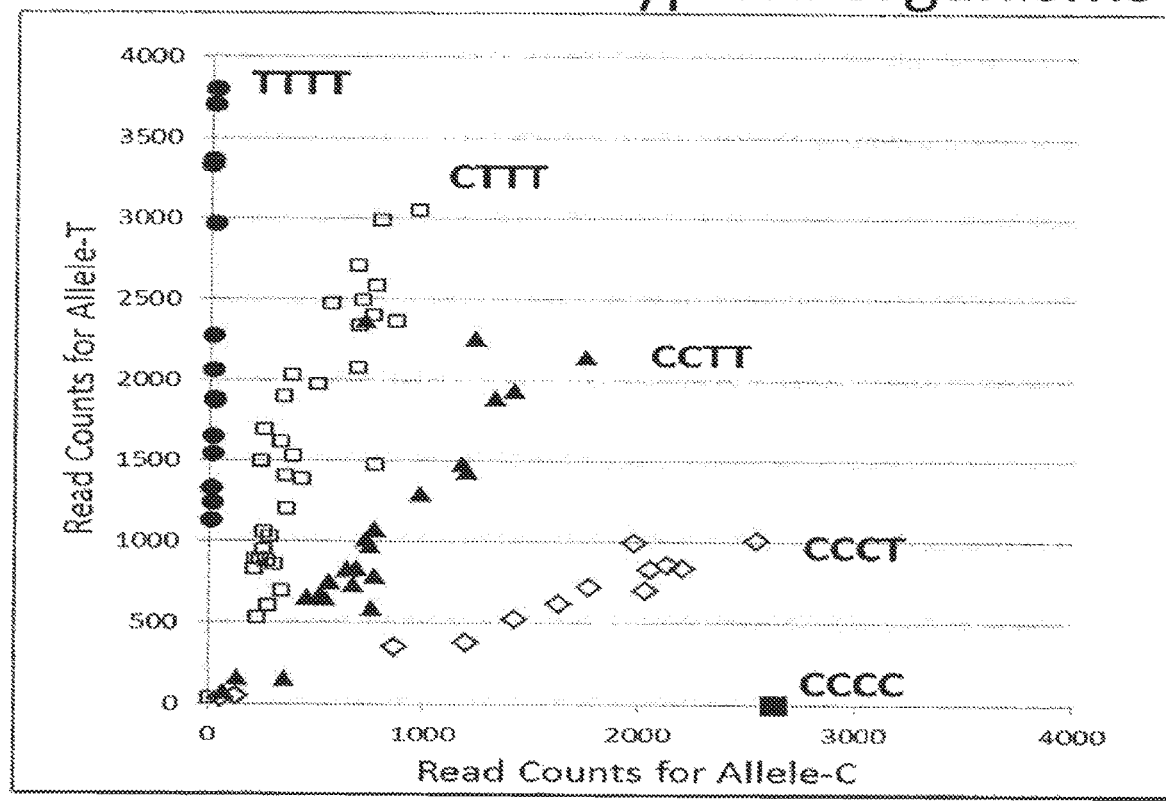
FIG. 33 shows the use of the presently disclosed method in detecting the genotype of a mock tetraploid genomic DNA sample.

FIG. 33: Genotype of a Mock Tetraploid Genomic DNA Sample

The presently described method, MGST, can genotype tetraploid organisms. For example, in tetraploidy, four copies of an allele can exist, one on each of four chromosomes. To mimic a tetraploid organism, two different bovine DNA samples were mixed together. This produced a sample with four copies of any given allele. A probe panel (mixture of multiple sets of first and second complementary polynucleotides) that queries 113 loci was used. Loci DQ404153, which comprises a polymorphic C/T site, was examined by the presently described method, MGST.

FIG. 33 plots reads for the Allele-C against reads for the Allele-T. Mock tetraploid DNA representing TTTT (solid circle) or CCCC (solid square) genotypes plot along the Y or X axis, respectively. Mock tetraploid DNA representing heterozygous genotypes are shown as open squares (CTTT), closed triangle (CCTT), and open diamonds (CCCT).

The sequence results demonstrate that the presently disclosed method is capable of identifying the expected five different genotypes (CCCC, CCCT, CCTT, CTTT, and TTTT) possible in a tetraploid organism.

Example Fifteen

Figure 34:
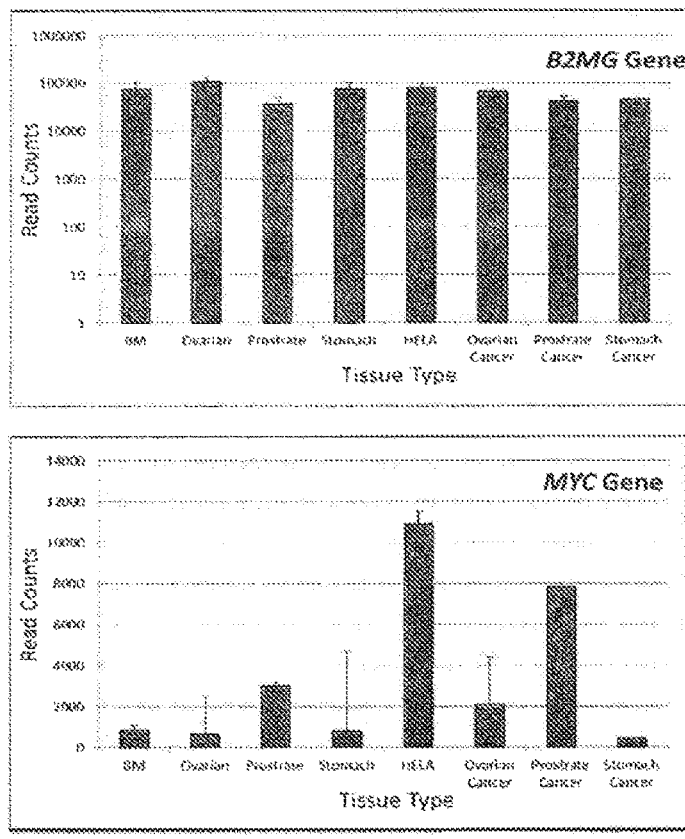
FIG. 34 shows the use of the presently disclosed method in detection of RNA as the starting sample.

FIG. 34: Detection with RNA as the Start

The presently disclosed method, MDST, can be used with RNA as the starting sample and can be used for RNA expression analysis. Human RNA samples were obtained from a variety of healthy and diseased tissues. The RNA was mixed with a panel of 41 primer sequences which permitted those sequences to be copied into cDNA form. The cDNA mixture was then hybridized to the sets of first and second complementary polynucleotide, i.e. LHS and RHS probes, mixtures, ligated, indexed by PCR and then the library sequenced. The top panel of FIG. 34 shows the results for a common housekeeping gene (beta-2-microglobulin) used for signal normalization. The number of reads produced with the oncogene (c-myc) which is known to be highly expressed in HELA and some cancers are elevated in the HELA sample and in the prostate cancer sample compared to the other samples (including prostate non-cancer).

Example Sixteen

Figure 35:
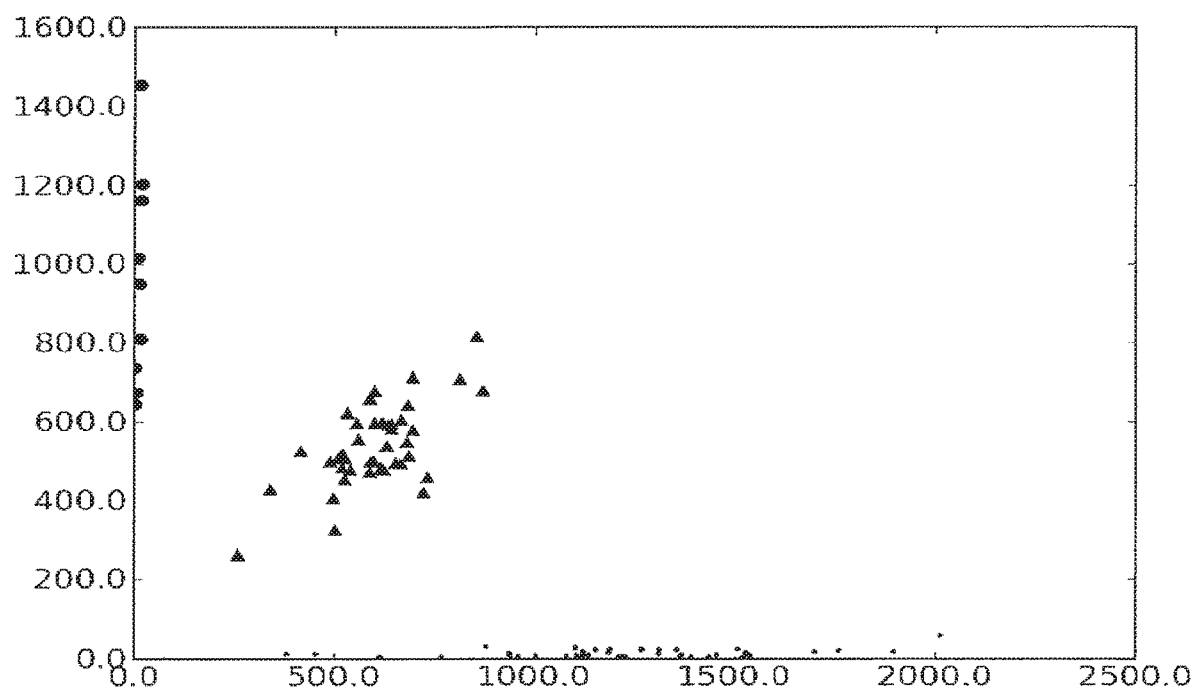
FIG. 35 shows the use of the presently disclosed method wherein samples are resolved on a MiSeq instrument from Illumina, Inc.

FIG. 35: MGST as Resolved on a Illumina MySeq Instrument

MGST libraries can be resolved on other Illumina sequencing devices such as the MySeq device. The genotype for the bovine locus rs29001956) resolved by MGST on a MySeq next generation sequencing platform. The allele-A reads (x-axis) are plotted against the allele-B reads (y-axis) for 96 bovine samples. The animals with homozygous BB genotypes cluster along the Y-axis (close circles) while those with homozygous AA genotypes cluster along the X-axis (small point), with those heterozygous animals cluster between the axis (closed triangles).

Example Seventeen

Figure 36:
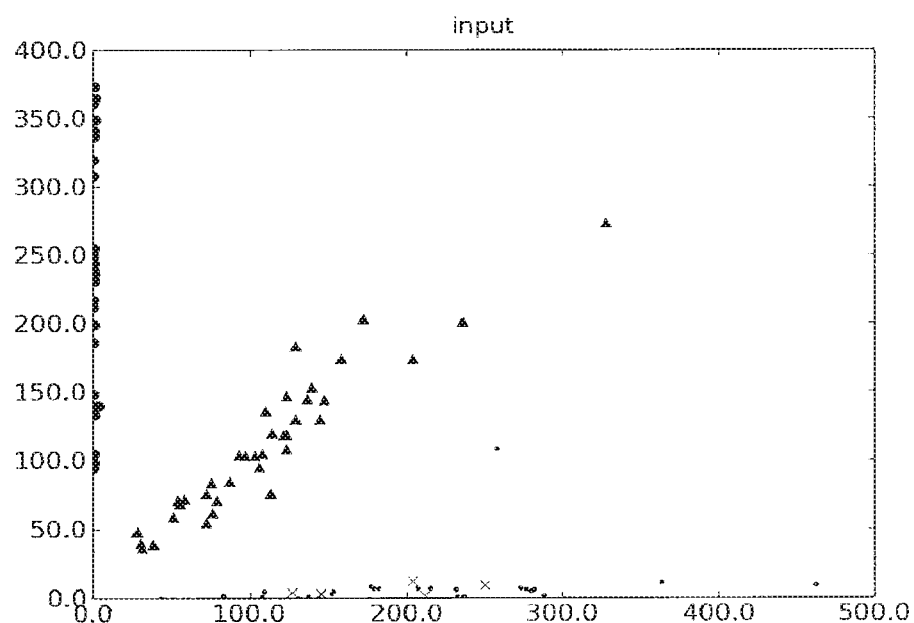
FIG. 36 shows the use of the presently disclosed method wherein samples are resolved on aIon Torrent machine from Life Technologies, Inc.

FIG. 36: Ion Torrent Detection

The basic assay can be modified to work on sequence data generation instruments other than Illumina.

The presently described method, MGST, as resolved on a Life Ion Torrent instrument (PGM). This requires that the sequences required for sequence data generation on the on Torrent be added to the joined product. As described in FIG. 36, the form of the sequence data generation is specific. This similar form may or may not be used with other sequence data generation platforms. A bovine SNP (rs29009668) resolved by MGST on an IonTorrent next generation sequencing platform. The allele-A reads (x-axis) are plotted against the allele-B reads (y-axis) for 96 bovine samples. The animals with homozygous BB genotypes cluster along the Y-axis (close circles) while those with homozygous AA genotypes cluster along the X-axis (small point), with those heterozygous animals cluster between the axis (closed triangles). Animals with unknown genotypes are shown (X).

Example Seventeen

Figure 37:
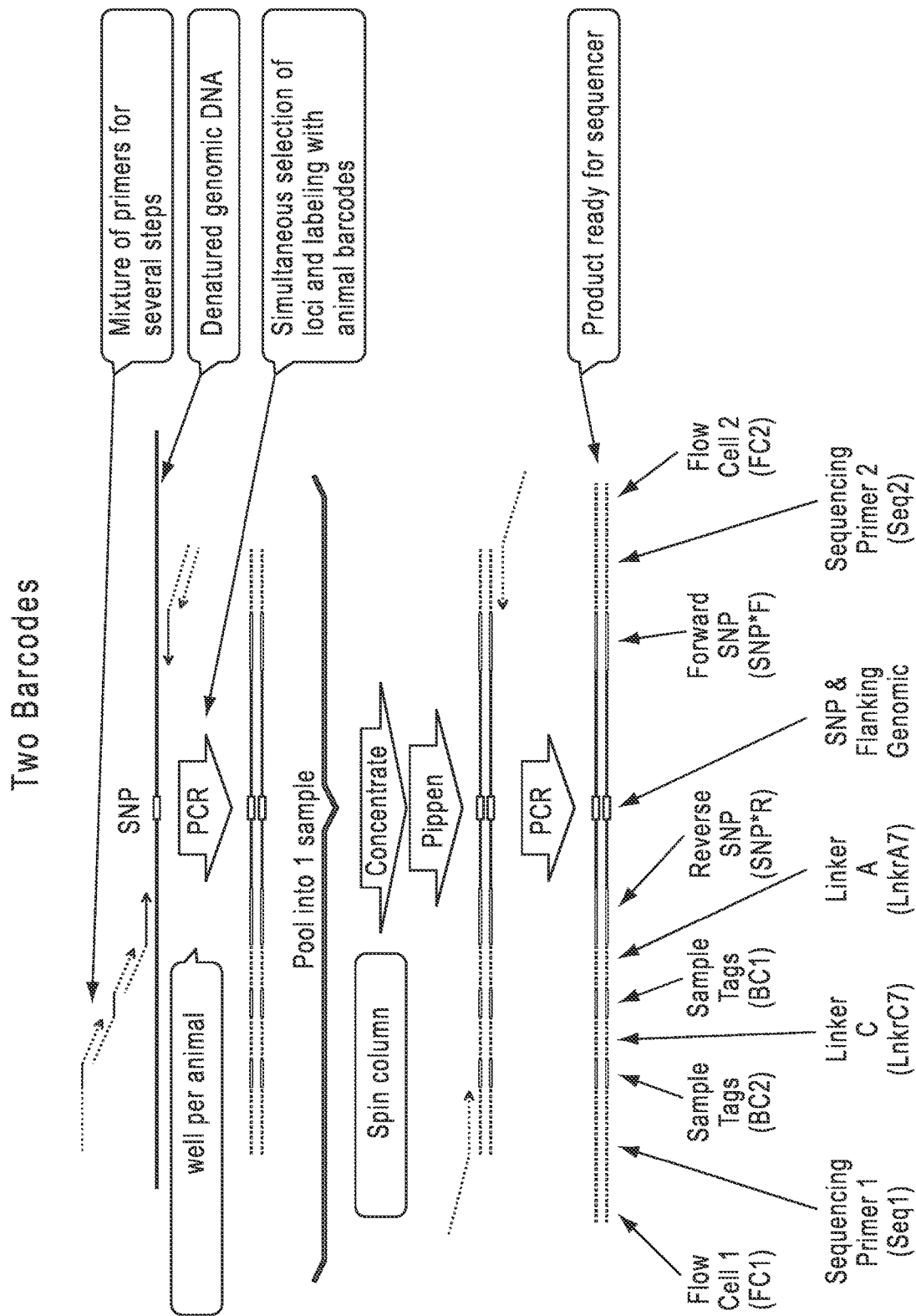
FIG. 37 is a diagram showing the joining occurring by polymerase.

FIG. 37: Diagram of Illumina Sequencing of Product Polynucleotides Produced by PCR Genomic bovine DNA was obtained from either whole blood, buffy coat samples, or bull semen. The sample DNA was extracted using either a salt extraction method (whole blood), commercial DNA isolation kit (whole blood/buffy coats) or proteinaseK/organic solvent treatment (semen).

Illumina genotyping has previously been used to genotype these specific individuals, using the Illumina BovineSNP50 BeadChip.

Oligonucleotide primer pairs were designed to amplify 98 target sequences that included polymorphic nucleotides (for example, SNPs). The target sequences were between 47 and 97 bps of genomic DNA sequence. PCR primers were designed such that the 3' base of the reverse primer was no further than 14 bases from the polymorphic nucleotide(s) (for example an SNP). Each primer pair comprised a reverse primer and a forward primer. Each reverse PCR primer also contained the 3' 33 bp of the reverse Illumina sequencing primer sequence (Seq2; 5'-CTCGGCATTCCTGCT-GAACCGCTCTTCCGATCT-3') at the 5' end of the primer. The 33 bp Illumina sequencing primer sequence will serve as the amplification initiation site for the entire Illumina Sequencing primer sequence added in by PCR in a future step. The forward SNP primer had a 20 bp linker sequence, either called A4 (5'-GGTGGGTTGGTGGAGTTGAG-3') or A7 (5'-ACACGACGGTCTTCCGACTC-3') appended to its 5' end.

Samples included a tag sequence (barcode). The tag sequences were added with two additional oligonucleotide primers, termed bar-coding primers. The first set of barcoding primers (Barcode1) contained from 5' to 3': 20 bp sequence for linker C7 (5'-TCCGCCTCTCC-CACGCCGTC-3'), 8 bp of barcoded tag sequence, followed by the sequence for either linker A4 or A7. The second set of 24 bar-coding primers (Barcode2) consisted of the following sequences 5' to 3': 33 bp of Illumina sequencing primer sequence (Seq1; 5'-ACACTCTTTCCCTA-CACGACGCTCTTCCGATCT-3'), 8 bp of barcoded tag sequence and the linker C7 sequence.

The 192 oligonucleotide primer sets for 96 of the 98 loci were combined to a final concentration of 100 uM. PCR was performed with 5-10 ng genomic DNA samples that were dried in wells of 384-well plates (1 DNA sample per well). PCR reactions were performed using the following methods: 0.625 ul 10× Buffer, 0.325 ul 25 mM MgCl2, 0.4 ul 25 mM dNTP mix (dATP, dCTP, dGTP, dTTP), 0.25 ul HotStar Taq, 4 uM forward and reverse SNP primer mix, 4 uM C7-Barcode1-A7 primer, 4 uM Seq1-Barcode2-C7 primer 5'-ACACTCTTTCCCTACACGACGCTCTTCCGATCT-barcode-TCCGCCTCTCCCACGCCGTC-3', 4 uM Illumina Seq2 primer 5'-CTCGGCATTCCTGCT-GAACCGCTCTTCCGATCT-3', adjusted to a 5 uL volume with water. Thermal Cycler conditions were as follows: 95° C. for 15 min; 3 cycles of 94° C. for 30 s, 56° C. for 1 min, 72° C. for 1 min; 5 (or 12) cycles of 94° C. for 30 s, 58° C. for 1 min, 72° C. for 1 min; followed by a final extension of 72° C. for 3 min and holding temperature of 50° C.

Sample-specific tagged and completed PCR reactions were combined into a single volume. A portion of the combined volume was electrophoresed on a Pippen System to select PCR products of appropriate size to use for the sequencing library. PCR products were between 157 base pairs to 226 base pairs. To create a sequencing library, the pooled sample was diluted 1:100 with water and 1 uL of this was amplified with the full length Illumina sequencing primers (5'-AATGATACGGCGACCACCGAGATCTA-CACTCTTTCCCTACACGACGCTCTTCCGATCT-3') and (5'-CAAGCAGAAGACGGCAT-ACGAGATCGGTCTCGGCATTCCTGCT-GAACCGCTCTTCCGA TCT-3') set using the following reaction conditions: 6.25 uL of 4 uM full length forward Sequencing primer, 6.25 uL of 4 uM reverse sequencing primer, 5 uL 10×Buffer, 1 uL 10 mM each dNTP, 2 uL HotStar Taq, and adjusted to a final volume of 50 uL with water. Thermal cycling conditions were: one cycle at 95° for 15 min, 12 cycles of 95° C. for 20 s, 65° C. for 30 s, and 72° C. for 30 s, followed by one cycle of 72° C. for 5 min and final temperature of 4° C.

A portion of the library volume was then cleaned up with a PCR clean up column (Qiagen) and eluted into 20 ul TE. A portion of the eluate was examined on an eGene System to determine the concentration of the library and to ensure that PCR primers and primer dimers had been removed.

In some instances (i.e. experiments with small numbers of samples), dual barcoding may not be required and a single barcode method may be employed. Oligonucleotide primers for single barcode experiments were designed in the following manner from 5' to 3': 33 bp of Illumina sequencing primer sequence Seq1 (5'-ACACTCTTTCCCTA-CACGACGCTCTTCCGATCT-3'), 8 bp of barcoded tag sequence, followed by the sequence for either linker A4 or A7. PCR was performed as described above with the exception of the substitution of the barcoding primers.

Sequence data was generated. The sequence reads can be placed in bins based on the sample barcode(s). Analysis of the SNPs contained in the sequence data in the bins allows the number of reads associated with the target polynucleotide(s) to be determined.

The general approach is diagramed in FIG. 37.

Example Eighteen

Figure 38:
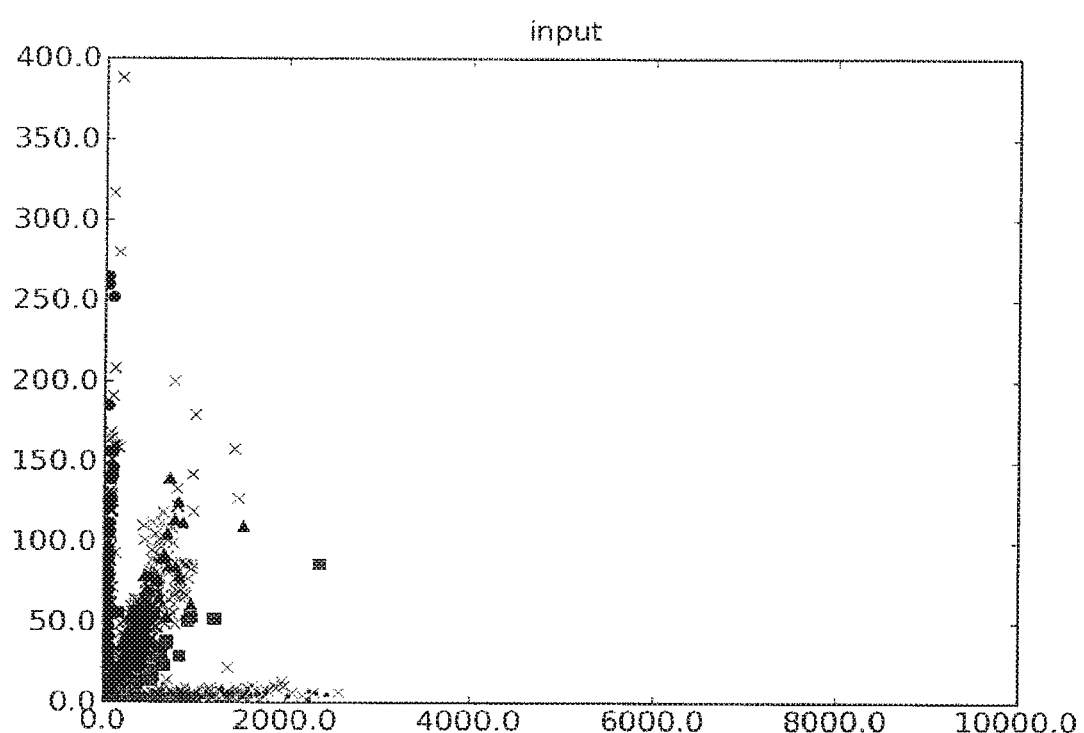
FIG. 38 shows an example of a cluster plot where the number of reads for Allele-A are highly skewed from the number of reads obtained for Allele-B. The various symbols indicate the genotype inferred (within a user defined statistical confidence) and whether it is concordant with the genotype determined by an alternative method. In some cases the probability of the genotype is known, but the genotype is not inferred as it does not fall within the user defined statistical criteria. Y-axis is the number of reads for allele-B and X-axis is the number of reads for allele-A.
Figure 39:
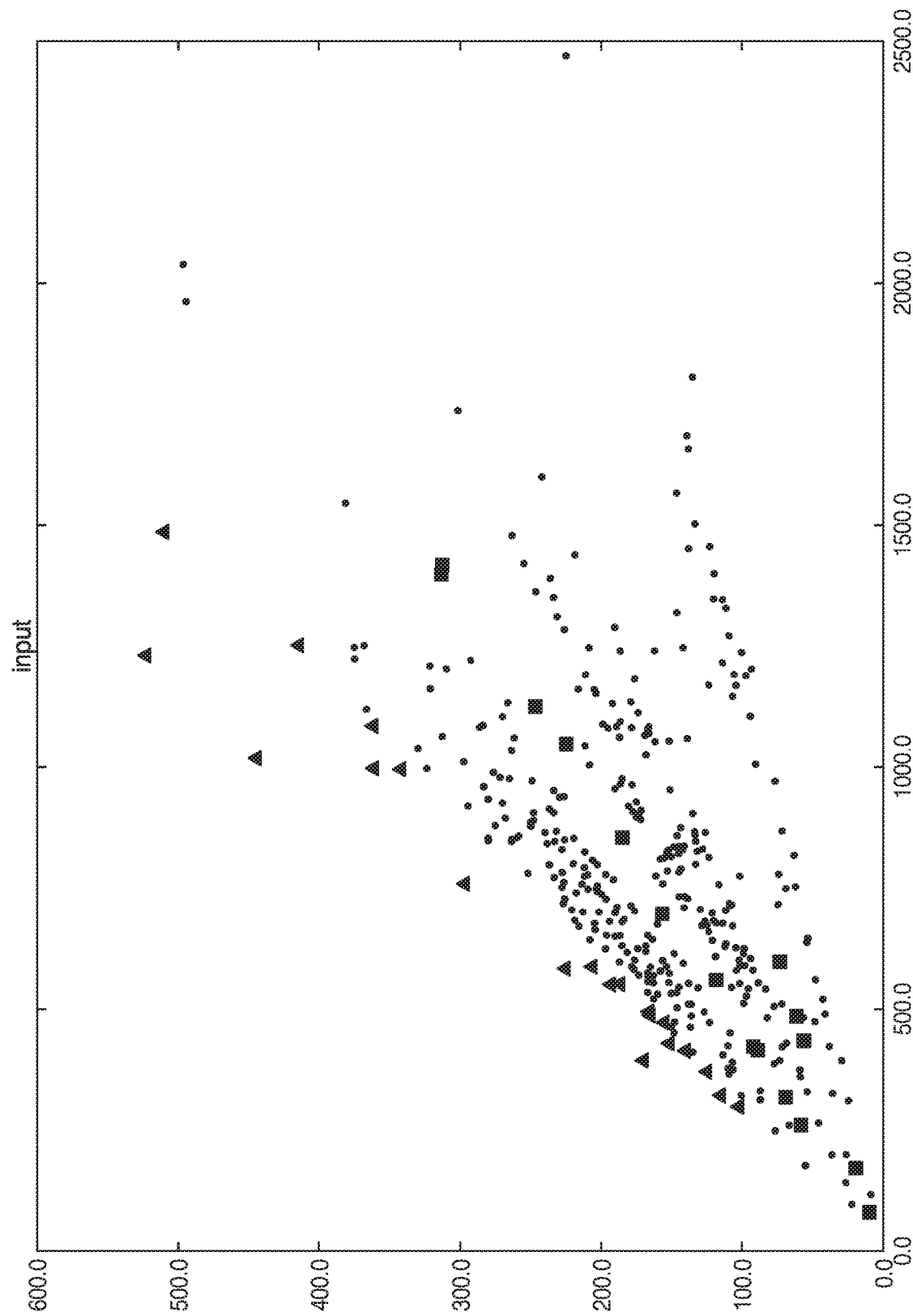
FIG. 39 shows another example of a cluster plots where the number of reads for Allele-A are highly skewed from the number of reads obtained for Allele-B.

FIGS. 38 and 39: Illumina Sequencing of Product Polynucleotides Produced by PCR

The presently disclosed method, MGST (LDMA), can produce cluster plots where the reads for the two different alleles are highly skewed (one in several fold excess of the other). Even in this situation the presence or absence of the target polynucleotide can be determined.

Example Nineteen

Figure 40:
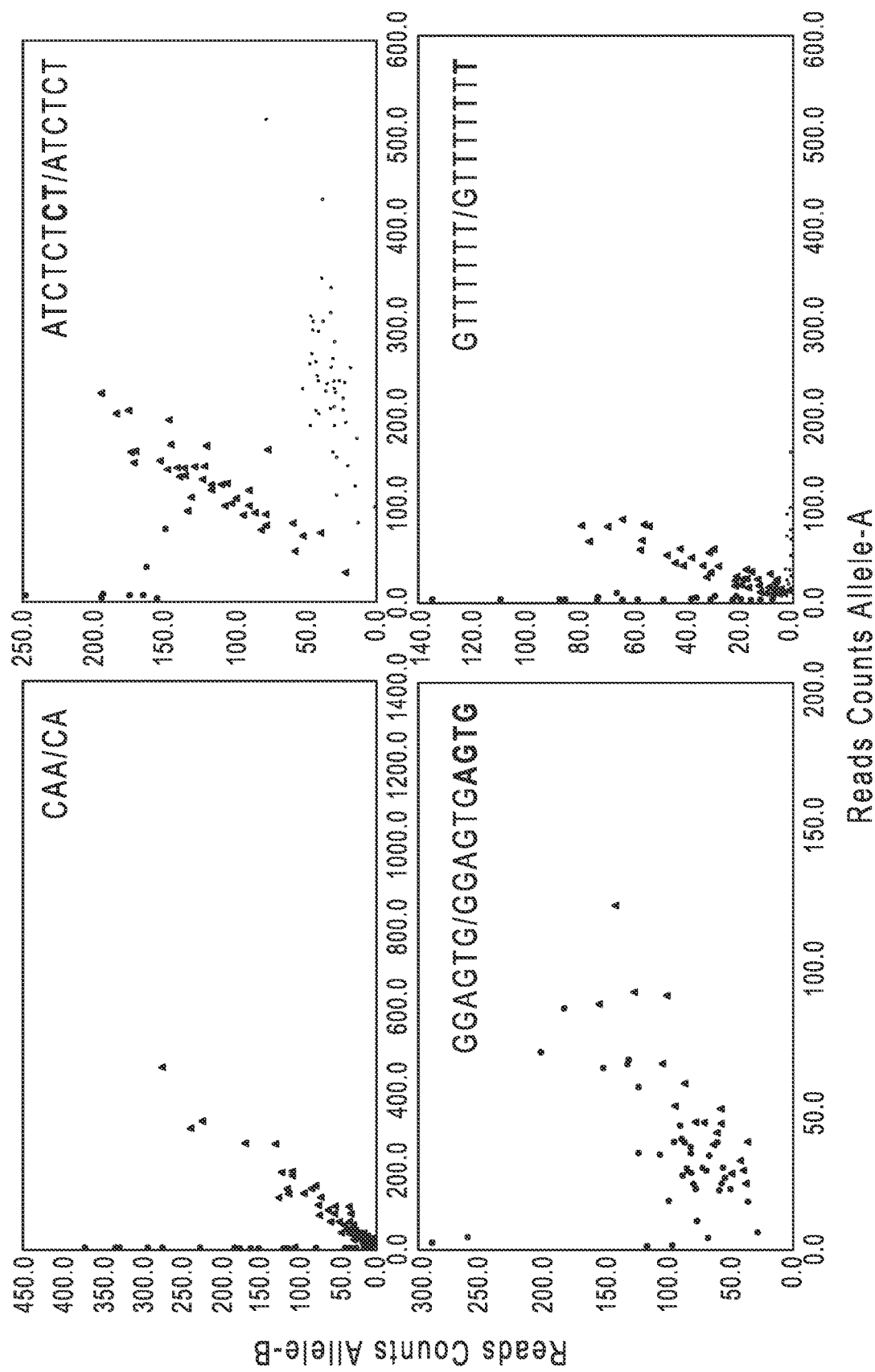
FIG. 40 shows INDELs and short tandem repeat (STR) genotyped using the disclosed method. In each example three complementary polynucleotides are used for each target polynucleotide (two first complementary polynucleotides, LHSs, and one second complementary polynucleotide, RHS). Genotypes are BB (circles), AB (triangles) and AA (small circles). The sequence nature of the alteration detected in shown in text with allele-A/Allele-B. Repeat regions are in bold.

FIG. 40: IINDELS and STR genotyping: INDELs and short tandem repeat (STR) can be genotyped using the disclosed method.

The disclosed method can detect small insertions and deletions (INDELS) as well as short tandem repeats. The same probe design principals can also be used for large deletion events where fixed breakpoints are known. STR probe design can determine STR length though the use of multiple probes that span the length distribution of the STR. In each example three probes are used for each target polynucleotide (two LHS and one RHS). Genotypes are BB (circles), AB (triangles) and AA (small circles). The sequence nature of the alteration detected in shown in text with allele-A/Allele-B. Repeat regions are in bold.

Examples 20-24: Protocols for Use with the Presently Disclosed Method

Examples 20 and 21: 96-Well Plate+96-Well Plate, and 96-Well Plate+384-Well Plate, Both at 40 ul The presently described method was performed with liquid mixtures of complementary polynucleotides (probes). This is referred to as the "Two Plate Method" and required a 40 ul "standard" "full sized reaction."

The disclosed method was performed using a sample prepared from genomic DNA. The sample was added directly to a 96-well plate and heated at 98° C. for five minutes. A mixture of complementary polynucleotides probe and hybridization buffer was added to each well of a 96-well plate, sealed and hybridized overnight. A ligation mixture was added and the first and second complementary polynucleotides were ligated. In some cases, four 96-well plates were PCR on a single 384-well plate.

The sample was cooked. The amount of genomic sample DNA was adjusted to 40 ng/ul (5 ul to 10 ul) as required with TE_8.3 and was plated into Hybridization 96-well plate. The plate was heated at 98° C. for 5 minutes, then cooled to room temperature (RT).

3.0 ul of water, 3.0 ul of Hybridization Buffer contained 1.5M KCl, 300 mM Tris-HCl pH=8.5, 1 mM EDTA and 3.0 ul of 100 pM complementary polynucleotide (probe) mixture (100 pM of each set of complementary polynucleotide in TE pH-8.0) was added and the plate was heated to 98° C. for 1 minute, and 60° C. overnight.

The ligation mixture comprising 27.8 ul H20, 4.0 ul 10× Ligase Buffer and 0.2 ul Taq DNA Ligase was added to each well, and the plate is heated to 54° C. for 15 min.

An aliquote from each well is mixed with a unique combination of left index and right index PCR primers. The mixture comprises 3.0125 ul H20, 0.0375 UL Left Index 100 uM, 2.0 ul Right Index 1.875 uM and 1.2 ul Ligase Reaction. These reactions can be set up in 96 well plates OR in 384 well plates OR in other plate and reaction vessel configurations.

PCR conditions are 94° C.-5 min, (94° C.-10 sec, 65° C.-15 sec)×32 cycles, 72° C.-1 min, 8° C.-hold.

After PCR, compatible 96 well or 384-well PCR plates were consolidated into single library. Two volumes of Zymo Binding buffer were added using a 10 ml pipette and completely mixed. The All the liquid was passed through a Zymo-100 column (2.5K for >min). The column was rinsed twice with 5 mis of wash buffer, and spin, and flow through discarded. The column was washed twice with 600 ul of wash buffer, and spin, and flow through discarded. The column was placed into a clean receiving tube and spun at full speed for 5 minutes. This was repeated and then the column was then placed into a clean receiving tube 1.5 ml with cap and 150 ul of TE pH8.0 added, let sit for one minute, and the tube was spun at 2 k for 1 minute. The spin through is the library.

The library was then quantified by using the agarose gel to approximate the concentration based on the 100 bp ladder and on a Bioanalzyer 2100 DNA100 chip.

The library concentration is adjusted as per sequencing platform recommendations and sequence data is generated (as per sequencing platform manufactures protocols).

Example 22: 384-Well Plate with 2 ul DNA, and Dried Probe Mixture

The presently described method was performed with complementary polynucleotides that were dried onto a plate. These are a further variation of the examples 20 and 21. For these experiments, a mixture of probe, hybridization buffer and water were dried into a 384-well plate. Heated genomic DNA was then added directly to the plate, sealed and hybridized overnight. The hybridization plate was then used as the PCR plate, in this one plate method.

The dried complementary polynucleotides (probes) were prepared using 150 ul of Hybridization Buffer (1.5M KCl, 300 mM Tris-HCl pH=8.5, 1 mM EDTA), 150 ul of 100 pM Probe mixture. (100 pM of each probe set in TE pH=8.0), 700 ul of water. 2.0 ul was added to each well, but the plate was not covered. The plate was spun down, and incubated at 50° C. until dry.

Input DNA was adjusted to 20 ng/ul (3 to 5 ul) as required with TE_8.3. 5 ul was heated to 98° C. for 5 minutes, cooled to RT, and then spun down.

2.0 ul of cooked (heated) sample DNA was added to the dried Probe/Buffer plate, the plate sealed and spun down. The temperature was held at RT for 10 to 20 minutes. The plate was then vortexed and spun down and sealed. Hybridization was then begun at 98° C. for 1 minute, and 60° C. overnight (at least 16 hours)

The ligation mixture containing 5.56 ul H20, 0.8 10× Ligase Buffer (fully re-suspended and fresh), and 0.04 ul of Ligase was created. The plate was held between 54 and 60° C. and 6.4 ul ligation mixture was added. The plate was sealed, vortexed, reheated, spun down, and incubated at 15 min 54° C. and 1 min at 98° C., and hold at 8° C., ice or freeze.

The PCR index mixture contained 12.5 ul 2×PCR Master Mix, 0.4625 H20, 0.0375 ul Left Index 200 uM and is kept on ice.

The PCR reactions were mixed at room temperature. 13.0 ul of PCR cocktail was dispensed (first three components) directly into the Hybridization/Ligation 384-well PCR plate. The plate was spun down in plate spinner briefly. 4.0 ul of the Right Index 1.875 uM 384-well plate was mapped onto the PCR plate. The plate was spun down in plate spinner briefly. The plate was sealed with a heated foil seal, and spun down at 3K for 1 minute. The plate was then moved to the PCR machine and thermocycle for 32×. [94° C.-5 min, (94° C.-10 sec, 65° C.-15 sec)×32 cycles, 72° C.-1 min, 8° C.-hold).

After PCR, compatible 384-well PCR plates were consolidated into single library. Two volumes of Zymo Binding buffer were added using a 10 ml pipette and completely mixed. The All the liquid was passed through a Zymo-100 column (2.5K for >min). The column was rinsed twice with 5 mis of wash buffer, and spin, and flow through discarded. The column was washed twice with 600 ul of wash buffer, and spin, and flow through discarded. The column was placed into a clean receiving tube and spun at full speed for 5 minutes. This was repeated and then the column was then placed into a clean receiving tube 1.5 ml with cap and 150 ul of TE pH8.0 added, let sit for one minute, and the tube was spun at 2 k for 1 minute. The spin through is the library.

The library was then quantified by using the agarose gel to approximate the concentration based on the 100 bp ladder and on a Bioanalzyer 2100 DNA100 chip.

The library concentration is adjusted as per sequencing platform recommendations and sequence data is generated (as per sequencing platform manufactures protocols).

Example 23: 384-Well Plate+384-Well Plate with 2 ul

Sample DNA was added directly to the 384-plate and heated at 98° C. for five minutes. A mixture of complementary polynucleotides, hybridization buffer and water were added to each well of a 384-well plate, sealed and hybridized overnight. The ligation mixture was added and the probes were ligated. Then an aliquote is moved to a second 384 well plate and the PCR reaction to add the sample index(es) are performed. In all examples other reaction configurations and vessels can be used.

The sample DNA was adjusted to 20 ng/ul (5 ul to 10 ul) as required with TE_8.3. DNA could vary 20 to 200 ng/ul.

2 ul was plated into a Hybridization 384 well plate. The plate sealed with temporary tape seal, spun down 4 k 1 min, then heated at 98° C. for 5 minutes, cooled to RT, and then spun down 4 k for 1 min.

A mix of complementary polynucleotide (probe) and buffer mix was prepared. The mixtures contained 0.6 ul of Hybridization Buffer [1.5M KCl, 300 mM Tris-HCl pH=8.5, 1 mM EDTA], 0.6 ul of 100 pM Probe mixture. [100 pM of each probe set in TE pH=8.0], 0.5 ul of water The sample DNA was then hybridized with the complementary polynucleotides (probes), at 98° C. for 1 minute, and 60° C. overnight (for at least 20 hrs. but not >24 hrs) in a thermal cycler.

The annealed first and second complementary polynucleotides were ligated by preparing a ligation mixture. The mixture contained 11.12 ul H20, 1.6 ul 10× Ligase Buffer, and 0.04 ul Taq DNA Ligase. The 60° C. incubation was shifted to 54 V. 12.8 ul of the ligase mix was dispensed and mixed into each well. The plate was sealed and incubated 54° C. for 15 minutes, 98° C. for 1 min, 8° C. forever. After 1 minute, the plate was removed, and drops shaken down, by hand. The plate was then placed into a rack and vortexed 10 seconds, returned to heat block for 30 seconds, vortexed (adapter was used to avoid rubber bits on the plate and getting into PCR block), and the plate quickly centrifuged in the plate spinner and returned to heat block until program finished. The plate was then spun down at 4K for 1 min.

Left Indexes were selected, one for each 384-well plate. A PCR mixture was prepared for the needed reactions. The mixture contained 6.25 ul 2×PCR Master Mix, 3.0125 H20, 0.0375 ul Left Index 200 uM, 2.0 ul Right Index 1.875 uM, and 1.2 ul Ligase Reaction, and the mixture kept on ice.

The PCR reactions were mixed at room temperature. 9.3 ul of PCR cocktail was dispensed (first three components) directly into a 384-well PCR plate and the plate was spun down. 2.0 ul of the unique Right Index 1.875 uM 384-well plate was put in each well of the PCR plate. (1 to 1 Mapping). The plate was spun down. 1.0 ul from each well of the hybridization/ligation 384-well plate was mapped onto the PCR plate. (1 to 1 Mapping). The plate sealed, and spun down The plate was then moved to the PCR machine and thermocycle for 32×. [94° C.-5 min, (94° C.-10 sec, 65° C.-15 sec)×32 cycles, 72° C.-1 min, 8° C.-hold).

After PCR, compatible 384-well PCR plates (one with differing left indexing primers) were consolidated into single library. Two volumes of Zymo Binding buffer were added using a 10 ml pipette and completely mixed. The All the liquid was passed through a Zymo-100 column (2.5K for >min). The column was rinsed twice with 5 mls of wash buffer, and spin, and flow through discarded. The column was washed twice with 600 ul of wash buffer, and spin, and flow through discarded. The column was placed into a clean receiving tube and spun at full speed for 5 minutes. This was repeated and then the column was then placed into a clean receiving tube 1.5 ml with cap and 150 ul of TE pH8.0 added, let sit for one minute, and the tube was spun at 2 k for 1 minute. The spin through is the library.

The library was then quantified by using the agarose gel to approximate the concentration based on the 100 bp ladder and on a Bioanalzyer 2100 DNA100 chip.

The library concentration is adjusted as per sequencing platform recommendations and sequence data is generated (as per sequencing platform manufactures protocols).

Example 24: 384-Well Plate with 2 ul Dried Probe/Buffer+2$^{nd}$ 384-Well PCR Plate The presently described method was performed with complementary polynucleotides that were dried onto a plate. For these experiments, a mixture of probe, hybridization buffer and water were dried into a 384-well plate. The pre-cooked sample DNA was then added directly to the plate, sealed and hybridized overnight, and then ligated. A second PCR 384-well plate was then used and is seeded by the first hybridization/ligation 384-well plate.

The complementary polynucleotides (probes) were prepared using 150 ul of Hybridization Buffer (1.5M KCl, 300 mM Tris-HCl pH=8.5, 1 mM EDTA), 150 ul of 100 μM Probe mixture. (100 pM of each probe set in TE pH=8.0), 700 ul of water. 2.0 ul was added to each well, but the plate was not covered. The plate was spun down, and incubated at 50° C. until dry.

The sample DNA was adjusted to 20 ng/ul (3 to 5 ul) as required with TE_8.3. 5 ul was heated to 98° C. for 5 minutes, cooled to RT, and then spun down.

2.0 ul of heated sample DNA was added to the dried Probe/Buffer plate, the plate sealed and spun down. The temperature was held at RT for 10 to 20 minutes. The plate was then vortexed and spun down. Hybridization was then begun at 98° C. for 1 minute, and 60° C. overnight (at least 16 hrs.)

The ligation mixture contained 5.56 ul H20, 0.8 10× Ligase Buffer (fully resuspended and fresh), and 0.04 ul of Ligase. The mixture was then mixed by inversion well and spun down. The thermal program was advanced to 54° C. and PAUSEd. 6.4 ul ligation mixture was added to each well. The plate was sealed with tape seal, vortexed, spun down, and Incubated at 15 min 54° C. and 1 min at 98° C., and hold at 8° C., ice or freeze.

The Right Index Plate was thawed at RT or 37° C., spun down, and kept on ice. A single Left Index was selected. The PCR reaction is 6.25 ul 2×PCR Master Mix, 3.0125 H20, 0.0375 ul Left Index 100 uM, 2.0 ul Right Index 1.875 uM (1' to 384'), and 1.2 ul Ligase Reaction from the first hybridization/ligation 384-well plate.

The PCR reactions were mixed at room temperature. 9.3 ul of PCR cocktail was dispensed (first three components) into a 384-well PCR plate. The plate was spun down. 2.0 ul of the Right Index 1.875 uM 384-well plate was mapped onto the PCR plate. (1 to 1 Mapping). The plate was spun down. 1.0 ul of the Hybridization/Ligation 384-well plate was mapped onto the PCR plate. (1 to 1 Mapping). The plate was sealed, spun down and thermocycled for 32×. [94° C.-5 min, (94° C.-10 sec, 65° C.-15 sec)×32 cycles, 72° C.-1 min, 8° C.-hold).

After PCR, compatible 384-well PCR plates were consolidated into single library. Two volumes of Zymo Binding buffer were added using a 10 ml pipette and completely mixed. The All the liquid was passed through a Zymo-100 column (2.5K for >min). The column was rinsed twice with 5 mls of wash buffer, and spin, and flow through discarded. The column was washed twice with 600 ul of wash buffer, and spin, and flow through discarded. The column was placed into a clean receiving tube and spun at full speed for 5 minutes. This was repeated and then the column was then placed into a clean receiving tube 1.5 ml with cap and 150 ul of TE pH8.0 added, let sit for one minute, and the tube was spun at 2 k for 1 minute. The spin through is the library.

The library was then quantified by using the agarose gel to approximate the concentration based on the 100 bp ladder and on a Bioanalzyer 2100 DNA100 chip.

The library concentration is adjusted as per sequencing platform recommendations and sequence data is generated (as per sequencing platform manufactures protocols).

Example 25

The Ion Torrent data in example 16 (FIG. 26) also provides an example of how altered read configurations can be used to generate the sequence data. For example, currently for sequence data generation on the PGM a long read is required. The sequence read contains the left sample ID barcode, some universal sequence (this could be eliminated), the allele bar code and the loci.

Figure 41:
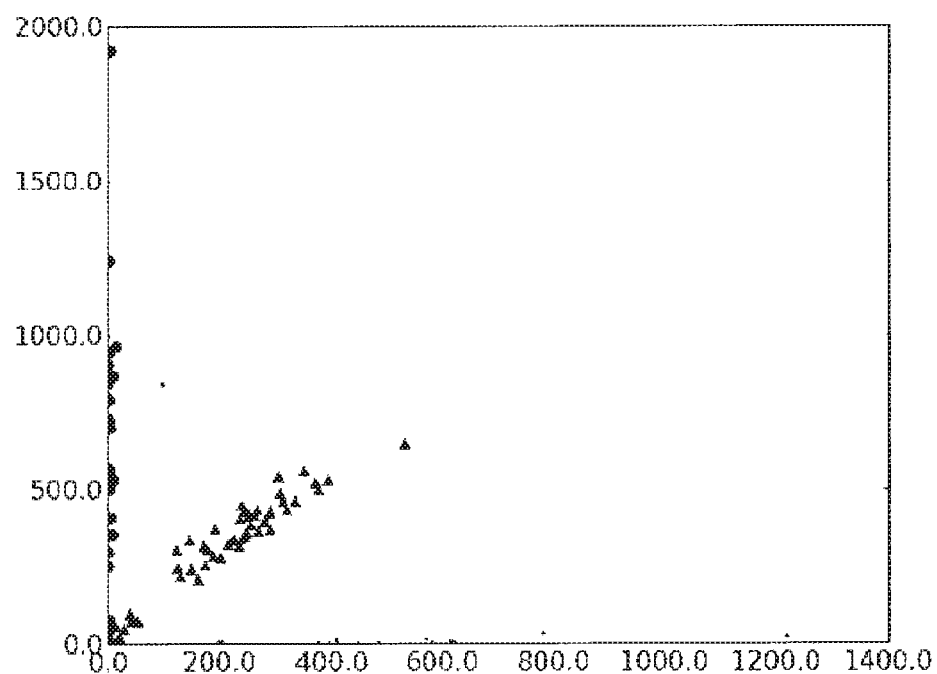
FIG. 41 Genotype cluster plot for a single loci (rs17871214) using an altered read state of the GAIIx sequencing instrument.

The altered read characteristics can also be demonstrated on an Illumina instrument. The read characteristics of the sequencing Instrument can be altered and genotyping information retrieved. To demonstrate this, we extended the read one sequencing primer by one single G base. This shorter read could be accommodated as the molecules to be sequenced all contained a G at that position. This altered read state did not affect the genotyping results (FIG. 41) and the three expected genotype clusters were still present.

We claim:

1. A method of determining the presence or absence of a target polynucleotide in a sample, the method comprising:
   a) combining
      i) a sample comprising one or more target polynucleotides, the target polynucleotide comprising a first target sequence and a second target sequence;
      ii) a first complementary polynucleotide comprising a first complementary sequence, wherein the first complementary sequence is complementary to the first target sequence of the target polynucleotide; and
      iii) a second complementary polynucleotide comprising a second complementary sequence, wherein the second complementary sequence is complementary to the second target sequence of the target polynucleotide;
   b) incubating the first and second complementary polynucleotides to the target polynucleotide under conditions that allow hybridization of complementary sequences;
   c) if the first complementary polynucleotide and the second complementary polynucleotide are hybridized to the same target polynucleotide, then joining the first complementary polynucleotide to the second complementary polynucleotide, to form a first product polynucleotide; and
   d) detecting the presence or absence of the product polynucleotide, said detecting comprising comparing a first detection and a second detection, wherein the first detection is indicative the quantity of the first polynucleotide from a specific locus and the second detection is indicative the quantity of a second polynucleotide from the specific locus, and wherein the locus is determined to be homozygous;
   if the quantity ratio for one product polynucleotide from a locus is greater than about 0.7 of the sum of the quantity of the first product polynucleotide and the quantity of the second product polynucleotide from the same locus, or
   if the quantity ratio for one product polynucleotide from a locus is less than about 0.3 of the sum of the quantity of the first product polynucleotide and the quantity of the second product polynucleotide from the same locus.

2. The method of claim 1, wherein the joining is by ligation of the first and second complementary polynucleotides.

3. The method of claim 1 further comprising amplifying the product polynucleotide.

4. The method of claim 1, wherein:
   i) the first target polynucleotide further comprises a polymorphic nucleotide or nucleotide sequence positioned between the first and second target sequence; and
   ii) the first complementary polynucleotide further comprises a first polymorphic nucleotide or nucleotide sequence, wherein the polymorphic nucleotide is complementary to the polymorphic nucleotide or nucleotide sequence of the first target polynucleotide.

5. The method of claim 1, wherein:
   i) the first target polynucleotide further comprises a polymorphic nucleotide or nucleotide sequence positioned between the first and second target sequence;
   ii) the first complementary polynucleotide further comprises a first 3' polymorphic nucleotide or nucleotide sequence, wherein the polymorphic nucleotide is complementary to the polymorphic nucleotide or nucleotide sequence of the first target polynucleotide; and
   iii) the second complementary polynucleotide further comprises a 5' phosphorylated nucleotide.

6. The method of claim 1 further comprising a second target polynucleotide comprising the first and the second target sequence, and a polymorphic nucleotide or nucleotide sequence that differs from the polymorphic nucleotide or nucleotide sequence of the first target polynucleotide, and a plurality of first complementary polynucleotides that differ in the identity of the 3' polymorphic nucleotide or nucleotide sequence.

7. The method of claim 1, wherein the first complementary polynucleotide further comprises a polymorphism-specific tag or allele-specific tag, said tag sequence corresponding to the identity of a 3' polymorphic nucleotide or nucleotide sequence.

8. The method of claim 1, wherein the first and/or second complementary polynucleotides comprise a locus-specific tag sequence, said locus-specific tag sequence corresponding to the identity of the locus and/or the first and/or second target sequences.

9. The method of claim 1, wherein the first and/or second complementary polynucleotide further comprises a sample-specific tag sequence, said sample-specific tag sequence corresponding to the identity of the sample.

10. The method of claim 1, wherein the locus is determined to be heterozygous if the quantity ratio for one product polynucleotide from a locus is between about 0.25 and about 0.75 of the sum of the quantity of the first product polynucleotide and the quantity of the second product polynucleotide from the same locus.

11. A method of determining the allele frequency of one or more target polynucleotides of a plurality of target polynucleotides in a sample, the method comprising:
　a) combining a sample comprising one or more of the plurality of target polynucleotides with a plurality of sets of complementary polynucleotides, said one or more of the plurality of target polynucleotides suspected to have a site of a single nucleotide polymorphism (SNP) containing a polymorphic nucleotide;
　wherein each of the plurality of sets of complementary polynucleotides comprises:
　(i) a first complementary polynucleotide comprising a complementary sequence to a first target sequence of a target polynucleotide, a first allele-specific barcode, and a site of a single nucleotide polymorphism (SNP) containing a first polymorphic nucleotide,
　(ii) a second complementary polynucleotide comprising a complementary sequence to the first target sequence, a second allele-specific barcode, and a site of a single nucleotide polymorphism (SNP) containing a second polymorphic nucleotide; and
　(iii) a third complementary polynucleotide comprising a complementary sequence to a second target sequence of the target polynucleotide,
　wherein the allele-specific barcodes are not complementary to the first target sequence;
　b) incubating the plurality of sets of complementary polynucleotides with the plurality of target polynucleotides under conditions that allow hybridization of complementary sequences;
　c) joining a pair of the first and third complementary polynucleotides and/or joining a pair of the second and third complementary polynucleotides by a ligation reaction when both complementary polynucleotides of each pair are hybridized to the target polynucleotide to form one or more product polynucleotides; and
　d) detecting the presence of one or more product polynucleotides to determine the allele frequency of the target polynucleotide; and
　e) determining the target polynucleotide is homozygous if the frequency of one allele is 0.7 or greater, or 0.3 or lower, and determining the target polynucleotide is heterozygous if the frequency of one allele is between 0.3 and 0.7.

12. The method of claim 11, further comprising an enriching step before the detecting step, wherein each of the complementary polynucleotides comprises a sequence complementary to an amplification primer, and the enriching step comprises amplification of the one or more product polynucleotides.

13. The method of claim 12, wherein the enriching step comprises selecting the one or more product polynucleotides or removal or destruction of one or more non-product polynucleotides.

14. The method of claim 11, wherein the allele-specific barcode in the first complementary polynucleotide is a locus-allele-specific barcode that identifies both the locus and the allele.

15. The method of claim 11, wherein the allele-specific barcode in the second complementary polynucleotide is a locus-allele-specific barcode that identifies both the locus and the allele.

16. The method of claim 12, wherein at least one of the sequences complementary to an amplification primer comprises a sample-specific tag sequence corresponding to the identity of the sample.

17. A method of determining the allele frequency of one or more target polynucleotides of a plurality of target polynucleotides in a sample, the method comprising:
　a) combining a sample comprising one or more of the plurality of target polynucleotides with a plurality of sets of complementary polynucleotides, said one or more of the plurality of target polynucleotides suspected to have a site of a single nucleotide polymorphism (SNP) containing a polymorphic nucleotide;
　wherein each of the plurality of sets of complementary polynucleotides comprises;
　(i) a first complementary polynucleotide comprising a complementary sequence to a first target sequence of a target polynucleotide, a first allele-specific barcode, and a site of a single nucleotide polymorphism (SNP) containing a first polymorphic nucleotide;
　(ii) a second complementary polynucleotide comprising a complementary sequence to the first target sequence, a second allele-specific barcode, and a site of a single nucleotide polymorphism (SNP) containing a second polymorphic nucleotide; and
　(iii) a third complementary polynucleotide comprising a complementary sequence to a second target sequence of the target polynucleotide,
　wherein the allele-specific barcodes are not complementary to the first target sequence and are 5 to 15 nucleotides in length;
　b) incubating the plurality of sets of complementary polynucleotides with the plurality of target polynucleotides under conditions that allow hybridization of complementary sequences;
　c) joining a pair of the first and third complementary polynucleotides and/or joining a pair of the second and third complementary polynucleotides by a ligation reaction when both complementary polynucleotides of each pair are hybridized to the target polynucleotide to form one or more product polynucleotides;
　d) amplifying the one or more product polynucleotides, wherein each of the first, second, and third complementary polynucleotides comprises a sequence complementary to an amplification primer bound by a primer for the amplifying, wherein at least one of the sequences complementary to an amplification primer comprises a sample-specific tag sequence corresponding to the identity of the sample; and e) detecting the presence of one or more product polynucleotides to determine the allele frequency of the target nucleotide; and f) determining the target polynucleotide is homozygous if the frequency of one allele is 0.7 or greater, or 0.3 or lower, and determining the target polynucleotide is heterozygous if the frequency of one allele is between 0.3 and 0.7.

* * * * *

SEQUENCE LISTING

```
<160> NUMBER OF SEQ ID NOS: 28

<210> SEQ ID NO 1
<211> LENGTH: 21
<212> TYPE: DNA
<213> ORGANISM: Artificial
<220> FEATURE:
<223> OTHER INFORMATION: Primer

<400> SEQUENCE: 1
agacgtgtgc tcttccgatc t                                        21

<210> SEQ ID NO 2
<211> LENGTH: 33
<212> TYPE: DNA
<213> ORGANISM: Artificial
<220> FEATURE:
<223> OTHER INFORMATION: Primer

<400> SEQUENCE: 2
acactctttc cctacacgac gctcttccga tct                           33

<210> SEQ ID NO 3
<211> LENGTH: 33
<212> TYPE: DNA
<213> ORGANISM: Artificial
<220> FEATURE:
<223> OTHER INFORMATION: Primer

<400> SEQUENCE: 3
ctcggcattc ctgctgaacc gctcttccga tct                           33

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
ggtgggttgg tggagttgag                                          20

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
acacgacggt cttccgactc                                          20

<210> SEQ ID NO 6
<211> LENGTH: 20
<212> TYPE: DNA
<213> ORGANISM: Artificial
<220> FEATURE:
<223> OTHER INFORMATION: Primer
```

```
<400> SEQUENCE: 6
tccgcctctc ccacgccgtc                                              20

<210> SEQ ID NO 7
<211> LENGTH: 33
<212> TYPE: DNA
<213> ORGANISM: Artificial
<220> FEATURE:
<223> OTHER INFORMATION: Primer

<400> SEQUENCE: 7
acactctttc cctacacgac gctcttccga tct                               33

<210> SEQ ID NO 8
<211> LENGTH: 33
<212> TYPE: DNA
<213> ORGANISM: Artificial
<220> FEATURE:
<223> OTHER INFORMATION: Primer

<400> SEQUENCE: 8
acactctttc cctacacgac gctcttccga tct                               33

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9
tccgcctctc ccacgccgtc                                              20

<210> SEQ ID NO 10
<211> LENGTH: 33
<212> TYPE: DNA
<213> ORGANISM: Artificial
<220> FEATURE:
<223> OTHER INFORMATION: Primer

<400> SEQUENCE: 10
ctcggcattc ctgctgaacc gctcttccga tct                               33

<210> SEQ ID NO 11
<211> LENGTH: 58
<212> TYPE: DNA
<213> ORGANISM: Artificial
<220> FEATURE:
<223> OTHER INFORMATION: Primer

<400> SEQUENCE: 11
aatgatacgg cgaccaccga gatctacact ctttccctac acgacgctct tccgatct    58

<210> SEQ ID NO 12
<211> LENGTH: 61
<212> TYPE: DNA
<213> ORGANISM: Artificial
<220> FEATURE:
<223> OTHER INFORMATION: Primer

<400> SEQUENCE: 12
caagcagaag acggcatacg agatcggtct cggcattcct gctgaaccgc tcttccgatc  60
t                                                                  61
```

<210> SEQ ID NO 13
<211> LENGTH: 33
<212> TYPE: DNA
<213> ORGANISM: Artificial
<220> FEATURE:
<223> OTHER INFORMATION: Primer

<400> SEQUENCE: 13
acactctttc cctacacgac gctcttccga tct                         33

<210> SEQ ID NO 14
<211> LENGTH: 12
<212> TYPE: DNA
<213> ORGANISM: Artificial
<220> FEATURE:
<223> OTHER INFORMATION: First Complimentary Polynucleotide

<400> SEQUENCE: 14
cgtacgtacg ta                                                12

<210> SEQ ID NO 15
<211> LENGTH: 10
<212> TYPE: DNA
<213> ORGANISM: Artificial
<220> FEATURE:
<223> OTHER INFORMATION: Second Complimentary Polynucleotide

<400> SEQUENCE: 15
cgcatagcga                                                   10

<210> SEQ ID NO 16
<211> LENGTH: 40
<212> TYPE: DNA
<213> ORGANISM: Artificial
<220> FEATURE:
<223> OTHER INFORMATION: Target Polynucleotide

<400> SEQUENCE: 16
atgcatgcat gcatgcatgc atgcgtatgg ctatgcatgc                  40

<210> SEQ ID NO 17
<211> LENGTH: 12
<212> TYPE: DNA
<213> ORGANISM: Artificial
<220> FEATURE:
<223> OTHER INFORMATION: Primer

<400> SEQUENCE: 17
dgtacgtacg ta                                                12

<210> SEQ ID NO 18
<211> LENGTH: 12
<212> TYPE: DNA
<213> ORGANISM: Artificial
<220> FEATURE:
<223> OTHER INFORMATION: Primer

<400> SEQUENCE: 18
cgtacgtacg tt                                                12

<210> SEQ ID NO 19
<211> LENGTH: 12
<212> TYPE: DNA
<213> ORGANISM: Artificial
<220> FEATURE:
<223> OTHER INFORMATION: Primer

```
<400> SEQUENCE: 19
cgtacgtacg tc                                                    12

<210> SEQ ID NO 20
<211> LENGTH: 33
<212> TYPE: DNA
<213> ORGANISM: Artificial
<220> FEATURE:
<223> OTHER INFORMATION: Primer

<400> SEQUENCE: 20
acactctttc cctacacgac gctcttccga tct                             33

<210> SEQ ID NO 21
<211> LENGTH: 12
<212> TYPE: DNA
<213> ORGANISM: Artificial
<220> FEATURE:
<223> OTHER INFORMATION: Primer

<400> SEQUENCE: 21
cgtacgtacg ta                                                    12

<210> SEQ ID NO 22
<211> LENGTH: 10
<212> TYPE: DNA
<213> ORGANISM: Artificial
<220> FEATURE:
<223> OTHER INFORMATION: Primer

<400> SEQUENCE: 22
ggcatagcga                                                       10

<210> SEQ ID NO 23
<211> LENGTH: 12
<212> TYPE: DNA
<213> ORGANISM: Artificial
<220> FEATURE:
<223> OTHER INFORMATION: Primer

<400> SEQUENCE: 23
cgtacgtacg ta                                                    12

<210> SEQ ID NO 24
<211> LENGTH: 10
<212> TYPE: DNA
<213> ORGANISM: Artificial
<220> FEATURE:
<223> OTHER INFORMATION: Primer

<400> SEQUENCE: 24
cgcatagcga                                                       10

<210> SEQ ID NO 25
<211> LENGTH: 12
<212> TYPE: DNA
<213> ORGANISM: Artificial
<220> FEATURE:
<223> OTHER INFORMATION: Primer

<400> SEQUENCE: 25
cgtacgtacg ta                                                    12

<210> SEQ ID NO 26
```

```
<211> LENGTH: 12
<212> TYPE: DNA
<213> ORGANISM: Artificial
<220> FEATURE:
<223> OTHER INFORMATION: Primer

<400> SEQUENCE: 26
cgtacgtacg tt                                                          12

<210> SEQ ID NO 27
<211> LENGTH: 12
<212> TYPE: DNA
<213> ORGANISM: Artificial
<220> FEATURE:
<223> OTHER INFORMATION: Primer

<400> SEQUENCE: 27
cgtacgtacg tc                                                          12

<210> SEQ ID NO 28
<211> LENGTH: 12
<212> TYPE: DNA
<213> ORGANISM: Artificial
<220> FEATURE:
<223> OTHER INFORMATION: Primer

<400> SEQUENCE: 28
cgtacgtacg tg                                                          12
```